US011096931B2

(12) United States Patent
Last et al.

(10) Patent No.: US 11,096,931 B2
(45) Date of Patent: Aug. 24, 2021

(54) AMIDE DERIVATIVES USEFUL IN THE TREATMENT OF HBV INFECTION OR HBV-INDUCED DISEASES

(71) Applicant: Janssen Sciences Ireland Unlimited Company, County Cork (IE)

(72) Inventors: Stefaan Julien Last, Beveren (BE); Bart Rudolf Romanie Kesteleyn, Berlare (BE); Sandrine Céline Grosse, Turnhout (BE); Tim Hugo Maria Jonckers, Heist-op-den-Berg (BE); Jan Martin Berke, Willebroek (BE); Geerwin Yvonne Paul Haché, Kapellen (BE); Edgar Jacoby, Vosselaar (BE); Carolina Martinez Lamenca, Beerse (BE); Morgan Charles R. Lecomte, Evere (BE); Abdellah Tahri, Sint-Pieters-Leeuw (BE); Sarah Sauviller, Geel (BE); Karen Maria Vergauwen, Edegem (BE)

(73) Assignee: Janssen Sciences Ireland Unlimited Company, County Cork (IE)

( * ) Notice: Subject to any disclaimer, the term of this patent is extended or adjusted under 35 U.S.C. 154(b) by 0 days.

(21) Appl. No.: 16/798,199

(22) Filed: Feb. 21, 2020

(65) Prior Publication Data
US 2020/0268730 A1  Aug. 27, 2020

(30) Foreign Application Priority Data

Feb. 22, 2019 (EP) ..................................... 19158758
Feb. 27, 2019 (EP) ..................................... 19159717

(51) Int. Cl.
| | |
|---|---|
| *A61K 31/4439* | (2006.01) |
| *C07D 403/12* | (2006.01) |
| *C07D 405/14* | (2006.01) |
| *C07D 307/34* | (2006.01) |
| *A61P 31/20* | (2006.01) |
| *A61K 31/4192* | (2006.01) |
| *C07D 409/14* | (2006.01) |
| *A61K 31/40* | (2006.01) |
| *A61K 31/41* | (2006.01) |
| *A61K 31/4178* | (2006.01) |
| *C07D 401/14* | (2006.01) |
| *C07D 207/34* | (2006.01) |

(52) U.S. Cl.
CPC .......... *A61K 31/4439* (2013.01); *A61K 31/40* (2013.01); *A61K 31/41* (2013.01); *A61K 31/4178* (2013.01); *A61K 31/4192* (2013.01); *A61P 31/20* (2018.01); *C07D 207/34* (2013.01); *C07D 401/14* (2013.01); *C07D 403/12* (2013.01); *C07D 405/14* (2013.01); *C07D 409/14* (2013.01)

(58) Field of Classification Search
CPC .... C07D 207/34; C07D 401/14; A61K 31/40; A61P 31/20
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |

(Continued)

FOREIGN PATENT DOCUMENTS

| | | |
|---|---|---|
| CA | 2950807 A1 | 12/2013 |
| CN | 101039919 A | 9/2007 |

(Continued)

OTHER PUBLICATIONS

Online Registry via STN Dec. 22, 2008, RN 1088200-12-7.

(Continued)

*Primary Examiner* — Kamal A Saeed

(57) ABSTRACT

The application relates to amide derivatives, processes for their preparation, pharmaceutical compositions, and their uses, more particularly their uses in treating chronic hepatitis B virus (HBV) infection.

16 Claims, No Drawings

(56) References Cited

U.S. PATENT DOCUMENTS

| | | |
|---|---|---|
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,722,742 B2 | 5/2014 | Reyes |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 10,071,961 B2 | 9/2018 | Vandyck et al. |
| 10,125,094 B2 | 11/2018 | Vandyck |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams et al. |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | |
|---|---|---|
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |
| JP | 2008179621 A | 7/2008 |
| JP | 2008525406 A | 7/2008 |
| JP | 2010535172 A | 11/2010 |
| WO | 198403281 A1 | 8/1984 |
| WO | 1992/07835 A1 | 5/1992 |
| WO | 1998023285 A1 | 6/1998 |
| WO | 1999/09022 A1 | 2/1999 |
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001025200 A1 | 4/2001 |
| WO | 2001051487 A1 | 7/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003/002518 A1 | 1/2003 |

(56) References Cited

FOREIGN PATENT DOCUMENTS

| | | |
|---|---|---|
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006/053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2007070556 A2 | 6/2007 |
| WO | 2008011476 A2 | 1/2008 |
| WO | 2008022171 A1 | 2/2008 |
| WO | 2008054605 A3 | 7/2008 |
| WO | 2008093614 A1 | 8/2008 |
| WO | 2008137794 A1 | 11/2008 |
| WO | 2008154819 A1 | 12/2008 |
| WO | 2009/018219 A2 | 2/2009 |
| WO | 2009016088 A1 | 2/2009 |
| WO | 2009062402 A1 | 5/2009 |
| WO | 2009086303 A1 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011002635 A1 | 1/2011 |
| WO | 2011035143 A2 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | 2013006394 A1 | 1/2013 |
| WO | 2013096744 A1 | 6/2013 |
| WO | 2013102655 A1 | 7/2013 |
| WO | 2013130703 A2 | 9/2013 |
| WO | 2013144129 A1 | 10/2013 |
| WO | 2013/174962 | 11/2013 |
| WO | 2013181584 A2 | 12/2013 |
| WO | 2013184757 A1 | 12/2013 |
| WO | 2014/033176 | 3/2014 |
| WO | 2014033167 A1 | 3/2014 |
| WO | 2014033170 A1 | 3/2014 |
| WO | 2014037480 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | 2017156255 A1 | 9/2017 |
| WO | 2018039531 A1 | 3/2018 |
| WO | 2019011323 A1 | 1/2019 |

OTHER PUBLICATIONS

Online Registry via STN, Mar. 2, 2007, RN 924514-21-6.
Online Registry via STN, Sep. 2, 2003, RN 577752-12-6.
Bennes, et al., "Recognition-induced control and acceleration of a pyroole Diels-Alder reaction", Tetrahedron Letters, vol. 42 : pp. 2377-2380 (2001).
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-21 (Feb. 2016).
Brezillon, et al., "Antiviral Activity of Bay 41-4109 on Hepatitis B Virus in Humanized Alb-uPA/SCID Mice", PLos ONE, vol. 6 (12): pp. e25096 (1-6) (Dec. 2011).
Cai, et al., "Identification of disubstituted sulfonamide compounds as specific inhibitors of hepatitis B virus covalently dosed circular DNA formuation, Antimicrobial agents and chemotherapy" , pp. 4277-4288 (May 29, 2012).
Campagna et al., "Sulfamoylbenzamide Derivatives Inhibit the Assembly of Hepatitis B Virus Nucleocapsids", Journal of Virology, ), vol. 87 (12): pp. 6931-6942 (Jun. 2013).
Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 9-12, 2011).
Carver, et al., Polyfunctionalisation of Imidazole via Sequential Imidazolyl Anion Formation, Tetrahedron, 1997, pp. 14481-14496, vol. 53 Issue 42.
Chang, et al., "NMR-spectroscopy-based Metabonomic Approach to the Analysis of Bay41-4109, a novel anti-HBV compound, induced Hepatotoxicity in Rats", Toxicology Letters, vol. 173: pp. 161-167 (2007).
Cho, et al., "2-Amino-N-(2,6-dichloropyridin-3-yl)acetamide derivatives as a novel class of HBV capsid assembly inhibitor", Journal of Viral Hepatitis, vol. 21: pp. 843-852 (2014).
Cowie, et al., "Mortality due to viral hepatitis in the Global Burden of Disease Study 2010: new evidence of an urgent global public health priority demanding action", Antiviral Therapy, vol. 18: pp. 953-954 (2013).
Delaney, et al., "Phenylpropenamide Derivatives AT-61 and AT-130 Inhibit Replication of Wild-Tpe and Lamivudine-Resistant Strains

(56) References Cited

OTHER PUBLICATIONS of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).
El-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).
El-Sharief, et al., "Synthesis of Different Types of Chlorinated Sulphonamides with Expected Insecticidal and Bactericidal Activities", Proceedings of the Indian National Science Academy, vol. 53(1): pp. 179-188 (1987).
Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).
Foley, "An Effecient Synthesis of 2-Chloro-3-carboethoxy or 2-Chloro-3-cyano-4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Geies, et al., Synthesis of some Thiazolo[3,2-a]pyrimidines, Phosphorus, Sulfur and Silicon, vol. 56: pp. 87-93 (1991).
Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Goodman, et al., "Discovery of potent, selective sulfonylfuran urea endothelial lipase inhibitors", Bioorganic & Medicinal Chemistry Letters, vol. 19:pp. 27-30 (2009).
Guo, et al., "HBc binds to the CpG island of HBV cccDNA and promotes an epigenetic permissive state", Epigenetics, vol. 6 (6): pp. 720-726 (Jun. 2011).
Hogan, et al., "Aqueous Process Chemistry: The Preparation of Aryl Sulfonyl Chlorides", Organic Process Research & Development, vol. 13: pp. 875-879 (2009).
Horig, et al., "From bench to Clinic and back : Perspective on the 1st IQPC translational Research conference", Journal of Translational Medicine, vol. 2(44): pp. 1-8 (Dec. 20, 2004).
Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, ( Oct. 2016).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Klumpp, et al., "High Antiviral Activity of the HBV Core Inhibitor NVR 3-778 in the Humanized UPA/SCID Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Jan. 1, 2007).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., "Progress in anti Hepatitus B Virus non-nucleosidic drugs, J. Liaoning Medical University, vol. 30(1): pp. 88-91 (Dec. 31, 2009.
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al., "Synthesis of Different Types of Chlorinated Sulphonamides with Expected Insecticidal and Antimicrobial Activities", Acta Pharmaceutica Jugoslavica, vol. 36 (3): pp. 301-310, (1986).
Mohebbi, et al., "An Overview of Hepatitis B Virus Surface Antigen Secretion Inhibitors", Frontier in Microbiology, vol. 9: pp. 1-9 (Apr. 2018).
Nijampatnam et al., "Recent advances in the development of HBV capsid assembly modulators", Current Opinion in Chemical Biology, vol. 50; pp. 73-79 (2019).
Online Registr via STN, Dec. 28, 2008, RN 1090750-88-1.
Online Registry via STN , Aug. 13, 2012, RN 1390589-54-4.
Online Registry via STN Feb. 2, 2007, RN 919040-39-4.
Online Registry via STN Feb. 2, 2007, RN 919040-53-2.
Online Registry via STN Feb. 2, 2007, RN 919040-55-4.
Online Registry via STN Aug. 6, 2012. RN 1386725-02-5.
Online Registry via STN Jun. 7, 2012, RN 1375909-37-7.
Online Registry via STN Dec. 8, 2012, RN 1389720-57-3.
Online Registry via STN Aug. 24, 2019, RN 311800-19-8.
Online Registry via STN Oct. 10, 2001, RN 361373-90-2.
Online Registry via STN Dec. 11, 2007, RN 957487-45-5.
Online Registry via STN Dec. 11, 2007, RN 957487-49-9.
Online Registry via STN Aug. 12, 2012, RN 1389686-79-6.
Online Registry via STN Aug. 13, 2012, RN 1390500-09-0.
Online Registry via STN Jan. 16, 2001, RN 314043-17-9.
Online Registry via STN Mar. 17, 2013, RN 1424462-66-7.
Online Registry via STN Mar. 18, 2010 , RN 1211415-65-4.
Online Registry via STN Sep. 18, 2012, RN 1394742-82-5.
Online Registry via STN 2010, RN 1253220-91-5.
Online Registry via STN Aug. 30, 2011, RN 1325664-90-1.
Online Registry via STN, Jan. 24, 2008, RN 296790-26-6.
Online Registry via STN, Feb. 2, 2007, RN 9019040-48-5.
Online Registry via STN, Feb. 2, 2007, RN 919040-37-2.
Online Registry via STN, May 6, 2011, RN 1291044-81-9.
Online Registry via STN, Sep. 6, 2011, RN 1328738-57-3.
Online Registry via STN, Oct. 7, 2008, RN 1057788-44-9.
Online Registry via STN, Oct. 7, 2008, RN 1057871-39-2.
Online Registry via STN, Jan. 9, 2001, RN 313253-89-3.

(56) References Cited

OTHER PUBLICATIONS

Online Registry via STN, Mar. 10, 2010, RN 1208400-27-4.
Online Registry via STN, Feb. 15, 2007, RN 921179-95-5.
Online Registry via STN, Aug. 15, 2011, RN 1317923-24-2.
Online Registry via STN, Aug. 15, 2011, RN 1318022-74-0.
Online Registry via STN, Mar. 17, 2003, RN 499189-09-2.
Online Registry via STN, May 18, 2011, RN 1296380-95-4.
Online Registry via STN, Oct. 18, 2000, RN 296894-70-7.
Online Registry via STN, Sep. 20, 2013, RN 1452780-00-5.
Online Registry via STN, Apr. 24, 2002, RN 406926-60-1.
Online Registry via STN, Apr. 28, 2011, RN 1286906-97-5.
Online Registry via STN, Apr. 19, 2008, RN 930914-71-9.
Patani, et al., "Bioisoterism: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Qidong You et al, Pharmaceutical Chemistry, Chemical Industry Press, Jan. 31, 2014, pp. 32-33, /.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schafer, et al., "Failure is an Option: Learning from unsuccessful proof-of-concepts trails", Drug Discovery Today, vol. 13 (21/22): pp. 913-916 (Nov. 2008).
Schroder, et al., "Arzneimittelchemie Passage", Arzneimittelchemei Grundlagen Nerven Musklen und Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41-4109 has multiple effects on Hepatitis B virus capsid assembly", Journal of Molecular Recognition, vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang, et al., "In vitro inhibition of HBV replication by a novel compound, GLS4, and its efficacy against adefovir-dopovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber et al., "Inhibition of Human Hepatitis B Virus (HBV) by a Novel Non-Nucleosidic Compound in a Transgenic Mouse Model", Antiviral Research, vol. 54: pp. 69-78 (2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-1302, (2011).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).
Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al., "NVR 3-778, a first-in-class HBV core inhibitor, alone and in combination with PEG-Interferon (PEGIFN), in treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zlotnick, et al., "Core Protein: A pleiotropic Keystone in the HBV Lifecycle", Antiviral Research, vol. 121: pp. 82-93 (2015).
Zoulim, et al., "Current Treatments for Chronic Hepatitis B Virus Infections", Current Opinion in Virology, vol. 18: pp. 109-116 (2016).
Berke et al, Capsid Assembly Modulators Have a Dual Mechanism of Action in Primary Human Hepatocytes infected with Hepatitis B Virus, Antimicrobial Agents and Chemotherapy, Mar. 16, 2017, e00560-17, vol. 61, issue 8.
Corcuera et al, Novel non-heteroarylpyrimidine (HAP) capsid assembly modifiers have a different mode of action from HAPs in vitro, Antiviral Research, Jul. 20, 2018, pp. 135-142, 158.
Diab, et al., "The diverse functions of the hepatitis B core/capsid protein (HBc) in the viral life cycle: Implications for the development of HBc-targeting antivirals", Antiviral Research, vol. 149; pp. 211-220 (2018).
Huber et al, Novel Hepatitis B Virus Capsid-Targeting Antiviral that Aggregates Core Particles and Inhibits Nuclear Entry of Viral Cores, ACS Infectious Diseases, Dec. 24, 2018, 8b00235, 10.1021.
Hughes, et al., "Hepatitis Delta Virus", The Lancet, vol. 378: pp. 73-85, (Jul. 2, 2011).
Sun, et al., "Stable HepG2- and Huh7-based human hepatoma cell lines for efficient regulated expression of infectious hepatitis B virus", Journal of Hepatology, vol. 45: pp. 636-645 (2006).
European Search Report dated Jul. 10, 2019 for EP Application No. 19158758.3 filed Feb. 22, 2019.
Cai, et al., "Identification of disubstituted sulfonamide compounds as specific inhibitors of hepatitis B virus covalently closed circular DNA formuation, Antimicrobial agents and chemotherapy" , pp. vol. 56(8): pp. 4277-4288 (May 29, 2012).
Ermann, et al., "Arylsulfonamide CB2 Receptor Agonists: SAR and Optimization of CB2 Selectivity", Bioorganic & Chemistry Letters, vol. 18: pp. 1725-1729 (2008).

(56) References Cited

OTHER PUBLICATIONS

Gent et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.

Hayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).

Mabrouk, "Discovering best candidates for Hepatocellular Carcinoma (HCC) by in-silico techniques and tools" Int. J. Bioinformatics Research and Applications, vol. 8 (112): pp. 141-152 (Jan. 1, 2012).

Mohebbi, et al., "An Overview of Hepatitis B Virus Surface Antigen Secretion Inhibitors", Frontier in Microbiology, vol. 9: pp. 1-0 (Apr. 2018).

Qiu, et al., "Design and Synthesis of Orally Bioavailabie 4-Methyl Heteroaryldihydropyrimidine Based Hepatitis B Virus (HBV) Capsid Inhibitors", Journal of Medicinal Chemistry, vol. 59: pp. 7651-7666, (2016).

Schroder, et al., "Arzneimittelchemie Passage", Arzneimittelchemei Grundlagen Nerveri Musklen und Gewebe, vol. XX (XX): pp. 30-33 (Jan. 1, 1976).

Wang, et al., "In vitro Inhibition of HBV replication by a novel compound, GLS4, and its efficacy against adefovir-dipovoxil-resistant HBV mutations", Antiviral Therapy, vol. 17:pp. 793-803 (2012).

Watanabe, et al, "Ortho lithlation of N,N-dimethylbenzenesulfunamide by n-butyllithium. Condensation with electrophilic compounds", Candian Journal of Chemistry, vol. 47: pp. 1543-1546 (Oct. 30, 1968).

AMIDE DERIVATIVES USEFUL IN THE TREATMENT OF HBV INFECTION OR HBV-INDUCED DISEASES

CROSS-REFERENCED APPLICATIONS

This application claims priority to European Patent Application No. 19159717.8, filed on Feb. 27, 2019, and European Patent Application No. 19158758.3, filed on Feb. 22, 2020, both of which are incorporated herein by reference.

FIELD

The application relates to amide derivatives, processes for their preparation, pharmaceutical compositions, and their uses, more particularly their uses in treating chronic hepatitis B virus (HBV) infection or HBV-induced diseases.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to sub-optimal treatment options and sustained rates of new infections in most parts of the developing world.

Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

The HBV capsid protein plays essential functions during the viral life cycle. HBV capsid/core proteins form meta-stable viral particles or protein shells that protect the viral genome during intercellular passage, and also play a central role in viral replication processes, including genome encapsidation, genome replication, and virion morphogenesis and egress.

Capsid structures also respond to environmental cues to allow un-coating after viral entry.

Consistently, the appropriate timing of capsid assembly and dis-assembly, the appropriate capsid stability and the function of core protein have been found to be critical for viral infectivity.

WO2015011281 (Janssen R&D Ireland) discloses glyoxamide substituted pyrrolamide derivatives, WO2017156255 (Emory University) discloses amide derivatives, and WO2018039531 (Gilead Sciences, Inc.) discloses substituted pyrrolizine derivatives as compounds active against HBV, There is a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates.

Particularly, it is desired to find compounds that are capable of capsid assembly modulation.

SUMMARY

The present invention is directed to compounds capable of capsid assembly modulation. The compounds of the present invention may provide a beneficial balance of properties with respect to prior art compounds. In particular, they may display a different profile, display improved solubility, and/or dose-proportional exposure. Thus, provided herein is a compound of formula (I)

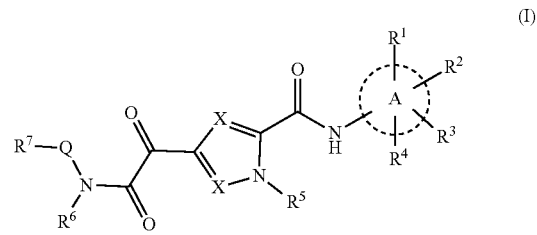

including the stereoisomers or tautomeric forms thereof, wherein:

represents a 6-membered aryl optionally containing one or more heteroatom(s), the heteroatom or each of the heteroatoms being nitrogen;

$R^1$, $R^2$ and $R^3$ are each independently selected from the group consisting of H, F, Cl, Br, $CHF_2$, $CH_2F$, $CF_3$, CN, $C_{1-4}$alkyl and $C_{3-6}$cycloalkyl;

$R^4$ is selected from the group consisting of H and F;

$R^5$ is selected from the group consisting of H, $C_{1-4}$alkyl, and $C_{3-6}$cycloalkyl;

Q is selected from the group consisting of $C_{2-5}$alkyl, optionally substituted with one or more substituents each independently selected from the group consisting of halo and $SO_2Me$, $C_{2-3}$alkenyl substituted with halogens and more particularly one or more fluorine, 3-6 membered monocyclic saturated rings, 3-9 membered polycyclic saturated rings, wherein the (3-6 membered monocyclic or 3-9 membered polycyclic) saturated rings:

optionally and independently contain one or more heteroatoms, the heteroatoms being each independently selected from N, O and S, and/or optionally and independently substituted with one or more substituents each independently selected from the group consisting of F, oxo, OH, C(=O)$NHCH_3$ and $C_{1-4}$alkyl optionally substituted with one or more fluoro;

$R^6$ is H;

$R^7$ is selected from the group consisting of phenyl, phenyl substituted with one or more substituents each independently selected from the group consisting of halo, CN, $CF_3$, $CF_2H$, $CH_2F$, $C_{1-4}$alkyl, $C_{3-6}$cycloalkyl, OH and $OC_{1-4}$alkyl, pyridyl, pyridyl substituted with one or more substituents each independently selected from the group consisting of halo, CN, $CF_3$, $CF_2H$, $CH_2F$, $C_{1-4}$alkyl, $C_{3-6}$cycloalkyl, OH and $OC_{1-4}$alkyl, pyrimidyl, pyrimidyl substituted with one or more substituents each independently selected from the group consisting of halo, CN, $CF_3$, $CF_2H$, $CH_2F$, $C_{1-4}$alkyl, $C_{3-6}$cycloalkyl, OH and $OC_{1-4}$alkyl, pyrazinyl, pyrazinyl substituted with one or more substituents each independently selected from the group consisting of halo, CN, $CF_3$, $CF_2H$, $CH_2F$, $C_{1-4}$alkyl, $C_{3-6}$cycloalkyl, OH and $OC_{1-4}$alkyl, pyridazinyl, pyridazinyl substituted with one or more substituents each independently selected from the group consisting of halo, CN, $CF_3$, $CF_2H$, $CH_2F$, $C_{1-4}$alkyl, $C_{3-6}$cycloalkyl, OH and $OC_{1-4}$alkyl, 5-membered unsaturated heterocycles containing one to 4 heteroatoms, the heteroatoms each being independently selected from N, O and S, and 5-membered unsaturated heterocycles containing one to 4 heteroatoms, the heteroatoms each being independently selected from N, O and S, substituted with one or more substituents each independently selected from the group consisting of halo, CN, $CF_3$, $CF_2H$, $CH_2F$, $C_{3-6}$cycloalkyl, OH and $OC_{1-4}$alkyl;

X is $CR^{8-}$, and $R^8$ is each independently selected from the group consisting of H, F, Cl, Br, CN, $OC_{1-4}$alkyl, $C_{3-6}$cycloalkyl, $C_{2-3}$alkenyl and $C_{1-4}$alkyl optionally substituted with one or more F and $OCH_3$, or a pharmaceutically acceptable salt thereof.

The application provides a pharmaceutical composition comprising at least one compound of Formula (I), or a pharmaceutically acceptable salt thereof, together with a pharmaceutically acceptable carrier.

The application provides a pharmaceutical composition comprising at least one disclosed compound, together with a pharmaceutically acceptable carrier. In another aspect, provided herein is a method of treating an HBV infection or an HBV-induced disease in an individual in need thereof, comprising administering to the individual a therapeutically effective amount of a compound of Formula (I) or a pharmaceutically acceptable salt thereof.

The application provides a product comprising a first compound and a second compound as a combined preparation for simultaneous, separate or sequential use in the prevention or treatment of an HBV infection or of an HBV-induced disease in mammal in need thereof, wherein said first compound is different from said second compound, wherein said first compound is a compound of Formula (I), or a pharmaceutically acceptable salt thereof, or the pharmaceutical composition described in the foregoing paragraph, and wherein said second compound is an HBV inhibitor.

The application provides a method of inhibiting or reducing the formation or presence of HBV DNA-containing particles or HBV RNA-containing particles in an individual in need thereof, comprising administering to the individual a therapeutically effective amount of a compound of Formula (I), or a pharmaceutically acceptable salt thereof.

Any of the methods provided herein can further comprise administering to the individual at least one additional therapeutic agent, more particularly at least one other HBV inhibitor.

DESCRIPTION

Provided herein are compounds, e.g., the compounds of formula (I), or pharmaceutically acceptable salts thereof, which are notably useful in the treatment or prevention of HBV infection or of an HBV-associated (or HBV-induced) condition or disease in a subject in need thereof.

Without being bound to any particular mechanism of action, these compounds are believed to modulate or disrupt HBV capsid assembly and other HBV core protein (HBc) functions necessary for HBV replication or the generation of infectious particles and/or may disrupt HBV capsid assembly leading to empty capsids with greatly reduced infectivity or replication capacity. In other words, the compounds provided herein may act as Capsid Assembly Modulators or core protein allosteric modulators (CpAMs).

The compounds provided herein have potent antiviral activity, and are believed to exhibit favorable metabolic properties, tissue distribution, safety and pharmaceutical profiles, and to be suitable for use in humans. Disclosed compounds may modulate (e.g., accelerate, delay, inhibit, disrupt or reduce) normal viral capsid assembly or disassembly, bind capsid or alter metabolism of cellular polyproteins and precursors. The modulation may occur when the capsid protein is mature, or during viral infectivity. Disclosed compounds can be used in methods of modulating the activity or properties of HBV cccDNA, or the generation or release of HBV RNA particles from within an infected cell.

A compound of the application may accelerate the kinetics of HBV capsid assembly, thereby preventing or competing with the encapsidation of the Pol-pgRNA complex and thus blocking the reverse transcription of the pgRNA. A compound of the application can be assessed e.g., by evaluating the capacity of the compound to induce or to not induce speckling of the Hepatitis B virus core protein (HBc).

HBc is a small protein of about 21 kDa, which forms the icosahedral capsid. HBc has been described e.g., in Diab et al. 2018 (Antiviral Research 149 (2018) 211-220).

Capsid assembly modulators may induce the formation of morphologically intact capsids or the formation of pleiomorphic noncapsid structures. Pleiomorphic non-capsid structures can be visualized in stable HBV-replicating cell lines by immunofluorescence staining against the HBV core protein and appear as "core speckling" in the nucleus and cytoplasm.

The term "HBc speckling" thus refers to the capacity of inducing the formation of such pleiomorphic noncapsid structures.

In an aspect, the application relates more particularly to a compound (as herein described), which does not induce speckling of HBc.

In another aspect, the application relates more particularly to a compound (as herein described), which induces speckling of HBc.

The capacity to induce or to not induce HBc speckling can be assessed by any means which the person of ordinary skill in the art finds appropriate, e.g., by:

contacting a compound of the application with HBV-infected cells (e.g., cells from a (stable) HBV-infected cell line or HBV infected cells which have been previously collected from an HBV patient);

optionally fixing and permeabilizing the cells, or optionally lysing the cells; and determining whether contacting of these cells with the compound of the application induces or does not induce HBc speckling in these cells.

Determining whether contacting of these cells with the compound of the application induces or does not induce HBc speckling can e.g., involve immunofluorescence staining against HBc, more particularly immunofluorescence staining against HBc with an anti-HBc antibody.

Examples of method to determine whether a compound of the application has or not the capacity to induce HBc speckling comprise the method described in the examples below, and the immunofluorescence assay described in Corcuera et al. 2018 (Antiviral Research (2018), doi/10.1016/j.antiviral.2018.07.011, *"Novel non-heteroarylpyrimidine (HAP) capsid assembly modifiers have a different mode of action from HAPs in vitro"*; cf. § 2.8 of Corcuera et al. 2018). FIG. 5 of Corcuera et al. 2018 illustrates HBV core morphology when a test compound induces HBc speckling (cf. the HAP-treated cells of FIG. 5) and when a test compound does not induce HBc speckling (cf. in FIG. 5, those cells which are treated with a CAM other than HAP).

Complementarily, confirmation that a compound is inducing the formation of pleiomorphic non-capsid structures or not can be obtained by implementing a cell-free biochemical assay using recombinant HBV core dimers (i.e., not using HBV-infected cells but using recombinant HBV core dimers) and using analytical size exclusion chromatography and electron microscopy analysis: cf. e.g., § 2.4-2.5 and FIGS. 2-3 of Corcuera et al. 2018; cf. e.g., Materials and Methods, as well as FIG. 2 of Berke et al. 2017 (Antimicrobial Agents and Chemotherapy August 2017 volume 61 Issue 8 e00560-17 *"Capsid Assembly Modulators have a dual mechanism of action in primary human hepatocytes infected with Hepatitis B virus"*); cf. e.g., the experimental section and FIG. 4 of Huber et al 2018 (ACS Infect Dis. 2018 Dec. 24. doi: 10.1021/acsinfecdis.8b00235; "Novel Hepatitis B Virus Capsid-Targeting Antiviral that Aggregates Core Particles and Inhibits Nuclear Entry of Viral Cores").

In an embodiment, the compounds described herein are suitable for monotherapy and are effective against natural or native HBV strains and against HBV strains resistant to currently known drugs. In another embodiment, the compounds described herein are suitable for use in combination therapy.

Listed below are definitions of various terms used to describe the subject matter of the application. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes", and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity or is lethal to the virus.

As used herein, the term "treatment" or "treating" is defined as the application or administration of a therapeutic agent, i.e., a disclosed compound (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the application include the conventional non-toxic salts of the parent compound formed, for example, from non-toxic inorganic or organic acids. The pharmaceutically acceptable salts of the application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, issue 1, pp 1-19 (1977), each of which is incorporated herein by reference in its entirety.

As used herein, the term "composition" or "pharmaceutical composition" refers to a mixture of at least one compound of the application with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound of the application within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound of the application, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar;

buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound of the application and are physiologically acceptable to the patient. Supplementary active compounds may also be incorporated into the compositions. Other additional ingredients that may be included in the pharmaceutical compositions of the application are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_3$alkyl or $C_{1-3}$ alkyl means an alkyl having one to three carbon atoms, $C_1$-$C_4$alkyl or $C_{1-4}$ alkyl means an alkyl having one to four carbon) and includes straight and branched chains. Examples include methyl, ethyl, propyl, isopropyl, butyl, isobutyl, tert-butyl. Embodiments of alkyl generally include, but are not limited to, $C_1$-$C_{10}$ alkyl, such as $C_1$-$C_6$ alkyl, such as $C_1$-$C_4$ alkyl.

As used herein, the term "alkenyl," by itself or as part of another substituent means, unless otherwise stated, a linear or branched chain of hydrocarbons comprising at least one carbon to carbon double bond, having the number of carbon atoms designated (i.e., $C_2$-C3 alkenyl or $C_{2-3}$alkenyl means an alkenyl having two to three carbon atoms, $C_2$-$C_4$ alkenyl or $C_{2-4}$alkenyl means an alkenyl having two to four carbon atoms. $C_4$-$C_8$ alkenyl or $C_{4-8}$alkenyl means an alkenyl having four to eight carbon atoms.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "saturated ring" refers to saturated rings optionally contain one or more heteroatoms, the heteroatoms being independently selected from N, O and S.

In the event that no such heteroatoms are present, the saturated ring is a cycloalkyl. The term "cycloalkyl" refers to a mono cyclic non-aromatic saturated radical, wherein each of the atoms forming the ring (i.e., skeletal atoms) is a carbon atom. $C_{3-6}$ cycloalkyl include groups having 3 to 6 ring atoms. Such 3- to 6-membered saturated rings include, but are not limited to, cyclopropyl, cyclobutyl, cyclopentyl and cyclohexyl.

In the event that the saturated ring contains one or more heteroatoms, these are independently selected from N, O and S. It will be understood by the skilled person that the one or more heteroatoms independently selected from N, O and S, will not be selected such as to provide a chemically non-existent structure. Generally, it will be understood that this refers to chemistry that would not be considered aberrant by the skilled person. E.g., the skilled person will be aware that, generally, in a single, 6-membered saturated ring, up to three nitrogen, oxygen, or sulfur atoms can be present. The skilled person will also be aware that, generally, in a single, five- or six-membered saturated ring, several combinations of two heteroatoms can be present, such as nitrogen/nitrogen, nitrogen/oxygen, sulfur/nitrogen, oxygen/oxygen, and sulfur/sulfur. Generally, no adjacent bonds are present selected from the group consisting of O—O, S—N, S—S, and O—S.

Examples of saturated rings include, but are not limited to heterocyclyl groups comprising one, two or three heteroatoms, even more in particular, one or two, and most particular, one heteroatom. Said ring heteroatoms are each selected from O, S, and N. In an embodiment, each heterocyclyl group has from 3 to 6 atoms in its ring system, with the proviso that the ring of said group does not contain two adjacent O or S atoms. The heterocyclyl group can be attached to the remainder of the molecule, unless otherwise stated, at any heteroatom or carbon atom that affords a stable structure.

An example of a 3-membered heterocyclyl group includes, and is not limited to, aziridine. Examples of 4-membered heterocyclyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups include monocyclic groups such as aziridine, oxirane, thiirane, azetidine, oxetane, thietane, pyrrolidine, pyrroline, pyrazolidine, imidazoline, dioxolane, sulfolane, tetrahydrofuran, thiophane, piperidine, piperazine, morpholine, thiomorpholine.

As used herein, the term "5-membered unsaturated heterocycles" refers to unsaturated rings, i.e. containing at least one double bond in the cyclic structure, containing one to 4 heteroatoms, the heteroatoms being independently selected from N, O and S. Such 5-membered unsaturated heterocycles refer therefore to heterocycles that are unsaturated and can have non-aromatic or aromatic character, with 5-membered unsaturated heterocycles having aromatic character (also referred to as heteroaryls) being preferred. Examples of 5-membered unsaturated heterocycles include, but are not limited to imidazole, tetrazole and triazole.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl or 6-membered aryl) and biphenyl (e.g., $C_{12}$-aryl). In some embodiments, aryl groups have from six to sixteen carbon atoms. In some embodiments, aryl groups have from six (also referred to as 6-membered aryl) to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. By the reference to the aromatic character, the skilled person is aware of the customary limitations to the number of ring atoms. Generally, heteroaryl substituents may be defined by the number of carbon atoms, e.g., $C_{1-12}$heteroaryl, such as $C_{3-9}$ indicates the number of carbon atoms contained in the heteroaryl group without including the number of heteroatoms.

For example, a $C_1$-$C_9$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic, such as bicyclic, heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

As used herein, the terminology "selected from . . . " (e.g., "$R^4$ is selected from A, B and C") is understood to be equivalent to the terminology "selected from the group consisting of . . . " (e.g., "$R^4$ is selected from the group consisting of A, B and C").

The application provides a compound of Formula (I):

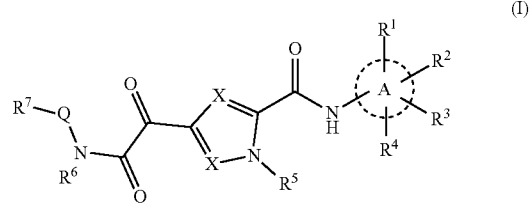

including the stereoisomers or tautomeric forms thereof, or a pharmaceutically acceptable salt thereof, wherein:

represents a 6-membered aryl optionally containing one or more heteroatom(s), the heteroatom or each of the heteroatoms being nitrogen;

$R^1$, $R^2$ and $R^3$ are each independently selected from the group consisting of H, F, Cl, Br, $CHF_2$, $CH_2F$, $CF_3$, CN, $C_{1-4}$alkyl and $C_{3-6}$cycloalkyl;

$R^4$ is selected from the group consisting of H and F;

$R^5$ is selected from the group consisting of H, $C_{1-4}$alkyl, and $C_{3-6}$cycloalkyl;

Q is selected from the group consisting of
- $C_{2-5}$alkyl, optionally substituted with one or more substituents selected from the group consisting of halogens and $SO_2Me$,
- $C_{2-3}$alkenyl substituted with halogens and more particularly one or more fluorine,
- 3-6 membered monocyclic saturated rings,
- 3-9 membered polycyclic saturated rings,
- wherein the (3-6 membered monocyclic or 3-9 membered polycyclic) saturated rings:
  - optionally (and independently) contain one or more heteroatoms, the heteroatoms being independently selected from N, O and S, and/or
  - are optionally (and independently) substituted with one or more substituents selected from the group consisting of F, oxo, OH, C(=O)NHCH$_3$ and C$_{1-4}$alkyl optionally substituted with one or more fluorine;

R$^6$ is H;

R$^7$ is selected from the group consisting of
phenyl,
phenyl substituted with one or more substituents selected from the group consisting of halogens, CN, CF$_3$, CF$_2$H, CH$_2$F, C$_{1-4}$alkyl, C$_{3-6}$cycloalkyl, OH and OC$_{1-4}$alkyl,
pyridyl,
pyridyl substituted with one or more substituents selected from the group consisting of halogens, CN, CF$_3$, CF$_2$H, CH$_2$F, C$_{1-4}$alkyl, C$_{3-6}$cycloalkyl, OH and OC$_{1-4}$alkyl,
pyrimidyl,
pyrimidyl substituted with one or more substituents selected from the group consisting of halogens, CN, CF$_3$, CF$_2$H, CH$_2$F, C$_{1-4}$alkyl, C$_{3-6}$cycloalkyl, OH and OC$_{1-4}$alkyl,
pyrazinyl,
pyrazinyl substituted with one or more substituents selected from the group consisting of halogens, CN, CF$_3$, CF$_2$H, CH$_2$F, C$_{1-4}$alkyl, C$_{3-6}$cycloalkyl, OH and OC$_{1-4}$alkyl,
pyridazinyl,
pyridazinyl substituted with one or more substituents selected from the group consisting of halogens, CN, CF$_3$, CF$_2$H, CH$_2$F, C$_{1-4}$alkyl, C$_{3-6}$cycloalkyl, OH and OC$_{1-4}$alkyl,
5-membered unsaturated heterocycles containing one to 4 heteroatoms, the heteroatoms being independently selected from N, O and S, and
5-membered unsaturated heterocycles containing one to 4 heteroatoms, the heteroatoms being independently selected from N, O and S, substituted with one or more substituents selected from the group consisting of halogens, CN, CF$_3$, CF$_2$H, CH$_2$F, C$_{1-4}$alkyl, C$_{3-6}$cycloalkyl, OH and OC$_{1-4}$alkyl;

X is CR$^8$, and

R$^8$ is selected from the group consisting of H, F, Cl, Br, CN, OC$_{1-4}$alkyl, C$_{3-6}$cycloalkyl, C$_{2-3}$alkenyl and C$_{1-4}$alkyl optionally substituted with one or more F and OCH$_3$.

In an embodiment of the compound of formula (I), Q is a 3-6 membered monocyclic saturated ring optionally containing one or more heteroatoms, the heteroatoms being each independently selected from N, O and S, and optionally substituted with one or more substituents each independently selected from the group consisting of F, oxo, OH, C(=O)NHCH$_3$, C$_{1-4}$alkyl, and C$_{1-4}$alkyl substituted with one or more fluoro.

In an embodiment of the compound of formula (I), Q is a 3-6 membered monocyclic saturated ring, more in particular, a 3-5 membered monocyclic saturated ring, optionally containing a O or S heteroatoms, and optionally substituted with one or more substituents each independently selected from the group consisting of F, oxo, OH, and C$_{1-4}$alkyl substituted with one or more fluoro.

In a yet further embodiment of the compound of formula (I), Q is selected from the group consisting of cyclopropyl, cyclobutyl, cyclopentyl, oxetanyl, and thietanyl, more in particular selected from cyclopropyl and cyclobutyl, each of which may be optionally substituted with one or more substituents each independently selected from the group consisting of F, oxo, OH, and C$_{1-4}$alkyl substituted with one or more fluoro.

In an embodiment of the compound of formula (I), R$^7$ is phenyl, or is a 5-membered unsaturated heterocycle containing one to 4 heteroatoms, the heteroatoms being each independently selected from N, O and S, and optionally substituted with one or more substituents each independently selected from the group consisting of halo, CN, CF$_3$, CF$_2$H, CHF$_2$, C$_{3-6}$cycloalkyl, OH and OC$_{1-4}$alkyl. Here too, the number and combinations of heteroatoms will be understood to not include chemistry that is aberrant, as discussed above. In particular, the substituents can be selected from halo, C$_{1-4}$alkyl, and C$_{3-6}$cycloalkyl, more in particular, C$_{1-4}$alkyl.

In an embodiment of the compound of formula (I), R$^7$ is a 5-membered unsaturated heterocycle containing one to 4 heteroatoms, the heteroatoms being each independently selected from N, O and S, and optionally substituted with one or more substituents each independently selected from the group consisting of halo, CN, CF$_3$, CF$_2$H, CHF$_2$, C$_{1-4}$alkyl, C$_{3-6}$cycloalkyl, OH and OC$_{1-4}$alkyl. Here too, the number and combinations of heteroatoms will be understood to not include chemistry that is aberrant, as discussed above.

In a further embodiment of the compound of formula (I), R$^7$ is a 5-membered unsaturated heterocycle containing one to 4 nitrogen atoms, in particular imidazolyl, triazolyl or tetrazolyl, and optionally being substituted with one or more substituents each independently selected from the group consisting of halo, C$_{1-4}$alkyl, and C$_{3-6}$cycloalkyl. More in particular, R$^7$ is selected from the group consisting of imidazolyl, triazolyl and tetrazolyl, each of which may be optionally substituted with one or two substituents, each independently selected from C$_{1-4}$alkyl.

In an embodiment of the compound of formula (I), each of R$^1$ and R$^2$ is H, R$^3$ is methyl, chloro or cyano, and R$^4$ is fluoro.

In an embodiment of the compound of formula (I),

represents phenyl carrying substituents in a meta position and in the para position, whereby one substituent is fluor and the other substituent is selected from the group consisting of fluor, chlorine, cyano, and methyl; or

represents pyridyl substituted with CHF$_2$.

In an embodiment of the compound of formula (I),

represents phenyl carrying substituents in a meta position and in the para position, whereby one substituent is fluoro and the other substituent is selected from the group consisting of fluoro, chloro, cyano, and methyl.

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl; Q is a 3-6 membered ring, in particular, a 3-5 membered ring, more in particular, cyclopropyl, cyclobutyl, oxetanyl, thietanyl, or cyclopentyl, each of which being optionally substituted with one or two substituents, each independently selected from the group consisting of F, oxo, OH, and CHF$_2$.

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl; in Q, the 3-6 membered ring is cyclobutyl, particularly cyclobutyl substituted with one or more fluoro, more particularly 3,3-difluorocyclobutyl.

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl; Q is a C$_{2-5}$alkyl optionally substituted with one or more halo substituents, in particular fluoro. More in particular, Q is selected from the group consisting of

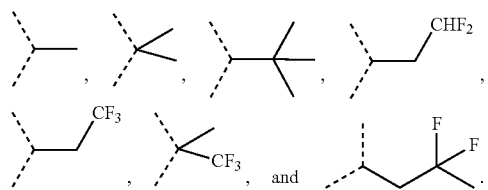

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl, Q is C$_{2-5}$alkyl, particularly ethyl or isopropyl.

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl, Q is:
  C$_{2-5}$alkyl, optionally substituted with one or more substituents each independently selected from the group consisting of halogens and SO$_2$Me, or
  3-6 membered monocyclic saturated rings, wherein the 3-6 membered monocyclic saturated rings:
    optionally (and independently) contain one or more heteroatoms, the heteroatoms being each independently selected from N, O and S, and/or
    optionally (and independently) substituted with one or more substituents each independently selected from the group consisting of F, oxo, OH, C(=O)NHCH$_3$ and C$_{1-4}$alkyl optionally substituted with one or more fluoro.

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl, Q is:
  C$_{2-5}$alkyl optionally substituted with one or more halo substituents, in particular fluoro, or
  a 3-6 membered ring, in particular, a 3-5 membered ring, more in particular, cyclopropyl, cyclobutyl, oxetanyl, thietanyl, or cyclopentyl, each of which being optionally substituted with one or two substituents, each independently selected from the group consisting of F, oxo, OH, and CHF$_2$.

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl, Q is:
  C$_{2-5}$alkyl optionally substituted with one or more halo substituents, in particular fluoro, or
  a 3-6 membered ring, in particular, a 3-5 membered ring, more in particular, cyclopropyl, cyclobutyl, oxetanyl, thietanyl, or cyclopentyl, each of which being optionally substituted with one or two substituents, each independently selected from the group consisting of F, oxo, OH, and CHF$_2$.

In an embodiment of the compound of formula (I), particularly wherein

represents phenyl carrying substituents in a meta position and in the para position, whereby one substituent is fluoro and the other substituent is selected from the group consisting of fluoro, chloro, cyano, and methyl, Q is:

C$_{2-5}$alkyl optionally substituted with one or more fluoro substituents, selected from the group consisting of

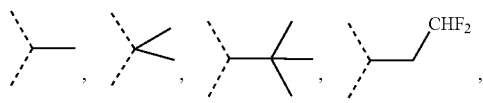

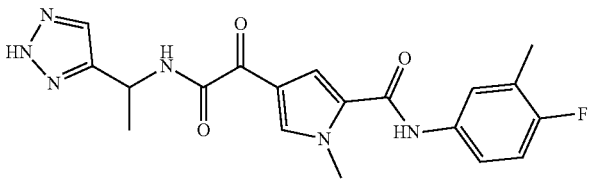 [SMILES: Cc1cc(NC(=O)c2cc(C(=O)C(=O)NC(C)c3cn[nH]n3)cn2C)ccc1F]

or
3,3-difluorocyclobutyl.

All combinations of the embodiments discussed hereinbefore or hereinafter are expressly included.

Compounds in accordance with the application include, but are not limited to compounds having the following formulae:

TABLE 1

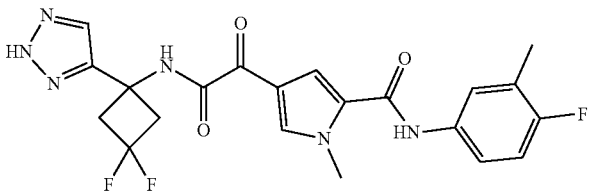 [SMILES: Cc1cc(NC(=O)c2cc(C(=O)C(=O)NC3(c4cn[nH]n4)CC(F)(F)C3)cn2C)ccc1F]

1

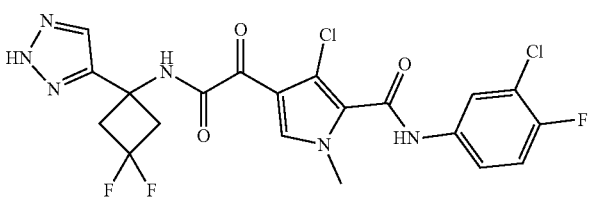 [SMILES: Cn1cc(C(=O)C(=O)NC2(c3cn[nH]n3)CC(F)(F)C2)c(Cl)c1C(=O)Nc1ccc(F)c(Cl)c1]

2

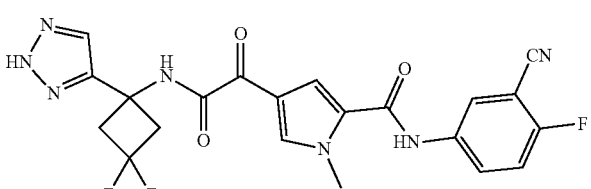

3

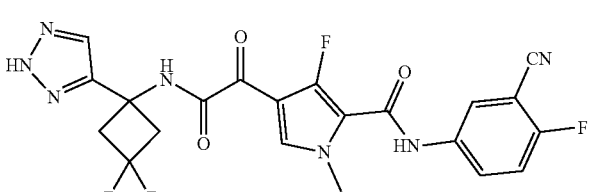

4

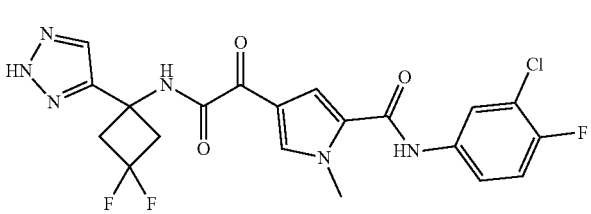 [SMILES: Cn1cc(C(=O)C(=O)NC2(c3cn[nH]n3)CC(F)(F)C2)cc1C(=O)Nc1ccc(F)c(Cl)c1]

5

6

TABLE 1-continued
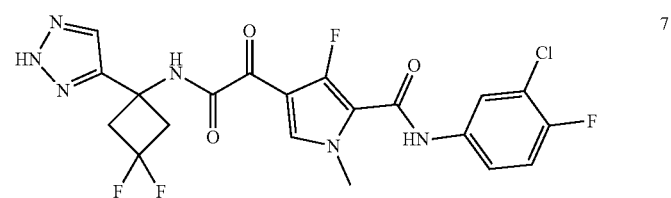
7
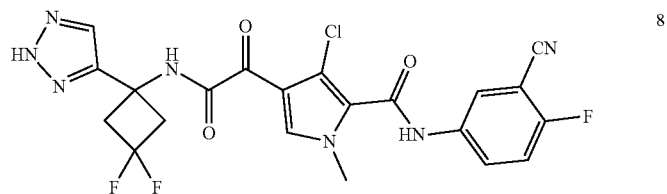
8
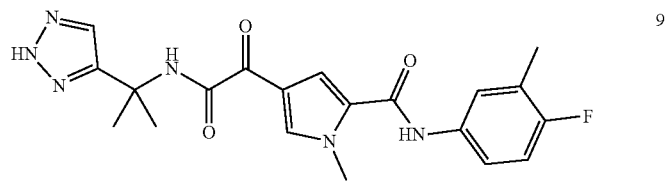
9
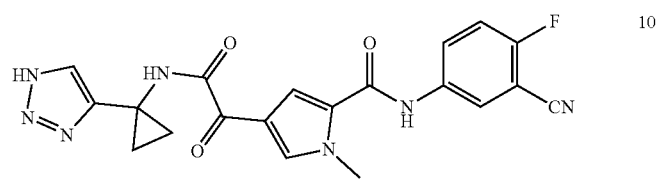
10
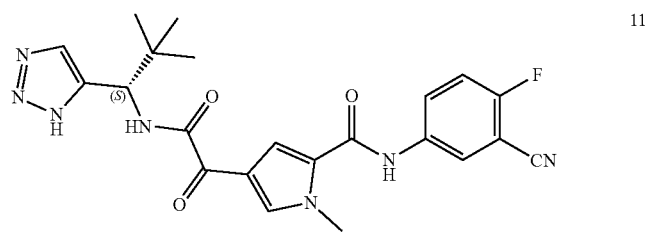
11
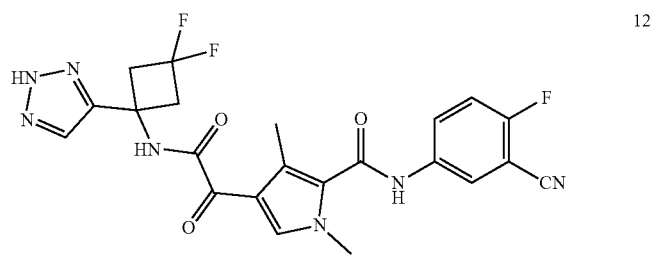
12
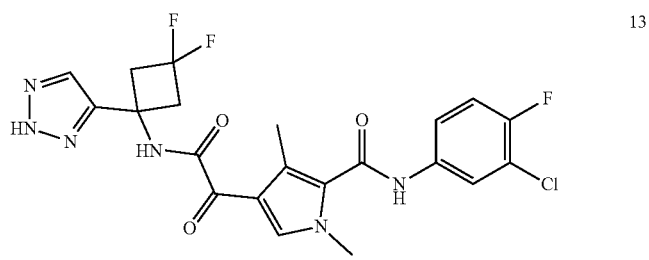
13

TABLE 1-continued

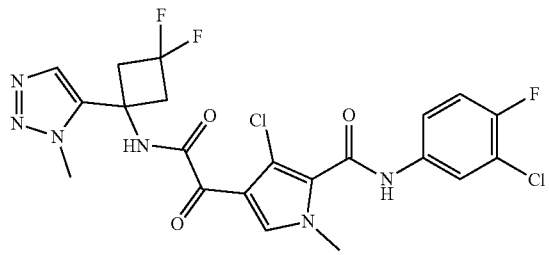 [SMILES: Cn1cc(C(=O)C(=O)NC2(c3cnnn3C)CC(F)(F)C2)c(Cl)c1C(=O)Nc1ccc(F)c(Cl)c1]

14

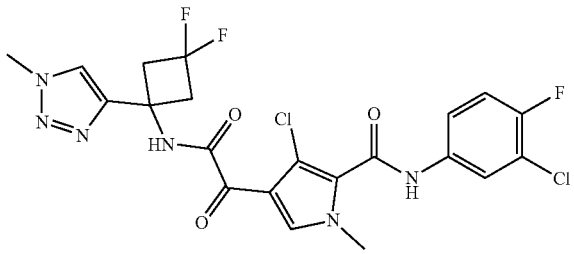 [SMILES: Cn1cc(C2(NC(=O)C(=O)c3cn(C)c(C(=O)Nc4ccc(F)c(Cl)c4)c3Cl)CC(F)(F)C2)nn1]

15

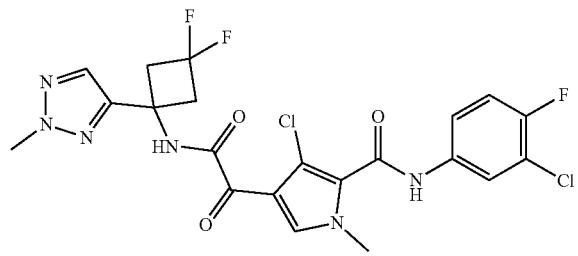 [SMILES: Cn1ncc(C2(NC(=O)C(=O)c3cn(C)c(C(=O)Nc4ccc(F)c(Cl)c4)c3Cl)CC(F)(F)C2)n1]

16

More particularly, compounds in accordance with the application include, but are not limited to compounds having the formula 1 or 2 (cf. Table 1 above).

More particularly, compounds in accordance with the application include, but are not limited to compounds having the following formula chosen from among formulas 1-8 and 12-16 (cf. Table 1 above), more particularly formulas 2-8 and 12-16.

More particularly, compounds in accordance with the application include, but are not limited to compounds having the following formula chosen from among formulas 1 and 9-11 (cf. Table 1 above).

The disclosed compounds may possess one or more stereocenters, and each stereocenter may exist independently in either R or S configuration. The absolute configuration is specified according to the Cahn-Ingold-Prelog system. Whenever the notation "RS" is indicated herein, it denotes that the compound is a racemic mixture, unless otherwise indicated. Whenever the notation "*RS" is indicated herein, it denotes that the compound is a racemic mixture of two enantiomers of cis or trans relative configuration (as further specified by the solid/hashed wedged bonds, wherein the solid/hashed wedged bonds have been assigned at random to indicate the cis of the trans diastereoisomer), e.g. 137 corresponds to a racemic mixture of two trans enantiomers. The stereochemical configuration may be assigned at indicated centers as (*R), (*S), (R*) or (S*) when the absolute stereochemistry is undetermined although the compound itself has been isolated as a single stereoisomer and is enantiomerically/diastereomerically pure. Compounds described herein are present in optically active or racemic forms. It is to be understood that the compounds described herein encompass racemic, optically-active, regioisomeric and stereoisomeric forms, or combinations thereof that possess the therapeutically useful properties described herein. When the absolute R or S stereochemistry of a compound cannot be determined, it can be identified by the retention time after chromatography under particular chromatographic conditions as determined by chromatographic column, eluent, etc.

A stereoisomeric form of a compound refers to all possible compounds made up of the same atoms bonded by the same sequence of bonds but having different three-dimensional structures which are not interchangeable.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. A mixture of one or more isomers can be utilized as the disclosed compound described herein. Compounds described herein may contain one or more chiral centers. These compounds can be prepared by any means, including stereoselective synthesis, enantioselective synthesis or separation of a mixture of enantiomers or diastereomers. Resolution of compounds and isomers thereof can be achieved by any means including, by way of non-limiting example, chemical processes, enzymatic processes, fractional crystallization, distillation, and chromatography.

The disclosed compounds may exist as tautomers. A "tautomer" refers to a proton-shift from one atom of the molecule to another atom of the same molecule. All tautomers are included within the scope of the compounds presented herein.

Compounds described herein also include isotopically-labeled compounds wherein one or more atoms are replaced by an atom having the same atomic number, but an atomic mass or mass number different from the atomic mass or mass number usually found in nature. Examples of isotopes suitable for inclusion in the compounds described herein include and are not limited to $^2$H, 3H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. Isotopically-labeled compounds can be useful in drug or substrate tissue distribution studies. Substitution with heavier isotopes such as deuterium may afford greater metabolic stability (which may lead to for example, increased in vivo half-life or reduced dosage requirements).

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds can be prepared by any suitable method or by processes using an appropriate isotopically-labeled reagent in place of the non-labeled reagent otherwise employed.

The compounds described herein may be labeled by other means, including, but not limited to, the use of chromophores or fluorescent moieties, bioluminescent labels, or chemiluminescent labels.

The compounds described herein, and other related compounds having different substituents can be synthesized using techniques and materials described herein and techniques known to the person of average skill in the art. General methods for the preparation of compounds as described herein can be modified by the use of appropriate reagents and conditions, for the introduction of the various moieties found in the formula as provided herein.

Compounds described herein can be synthesized using any suitable procedures starting from compounds that are available from commercial sources or are prepared using procedures described herein.

A compound of the application can be useful for reducing viral load associated with an HBV infection in an individual in need thereof, e.g., by administering to an individual in need thereof a therapeutically effective amount of a disclosed compound.

A compound of the application can be useful for reducing reoccurrence of an HBV infection in an individual in need thereof, e.g., by administering to an individual in need thereof a therapeutically effective amount of a disclosed compound.

A compound of the application can be useful for inhibiting or reducing the formation or presence of HBV DNA-containing particles or HBV RNA-containing particles in an individual in need thereof, e.g., by administering to the individual a therapeutically effective amount of a disclosed compound.

A compound of the application can be useful for reducing an adverse physiological impact of an HBV infection in an individual in need thereof, e.g., by administering to the individual a therapeutically effective amount of a disclosed compound.

A compound of the application can be useful for reducing, slowing, or inhibiting an HBV infection in an individual in need thereof, e.g., by administering to the individual a therapeutically effective amount of a disclosed compound.

A compound of the application can be useful for inducing reversal of hepatic injury from an HBV infection in an individual in need thereof, e.g., by administering to the individual a therapeutically effective amount of a disclosed compound.

A compound of the application can be useful for reducing the physiological impact of long-term antiviral therapy for HBV infection in an individual in need thereof, e.g., by administering to the individual a therapeutically effective amount of a disclosed compound.

A compound of the application can be useful for prophylactically treating an HBV infection in an individual in need thereof, wherein the individual is afflicted with a latent HBV infection, e.g., by administering to the individual a therapeutically effective amount of a disclosed compound.

A compound of the application can be useful for increasing or normalizing or restoring normal health, or eliciting full recovery of normal health, or restoring life expectancy, or resolving the viral infection in the individual in need thereof.

Where the invention is said to relate to the compound or composition according to the invention for use as a medicament, or or for use in the prevention or treatment of an HBV infection or HBV-induced disease in a mammal, in particular a human, it is understood that such compound or composition for use is to be interpreted in certain jurisdictions as a use of a compound or composition according to the invention for the manufacture of a medicament for e.g. the treatment or prevention in a subject, such as a mammal, in particular a human. The application relates to a pharmaceutical composition, which comprises at least one compound or pharmaceutically acceptable salt as herein described, and which further comprises at least one pharmaceutically acceptable carrier.

The application relates to such a compound or pharmaceutically acceptable salt, or to such a pharmaceutical composition, for use as a medicament.

The application relates to such a compound or pharmaceutically acceptable salt, or to such a pharmaceutical composition, for use in the prevention or treatment of an HBV infection or of an HBV-induced disease in mammal in need thereof.

The application relates to such a compound or pharmaceutically acceptable salt, or to such a pharmaceutical composition, for use in the prevention, the prevention of aggravation, the amelioration or the treatment of chronic Hepatitis B.

The application relates to such a compound or pharmaceutically acceptable salt, or to such a pharmaceutical composition, for use in the prevention, the prevention of aggravation, the amelioration or the treatment of a HBV-induced disease or condition.

The application relates to the use of such a compound or pharmaceutically acceptable salt, or to the use of such a pharmaceutical composition, for the manufacture of a medicament.

The application relates to the use of such a compound or pharmaceutically acceptable salt, or to the use of such a pharmaceutical composition, for the manufacture of a medicament for the prevention or treatment of an HBV infection or of an HBV-induced disease in mammal in need thereof.

The application relates to the use of such a compound or pharmaceutically acceptable salt, or to the use of such a pharmaceutical composition, for the manufacture of a medicament for the prevention, the prevention of aggravation, the amelioration or the treatment of chronic Hepatitis B.

The application relates to the use of such a compound or pharmaceutically acceptable salt, or to the use of such a pharmaceutical composition, for the manufacture of a medicament for the prevention, the prevention of aggravation, the amelioration or the treatment of a HBV-induced disease or condition.

HBV-induced disease or condition includes progressive liver fibrosis, inflammation and necrosis leading to cirrhosis, end-stage liver disease, and hepatocellular carcinoma. Additionally, HBV acts as a helper virus to hepatitis delta virus (HDV), and it is estimated that more than 15 million people may be HBV/HDV co-infected worldwide, with an increased risk of rapid progression to cirrhosis and increased hepatic decompensation, than patients suffering from HBV alone (Hughes, S. A. et al. Lancet 2011, 378, 73-85). HDV, infects therefore subjects suffering from HBV infection. In a particular embodiment, the compounds of the invention may be used in the treatment and/or prophylaxis of HBV/HDV co-infection, or diseases associated with HBV/HDV co infection. Therefore, in a particular embodiment, the HBV infection is in particular HBV/HDV co-infection, and the mammal, in particular the human, may be HBV/HDV co-infected, or be at risk of HBV/HDV co infection.

The application relates to such a compound or pharmaceutically acceptable salt, or to such a pharmaceutical composition, for any of the above-mentioned uses, more particularly for use in the prevention, the prevention of aggravation, the amelioration, or the treatment of one or more of the following items:

the prevention of chronic hepatis infection, more particularly chronic hepatis B infection (ie, preventing that the hepatitis (B) infection becomes chronic);

the amelioration or treatment of a hepatitis-associated or hepatitis-induced (chronic) disease or condition, more particularly of a hepatitis B-associated or hepatitis B-induced (chronic) disease or condition;

the prevention of the aggravation of a hepatitis-associated or hepatitis-induced (chronic) disease or condition, more particularly of a hepatitis B-associated or hepatitis B-induced (chronic) disease or condition;

the amelioration (regression, or absence of progression) of the stage of liver fibrosis, or of the extent of liver damage, induced by a (chronic) hepatitis infection, more particularly by a (chronic) hepatitis B infection;

the amelioration (reduction) of the fibrosis progression rate of a (chronic) hepatitis infection, more particularly the prevention of cirrhosis in a subject having a (chronic) hepatitis infection, more particularly by a (chronic) hepatitis B infection (e.g., preventing that the subject reaches the cirrhotic stage of fibrosis).

The compounds of the application may exist in unsolvated and solvated forms. The term "solvate" is used herein to describe a molecular complex comprising the compound of the application and one or more pharmaceutically acceptable solvent molecules, for example, ethanol.

The term "polymorph" refers to the ability of the compound of the application to exist in more than one form or crystal structure.

The compounds of the application may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the application or in combination with one or more other drugs. Generally, they will be administered as a formulation in association with one or more pharmaceutically acceptable excipients. The term "excipient" is used herein to describe any ingredient other than the compound(s) of the application. The choice of excipient depends largely on factors such as the particular mode of administration, the effect of the excipient on solubility and stability, and the nature of the dosage form.

The application also relates to a product comprising a first compound and a second compound as a combined preparation for simultaneous, separate or sequential use in the prevention or treatment of an HBV infection or of an HBV-induced disease in mammal in need thereof, wherein said first compound is different from said second compound, wherein said first compound is the compound or pharmaceutically acceptable salt as herein described, or the pharmaceutical composition of the application, and wherein said second compound is another HBV inhibitor.

For example, a second compound is another HBV inhibitor which is selected from the group consisting HBV combination drugs, HBV DNA polymerase inhibitors, immunomodulators, toll-like (TLR) receptor modulators, interferon alpha receptor ligands, hyaluronidase inhibitors, hepatitis b surface antigen (HbsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (P13K) inhibitors, indole amine 2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs. The compounds of the application or any subgroup thereof may be formulated into various pharmaceutical forms for administration purposes. As appropriate compositions there may be cited all compositions usually employed for systemically administering drugs. To prepare the pharmaceutical compositions of the application, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the application may also be administered via inhalation or insufflation by means of methods and formulations employed in the art for administration via this way. Thus, in general the compounds of the application may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general, it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the application. The effective amount ranges mentioned above are therefore only guidelines and are not intended to limit the scope or use of the application to any extent.

In the preparation of the compounds several intermediate compounds can be used. In this respect an aspect of this disclosure relates to compounds having the following formula II:

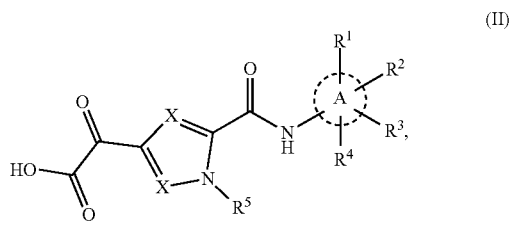

(II)

wherein $R^1$, $R^2$, $R^3$, $R^4$, $R^5$ and X have the abovementioned meaning.

In preparing the compounds the intermediate of formula (II) can be reacted, e.g., with an intermediate of formula (III):

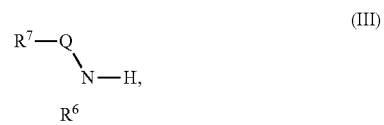

(III)

wherein $R^6$, $R^7$ and Q have the abovementioned meaning.

Intermediates in accordance with the present disclosure include but are not limited to intermediate compounds having the formulae shown in the synthesis examples given below.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited. The term "essentially consisting of" is a partially open term, which does not exclude additional, unrecited element(s), step(s), or ingredient(s), as long as these additional element(s), step(s) or ingredient(s) do not materially affect the basic and novel properties of the subject matter of the application.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

In an attempt to help the reader of the present application, the description has been separated in various paragraphs or sections. These separations should not be considered as disconnecting the substance of a paragraph or section from the substance of another paragraph or section. To the contrary, the present description encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Exemplary compounds useful in methods of the application will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

1. General Information
1.1. General Procedure for LCMS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). All results were obtained with experimental uncertainties that are commonly associated with the method used. Hereinafter, "BPR" means back pressure regulator, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-T of" Quadrupole Time-of-flight mass spectrometers, "CLND", ChemiLuminescent Nitrogen Detector, "ELSD" Evaporative Light Scanning Detector.

LCMS/SFC Methods (Flow expressed in mL/min; column temperature (T) in ° C.; Run time in minutes).

TABLE 2a

| LCMS Method Code | Instrument | Column | Mobile phase | Gradient | Flow Col T | Run time |
|---|---|---|---|---|---|---|
| A | Waters: Acquity ® UPLC ® - DAD and SQD | Waters: BEH C18 (1.7 µm, 2.1*50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 55 | 2 |
| B | Waters: Acquity ® UPLC ® - DAD, SQD and ELSD | Waters: HSS T3 (1.8 µm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.6 55 | 3.5 |
| C | Waters: Acquity ® UPLC ® - DAD and SQD | Waters: BEH (1.8 µm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.6 55 | 3.5 |
| D | Waters: Acquity ® UPLC ® - DAD and SQD | Waters: BEH (1.8 µm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 55 | 3.5 |
| E | Waters: Acquity ® UPLC ® - DAD and SQD | Waters: BEH (1.8 µm, 2.1*100 mm) | A: 0.1% $NH_4HCO_3$ in 95% $H_2O$ + 5% $CH_3CN$ B: MeOH | From 100% A to 5% A in 2.10 min, to 0% A in 0.9 min, to 5% A in 0.5 min | 0.6 55 | 5.5 |
| F | Thermoscientific Ultimate 3000 DAD and Brucker HCT ultra | Agilent: Poroshell EC-C18 (4 µm, 4.6 × 100 mm) | A: $HCO_2H$ 0.1% in water/ B: HCOOH 0.05% in $CH_3CN$ | 98% A for 2 min, to 0% A in 10 min, held for 3.4 min, back to 98% A in 1.3 min, held for 1.7 min | 1 30 | 18.4 |

TABLE 2b

| SFC Method code | Column | Mobile phase | Gradient | Flow Col T | Run time BPR |
|---|---|---|---|---|---|
| SFC_A | Daicel Chiralpak ® AD-H column (3.0 µm, 150 × 4.6 mm) | A: $CO_2$ B: EtOH + 0.2% $iPrNH_2$ | 10%-50% B in 6 min, hold 3.5 min | 2.5 40 | 9.5 110 |

TABLE 2b-continued

| SFC Method code | Column | Mobile phase | Gradient | Flow Col T | Run time BPR |
|---|---|---|---|---|---|
| SFC_B | Daicel Chiralpak® AD-H column (3.0 µm, 150 × 4.6 mm) | A: $CO_2$ B: iPrOH + 0.2% iPrNH$_2$ | 10%-50% B in 6 min, hold 3.5 min | 2.5 40 | 9.5 110 |
| SFC_C | Daicel Chiralpak® OJ3 column (3.0 µm, 150 × 4.6 mm) | A: $CO_2$ B: EtOH + 0.2% iPrNH$_2$ | 10%-50% B in 6 min, hold 3.5 min | 2.5 40 | 9.5 130 |
| SFC_D | Daicel Chiralpak® IG3 column (3.0 µm, 150 × 4.6 mm) | A: $CO_2$ B: EtOH + 0.2% iPrNH$_2$ | 10%-50% B in 6 min, hold 3.5 min | 2.5 40 | 9.5 130 |
| SFC_E | Daicel Chiralpak® IG3 column (3.0 µm, 150 × 4.6 mm) | A: $CO_2$ B: MeOH-iPrOH (50-50) + 0.2% iPrNH$_2$ | 10%-50% B in 6 min, hold 3.5 min | 2.5 40 | 9.5 130 |
| SFC_F | Daicel Chiralpak® IG3 column (3.0 µm, 150 × 4.6 mm) | A: $CO_2$ B: MeOH + 0.2% iPrNH$_2$ | 10%-50% B in 6 min, hold 3.5 min | 2.5 40 | 9.5 130 |
| SFC_G | Daicel Chiralpak® IG3 column (3.0 µm, 150 × 4.6 mm) | A: $CO_2$ B: iPrOH + 0.2% iPrNH$_2$ | 10%-50% B in 6 min, hold 3.5 min | 2.5 40 | 9.5 130 |
| SFC_H | Daicel Chiralpak® IC3 column (3.0 µm, 150 × 4.6 mm) | A: $CO_2$ B: EtOH + 0.2% iPrNH$_2$ | 10%-50% B in 6 min, hold 3.5 min | 2.5 40 | 9.5 130 |

1.2. NMR Analysis $^1$H NMR spectra were recorded on 1) a Bruker DPX 400 MHz spectrometer or 2) a Bruker Avance 400 MHz spectrometer or c) Bruker Avance III 400 MHz spectrometer or d) Bruker Avance 600 MHz spectrometer.

NMR spectra were recorded at ambient temperature unless otherwise stated. Data are reported as follow: chemical shift in parts per million (ppm) relative to TMS (δ=0 ppm) on the scale, integration, multiplicity (s=singlet, d=doublet, t=triplet, q=quartet, quin=quintuplet, sext=sextuplet, sept=septuplet, m=multiplet, b=broad, or a combination of these), coupling constant(s) J in Hertz (Hz).

2. Abbreviations

TABLE 3

| | |
|---|---|
| ACN | Acetonitrile |
| Aq. | Aqueous |
| DCM | Dichloromethane |
| DIPE | Diisopropylether |
| DIPEA | N,N-Diisopropylethylamine |
| DMF | N,N-Dimethylformamide |
| DMI | 1,3-Dimethyl-2-imidazolidinone |
| DMSO-d$_6$ | Hexadeuterodimethyl sulfoxide |
| EtOAc | Ethyl acetate |
| EtOH | Ethanol |
| h | Hour(s) |
| HATU | 1-[Bis(dimethylamino)methylene]-1H-1,2,3-triazolo[4,5-b]pyridinium 3-oxid hexafluorophosphate |
| HPLC | High Performance Liquid Chromatography |
| iPr | Isopropyl |
| LCMS | Liquid Chromatography Mass Spectrometry |
| LiHMDS | Lithium bis(trimethylsilyl)amide |
| MeOH | Methanol |
| MeTHF | 2 Me-Tetrahydrofuran |
| Min. | Minutes |
| Molec. Siev. | Molecular sieve |
| NBS | N-Bromosuccinimide |
| NCS | N-Chlorosuccinimide |
| NMR | Nuclear Magnetic Resonance |
| o/n | Overnight |
| PE | Petroleum ether |
| rm | Reaction mixture |
| RT | Room temperature |
| rt | Retention time |
| Sat. | Saturated |
| SFC | Supercritical Fluid Chromatography |
| SiliaMetS® TAAcONa | Si-triamine tetraacetic acid sodium salt |
| TFAA | Trifluoroacetic anhydride |
| THF | Tetrahydrofuran |
| TLC | Thin Layer Chromatography |
| MW | Microwave |

3. Procedures

Synthesis of Intermediates

Synthesis of Intermediate I4c

Step 1

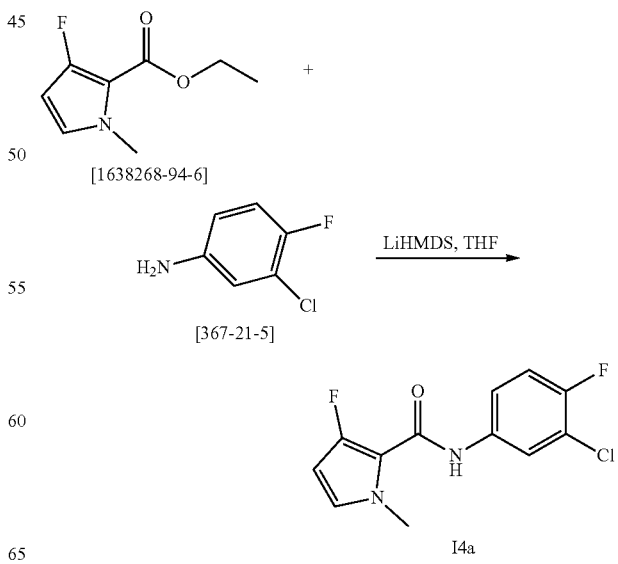

Ethyl 3-fluoro-1-methyl-1H-pyrrole-2-carboxylate (5 g, 29.21 mmol) was dissolved in THF (dried on molecular sieves) (80 mL). This mixture was cooled in an ice-bath and 3-chloro-4-fluoroaniline (4.7 g, 32.1 mmol) was added. Lithium bis(trimethylsilyl)amide (1 M in toluene) (58.4 mL, 58.4 mmol) was added drop wise over a period of 10 minutes. The ice bath was removed and the mixture was stirred for 1 hour at room temperature. The mixture was quenched with saturated ammonium chloride (150 mL) and the resulting mixture was extracted using EtOAc (3×150 mL). The combined extracts were washed with brine (200 mL), dried on $Na_2SO_4$, filtered and concentrated in vacuo to yield N-(3-chloro-4-fluorophenyl)-3-fluoro-1-methyl-1H-pyrrole-2-carboxamide (7.3 g, yield 83%) as a beige solid which was used as such in the next step.

Step 2

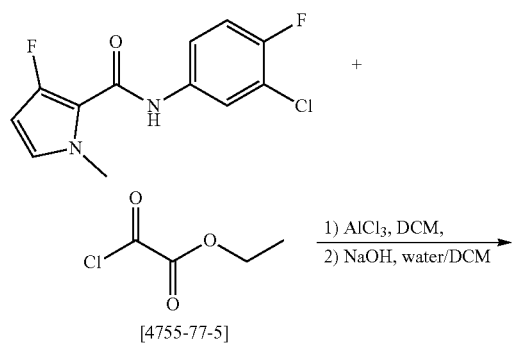

[4755-77-5]

1) $AlCl_3$, DCM,
2) NaOH, water/DCM

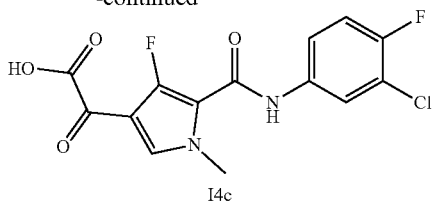

I4c

N-(3-chloro-4-fluorophenyl)-3-fluoro-1-methyl-1H-pyrrole-2-carboxamide was dissolved in DCM (on molec. siev.) (37 mL) and cooled on a water/ice bath under a gentle flow of nitrogen. A solution of ethyl oxalyl chloride (2.07 mL, 18.5 mmol) in DCM (on molec. siev.) (18.7 mL) was added dropwise and the mixture was stirred for 10 min. Aluminium trichloride (2.95 g, 22.2 mmol) was added in portions over 10 minutes and the mixture was stirred at 0° C. for 90 minutes. The resulting mixture was poured out into 100 mL ice-water, extract with EtOAc (2×). The combined extracts were washed with brine and evaporated to dryness affording intermediate I4b. The residue was taken up in 20 mL EtOH and NaOH (1 M in $H_2O$) (11.87 mL, 11.9 mmol) was added and the mixture was stirred at room temperature for 40 min. The mixture was cooled on ice, 40 ml water and then, conc HCl was added until complete precipitation (pH=1)

The precipitate was filtered off, washed with water and dried overnight in vacuum yielding 2-(5-((3-chloro-4-fluorophenyl)carbamoyl)-4-fluoro-1-methyl-1H-pyrrol-3-yl)-2-oxoacetic acid intermediate I4c (2.5 g, yield 85%) as a solid which was used as such.

Unless otherwise indicated, the intermediates below were synthetized following the procedure reported for intermediate I4a-c

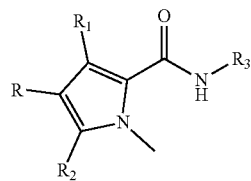

R = I
Ixa

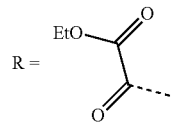
Ixb

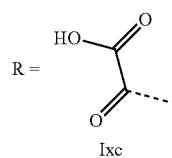
Ixc

| Intermediate | Structure | Reagents step 1 |
|---|---|---|
| I5a-c | ![structure] | ![reagents] [1478503-37-5] [367-21-5] |
| I6a-c | ![structure] | ![reagents] [1638268-94-6] [53312-81-5] |

-continued

| Intermediate | Structure | Reagents step 1 | |
|---|---|---|---|
| I7a-c | R-pyrrole-C(O)NH-(4-F,3-CN-phenyl), N-Me | methyl 1-methyl-1H-pyrrole-2-carboxylate [37619-24-2] | 4-fluoro-3-cyanoaniline [53312-81-5] |
| I8a-c | R-pyrrole-C(O)NH-(4-F,3-Cl-phenyl), N-Me | methyl 1-methyl-1H-pyrrole-2-carboxylate [37619-24-2] | 4-fluoro-3-chloroaniline [367-21-5] |
| I9a-c* | 3-Me, R-pyrrole-C(O)NH-(4-F,3-CN-phenyl), N-Me | methyl 1,3-dimethyl-1H-pyrrole-2-carboxylate [937688-38-5] | [53312-81-5] |
| I10a-c* | 3-Me, R-pyrrole-C(O)NH-(4-F,3-Cl-phenyl), N-Me | [937688-38-5] | [367-21-5] |
| I11a-c | 3-Br, R-pyrrole-C(O)NH-(4-F,3-CN-phenyl), N-Me | methyl 3-bromo-1-methyl-1H-pyrrole-2-carboxylate [1097834-91-7] | [53312-81-5] |
| I12a-c** | 3-OMe, R-pyrrole-C(O)NH-(4-F,3-CN-phenyl), N-Me | methyl 3-methoxy-1-methyl-1H-pyrrole-2-carboxylate [182818-89-9] | [53312-81-5] |

R = I (Ixa); R = C(O)C(O)OEt (Ixb); R = C(O)C(O)OH (Ixc)

-continued

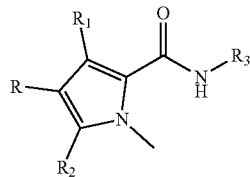

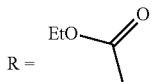
R = I
Ixa

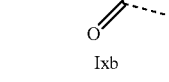
Ixb

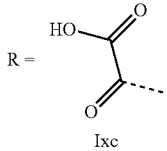
Ixc

| Intermediate | Structure | Reagents step 1 | |
|---|---|---|---|
| I13a-c | (3-methyl-1-methyl-pyrrole-2-carboxamide with 4-fluoro-3-bromoaniline) | [937688-38-5] | [656-64-4] |
| I14a-c* | (3,5-dimethyl-1-methyl-pyrrole-2-carboxamide with 4-fluoro-3-cyanoaniline) | [55770-79-1] | [53312-81-5] |
| I15a-c | (5-methyl-1-methyl-pyrrole-2-carboxamide with 4-fluoro-3-cyanoaniline) | [73476-31-0] | [53312-81-5] |
| I39a-c | (3-chloro-1-methyl-pyrrole-2-carboxamide with 4-fluoro-3-cyanoaniline) | [1478503-37-5] | [53312-81-5] |

*Step 1: MeTHF and LiHMDS (1.0M in THF) were used

**Step 1: another method was used: To a solution of 5-amino-2-fluorobenzonitrile (997 mg, 7.32 mmol) in toluene (5.2 mL) was added trimethylaluminum solution (2M in toluene) (3.66 mL, 7.32 mmol) dropwise at room temperature and the reaction mixture 5 was stirred for 5 minutes. A solution of methyl 3-methoxy-1-methyl-1H-pyrrole-2-carboxylate (826 mg, 4.88 mmol) in toluene (19 mL) was added and the reaction mixture was stirred overnight at 80° C.. The reaction mixture was cooled to room temperature, $Na_2SO_4$ decahydrate (500 mg) was added and the reaction mixture was stirred for 30 minutes. Then the reaction mixture was dried over $Na_2SO_4$, filtered and concentrated 10 under vacuum. The residue was purified by silica column chromatography (cyclohexane/EtOAc from 85/15 to 75/25) to afford N-(3-cyano-4-fluorophenyl)-3methoxy-1-methyl-1H-pyrrole-2-carboxamide intermediate 12a (1.11 g, 83% yield).

Synthesis of Intermediate I16c

Step 1

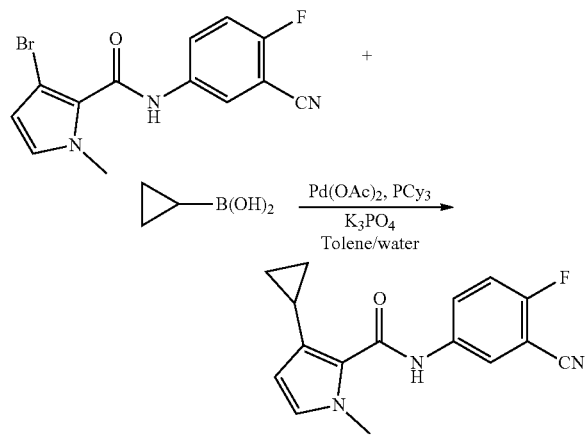

A 3 necked round bottom flask was charged with intermediate I11a (700 mg, 2.17 mmol), cyclopropylboronic acid (279 mg, 3.26 mmol), tricyclohexylphosphine (182.81 mg, 0.65 mmol), palladium acetate (73.18 mg, 0.326 mmol) and potassium phosphate tribasic (1.62 g, 7.61 mmol). The flask was evacuated under vacuum and backfilled with $N_2$. Toluene (43 mL) and water (1.5 mL) were added and a gentle flow of $N_2$ (bubbling) was performed during 5 min. The reaction and then the mixture suspension was stirred and heated at 100° C. After 24 h, TLC and LCMS showed the presence of the desired product as well as still some SM. The reaction was left overnight at 100° C. (48 h in total).

The reaction mixture was quenched with water and then extracted with EtOAc (3×). Organic phases were combined, dried over $MgSO_4$ and concentrated. The residue was then purified by silica column chromatography (heptane/EtOAc 70/30) to afford the desired product N-(3-cyano-4-fluorophenyl)-3-cyclopropyl-1-methyl-1H-pyrrole-2-carboxamide (208 mg, 34% yield) as a white solid.

Step 2

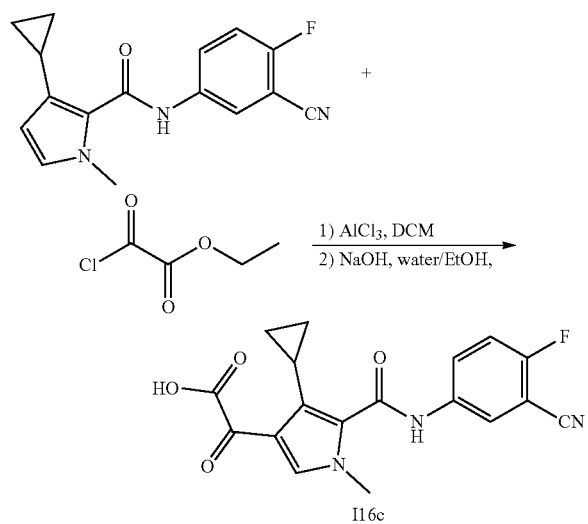

N-(3-cyano-4-fluorophenyl)-3-cyclopropyl-1-methyl-1H-pyrrole-2-carboxamide was dissolved in DCM (4 mL) and cooled on a water/ice bath under a gentle flow of nitrogen. A solution of ethyl oxalyl chloride (0.18 mL, 1.59 mmol) DCM (2 mL) was added dropwise and the mixture was stirred for 10 min. Aluminum chloride (254 mg, 1.91 mmol) was added in portions over 10 minutes and the mixture was stirred at 0° C. for 2 h. After 4 h, LCMS showed the formation of the desired product but there is still some starting material left. The reaction mixture was stirred at room temperature overnight.

The reaction mixture was poured out into 100 mL ice-water, extracted with EtOAc (2×150 mL). The combined extracts were washed with brine and evaporated to dryness. The residue was taken up in 4 ml EtOH and NaOH (1 M in $H_2O$, 3.8 mL, 3.81 mmol) was added and the mixture was stirred at room temperature for 1 h. Ice, then water (14 mL) and then conc. HCl were added until complete precipitation (pH=1). The precipitate was filtered off, washed with water (20 mL) and diethyl ether (2 mL) and dried overnight in vacuum oven yielding of intermediate I16c (154 mg, yield: 68%) as a pale beige solid.

Synthesis of Intermediate I17c

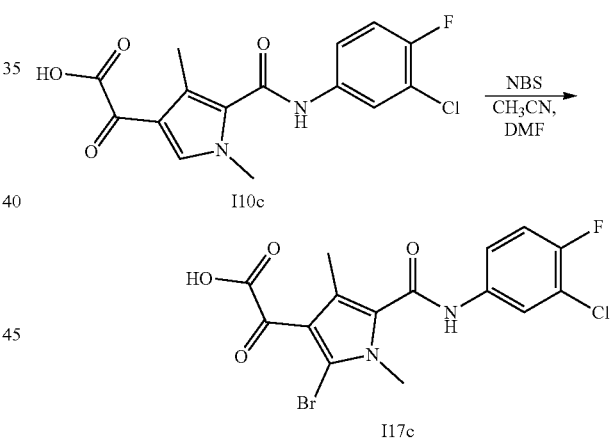

Intermediate I10c (1 g, 2.89 mmol) was dissolved in $CH_3CN$ (20 mL) and DMF (10 mL). NBS (772 mg, 4.34 mmol) was added at 0° C. After one night at room temperature, some starting material was remaining.

At 0° C., extra NBS (50 mg) was added and then the reaction mixture was stirred at room temperature another night. The mixture was treated with aqueous sat. $Na_2S_2O_3$ and aqueous sat. $NaHCO_3$ and extracted with ethyl acetate. The desired fractions were separated, dried over $MgSO_4$, filtered and concentrated under reduced pressure. The crude product was purified on silica column chromatography (DCM/2% HCOOH in MeOH 100/0 to 90/10) to afford intermediate I17c (2 g, mixture 66/23 desired product/starting material).

Synthesis of Intermediate I18b

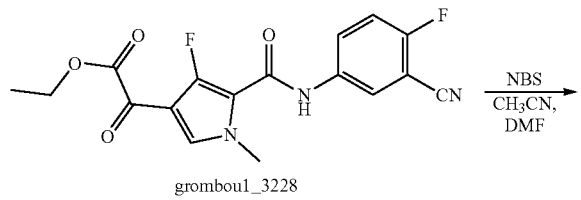
gromboul_3228

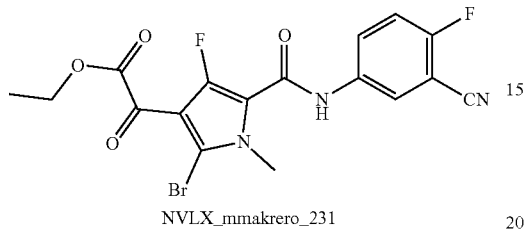
NVLX_mmakrero_231

To a solution of intermediate I6c (1.10 g, 3.05 mmol) in a mixture of CH$_3$CN (60 mL) and DMF (18 mL) was added NBS (1.08 g, 6.09 mmol). The reaction mixture was stirred at room temperature for 3 h. Acetonitrile was evaporated under reduced pressure and water (20 mL) and EtOAc (20 mL) were added. The layers were separated and the aqueous layer was extracted with EtOAc (3×50 mL).

The combined organic layers were dried over Na$_2$SO$_4$, filtered and concentrated under reduced pressure. The crude was purified on silica column chromatography (cyclohexane/EtOAc 100/0 to 56/44) to afford intermediate I18b (805 mg, 60% yield) as a white solid.

Synthesis of Intermediate I19c

Step 1

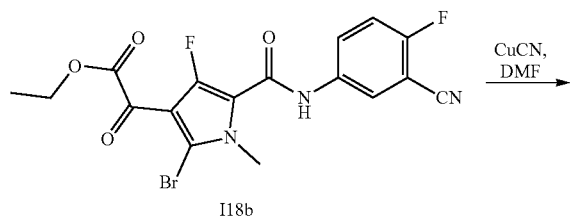
I18b

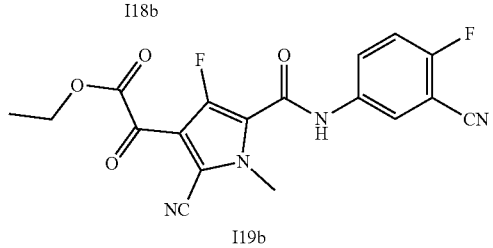
I19b

Copper cyanide (94.3 mg, 1.05 mmol) was added to a solution of intermediate I18b (309 mg, 0.702 mmol) in DMF (15 mL). The reaction mixture was heated under microwave conditions at 160° C. for 30 minutes then cooled down to RT and concentrated under reduced pressure. The residue was taken up in EtOAc (40 mL) and water (40 mL) then aqueous ammonia 33% (about 10 drops) was added. The layers were separated and the aqueous layer was extracted with EtOAc (20 mL). The combined organic layers were dried over Na$_2$SO$_4$, filtered and concentrated. The crude mixture was purified by silica column chromatography (cyclohexane/EtOAc: 90/10 to 60/40) to afford ethyl 2-(2-cyano-5-((3-cyano-4-fluorophenyl)carbamoyl)-4-fluoro-1-methyl-1H-pyrrol-3-yl)-2-oxoacetate (121 mg, 37% yield) as beige solid.

Step 2

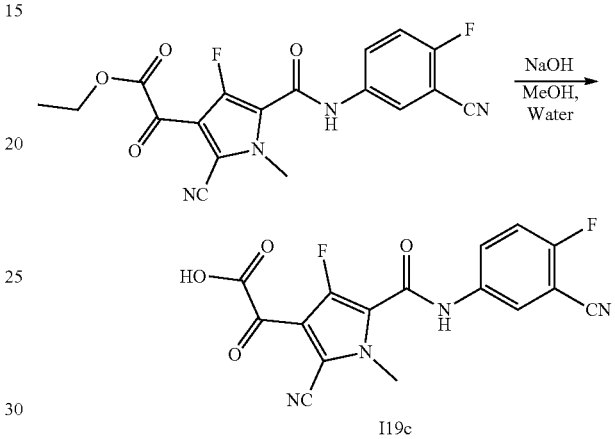
I19c

To a solution of ethyl 2-(2-cyano-5-((3-cyano-4-fluorophenyl)carbamoyl)-4-fluoro-1-methyl-1H-pyrrol-3-yl)-2-oxoacetate (110 mg, 0.285 mmol) in a mixture of water (0.8 mL) and methanol (0.8 mL) was added NaOH (0.85 mL, 1 M in water, 0.85 mmol) and the reaction mixture was stirred for 2 h at room temperature. Methanol was removed and the residue was diluted in water (15 mL). The aqueous layer was washed with EtOAc (15 mL). Then the aqueous layer was acidified with an aqueous solution of HCl 1 M until pH-1 and extracted with EtOAc (2×20 mL). The combined organic layers were dried over Na$_2$SO$_4$, filtered and concentrated to afford intermediate I19c (51 mg, 43% yield) as a white solid.

Synthesis of Intermediate I20c

Step 1

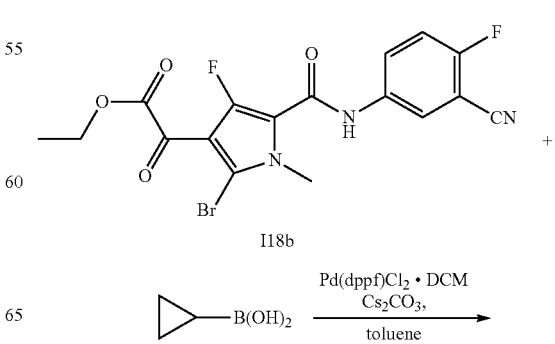

-continued

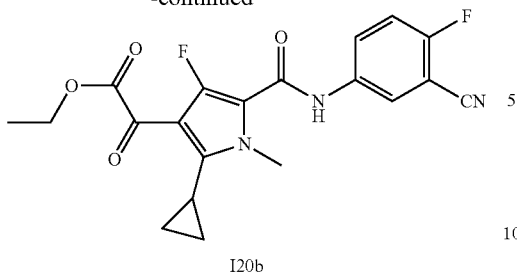

I20b

To a solution of intermediate I18b (400 mg, 0.909 mmol) in toluene (25 mL) were added cyclopropyl boronic acid (156 mg, 1.82 mmol), cesium carbonate (296 mg, 0.909 mmol) and Pd(dppf)Cl$_2$.DCM (74.2 mg, 0.091 mmol). The resulting mixture was stirred at 100° C. for 16 h. Water (30 mL) was added and the aqueous layer was extracted with EtOAc (3×20 mL) and the combined organic layers were washed with brine (30 mL), dried over Na$_2$SO$_4$, filtered and concentrated under reduced pressure. The crude was purified on silica column chromatography (cyclohexane/EtOAc from 100/0 to 60/40) to afford ethyl 2-(5-((3-cyano-4-fluorophenylcarbamoyl)-2-cyclopropyl-4-fluoro-1-methyl-1H-pyrrol-3yl)-2-oxoacetate (342 mg, 70% yield).

Step 2

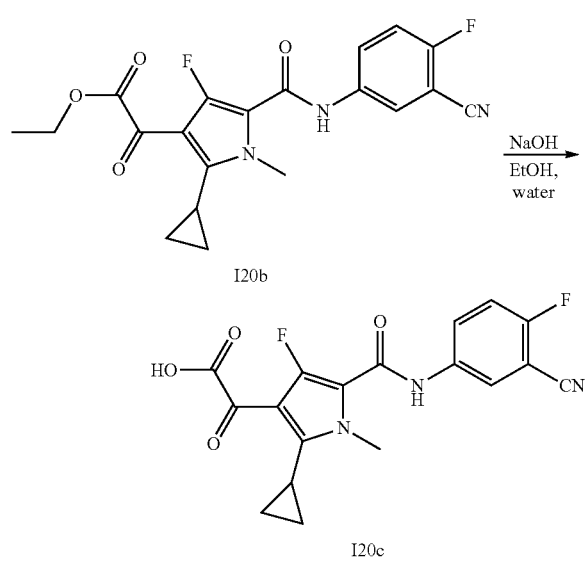

To a solution of ethyl 2-(5-((3-cyano-4-fluorophenyl)carbamoyl)-2-cyclopropyl-4-fluoro-1-methyl-1H-pyrrol-3-yl)-2-oxoacetate (342 mg, 0.852 mmol) in ethanol (5 mL) and water (0.5 mL) was added NaOH (2.56 mL, 1 M in EtOH, 2.56 mmol) at 0° C. The mixture was stirred at room temperature for 1 h. Water (10 mL) and EtOAc (10 mL) were added. The organic layer was discarded and HCl 1 M (5 mL) was added to the aqueous layer until pH=1 then EtOAc (10 mL) was added. The layers were separated and the aqueous layer was extracted with EtOAc (3×10 mL). The combined organic layers were dried over sodium sulfate, filtered and concentrated. The crude was purified by reverse phase flash chromatography (C18_IR_50_F0025, water/ACN from 98/2 to 75/25, 1 h) to afford a non-pure yellow solid. A second purification by reverse phase flash chromatography (C18_IR_50_F0025, water+0.1% of HCOOH/ACN from 98/2 to 75/25, 40 min) afforded intermediate I20c (39 mg, 12% yield) as a white solid.

Synthesis of Intermediate I21c

Step 1

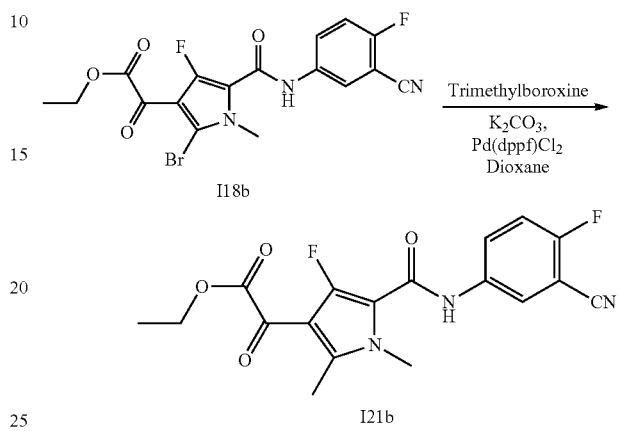

To a solution of intermediate I18b (235 mg, 0.534 mmol) in dioxane (15 mL) were added trimethylboroxine (0.448 mL, 50% w/w solution in THF, 1.60 mmol), potassium carbonate (221 mg, 1.60 mmol) and Pd(dppf)Cl$_2$ (43.6 mg, 0.053 mmol). The resulting mixture was degassed and backfilled with nitrogen then then stirred at 100° C. for 16 h. Water (20 mL) was added and the aqueous layer was extracted with EtOAc (3×15 mL) and the combined organic layers were washed with brine (30 mL), dried over Na$_2$SO$_4$, filtered and concentrated under reduced pressure. The crude was purified by silica column chromatography (cyclohexane/EtOAc from 100/0 to 60/40) to afford ethyl 2-(5-((3-cyano-4-fluorophenyl)carbamoyl)-4-fluoro-1,2-dimethyl-1H-pyrrol-3-yl)-2-oxoacetate (143 mg, 71% yield) as a white solid.

Step 2

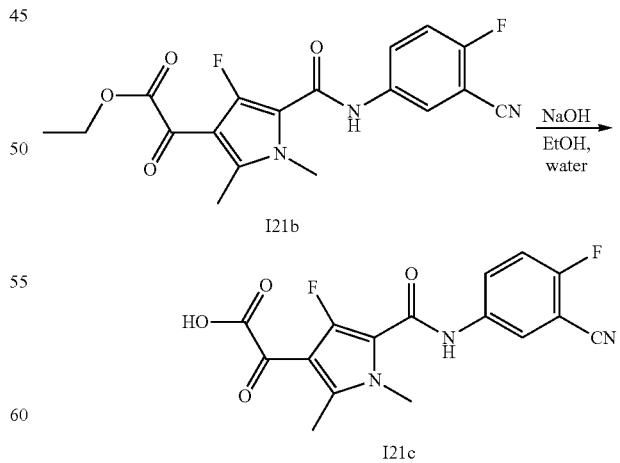

To a solution of ethyl 2-(5-((3-cyano-4-fluorophenyl)carbamoyl)-4-fluoro-1,2-dimethyl-1H-pyrrol-3-yl)-2-oxoacetate (141 mg, 0.376 mmol) in ethanol (2 mL) and water (0.2 mL) was added NaOH (1.13 mL, 1 M in EtOH 1.13 mmol) at 0° C. The mixture was stirred at room temperature for 1 h. Water (10 mL) and EtOAc (10 mL) were added. The organic layer was discarded. HCl 1 M (5 mL) was added to the aqueous layer until pH=1 then EtOAc (10 mL) was added. The layers were separated and the aqueous layer was extracted with EtOAc (3×10 mL).

The combined organic layers were dried over sodium sulphate, filtered and concentrated to afford intermediate I21c (114 mg, 88% yield) as a white solid.

Synthesis of Intermediate I22c

Step 1

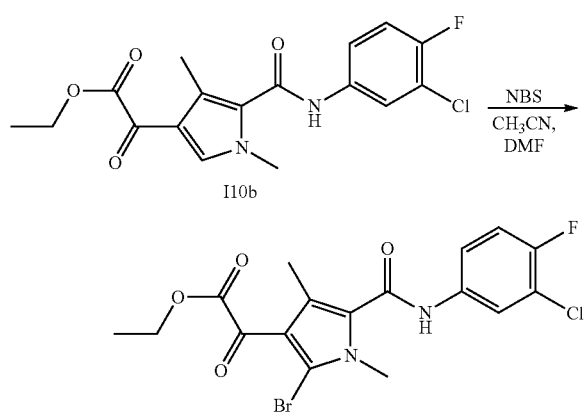

Intermediate I10b (550 mg, 1.5 mmol) was dissolved in CH₃CN (10 mL) and DMF (5 mL). NBS (534 mg, 2.99 mmol) was added at 0° C. and after 1 h, the reaction mixture was allowed to warm to rt. After 2 h at rt, LCMS showed completion of the reaction. The reaction mixture was quenched with EtOAc, sat aq. Na₂S₂O₃ and sat aq. NaHCO₃ and extracted with ethyl acetate (4×). The desired fractions were separated, dried over MgSO₄, filtered and the solvents were evaporated under reduced pressure. The crude was purified on silica column chromatography (heptane/EtOAc 100/0 to 80/20) to afford ethyl 2-(2-bromo-5-((3-chloro-4-fluorophenyl)carbamoyl)-4-fluoro-1-methyl-1H-pyrrol-3-yl)-2-oxoacetate (410 mg, 61% yield).

Step 2

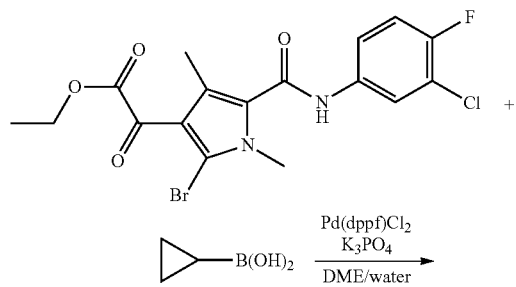

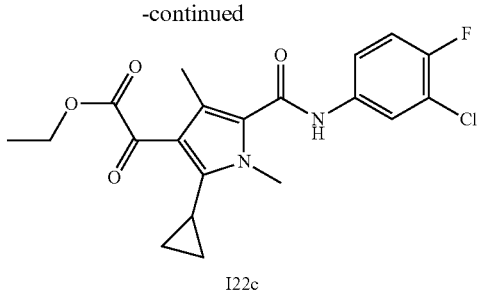

DME (5.2 mL) and water (1.7 mL) were added to a mixture of ethyl 2-(2-bromo-5-((3-chloro-4-fluorophenyl)carbamoyl)-4-fluoro-1-methyl-1H-pyrrol-3-yl)-2-oxoacetate (200 mg, 0.449 mmol), cyclopropylboronic acid (77 mg, 0.898 mmol) and potassium phosphate (352 mg, 1.66 mmol) in a MW flask. The mixture was flushed with nitrogen for 10 min and then Pd(dppf)Cl₂ (65.7 mg, 0.09 mmol) was added. The reaction mixture was stirred at 90° C. overnight. After cooling down to room temperature, the mixture was diluted with EtOAc and water. The organic layer was dried over Na₂SO₄ and concentrated in vacuo but contained only little amount of desired product and several impurities.

The aqueous phase was concentrated and the resulting solid was washed with MeOH several times, the organic solvent collected was concentrated. The crude was purified by silica column chromatography (Heptane/EtOAc 100/0 to 0/100) to afford intermediate I22c (170 mg, 100% yield).

Synthesis of Intermediate I23c

Step 1

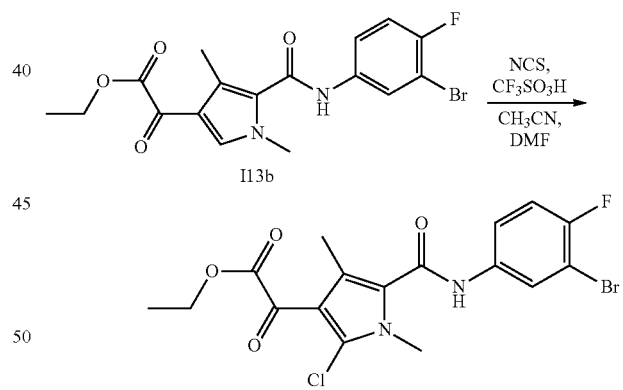

Intermediate I13b (300 mg, 0.62 mmol) was dissolved in acetonitrile (4 mL) and DMF (2 mL). Trifluoromethanesulfonic acid (82 μL, 0.93 mmol) was added. NCS (82.8 mg, 0.62 mmol) was added at 0° C. The reaction mixture was stirred at this temperature for 30 min and then at RT overnight.

The mixture was quenched with water and extracted with DCM (3×), washed with brine, dried over Na₂SO₄, filtered and concentrated under reduced pressure.

This crude was purified by silica gel column chromatography (DCM/MeOH from 100/0 to 95/5) to afford ethyl 2-(5-((3-bromo-4-fluorophenyl)carbamoyl)-2-chloro-1,4-dimethyl-1H-pyrrol-3-yl)-2-oxoacetate (180 mg, 82% pure, 53% yield).

Step 2

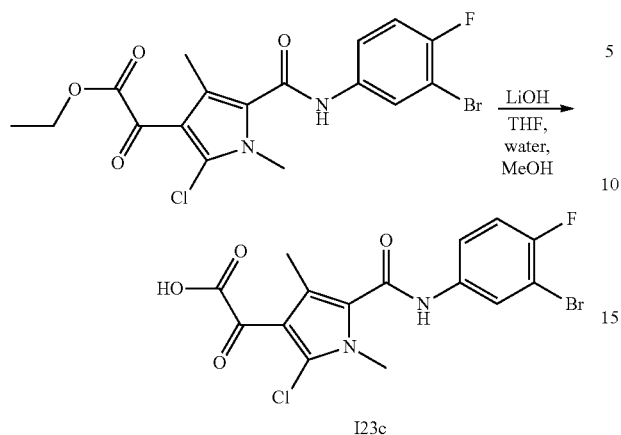

A solution of ethyl 2-(5-((3-bromo-4-fluorophenyl)carbamoyl)-2-chloro-1,4-dimethyl-1H-pyrrol-3-yl)-2-oxoacetate (180 mg, 0.331 mmol) and LiOH monohydrate (28 mg, 0.662 mmol) in water/THF/MeOH (0.6/18/0.6 mL) was stirred 2 h at RT. The mixture solution was concentrated and diluted with water. Then DCM and 1 N HCl were added and the aqueous phase was extracted with DCM. The combined organic layers were combined, dried over MgSO$_4$, filtered and concentrated to afford intermediate I23c (140 mg) and this crude was used as such.

Synthesis of Intermediate I24

Step 1

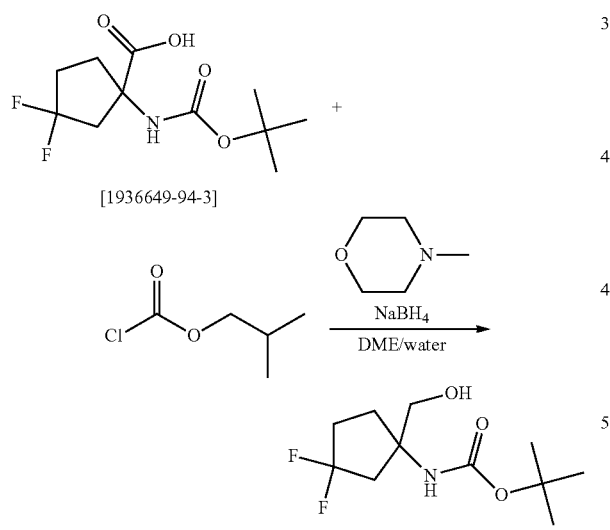

To a solution of tert-butoxycarbonyl)amino)-3,3-difluorocyclopentanecarboxylic acid (1 g, 3.77 mmol) and 4-methylmorpholine (421 mg, 4.15 mmol) in DME (4 mL) at 4° C., was slowly added isobutyl chloroformate (0.54 mL, 4.15 mmol) and the reaction mixture was stirred for 5 min, then filtered into a pre-cooled (4° C.) flask. NaBH$_4$ (213 mg, 5.65 mmol) in water (1.76 mL) was added followed immediately by water (125 mL). The reaction was then warmed to 20° C. and stirred for 30 min. The reaction mixture was extracted with DCM (3×20 mL). The combined organic layers were concentrated under reduced pressure and the crude was used as such in the next step.

Step 2

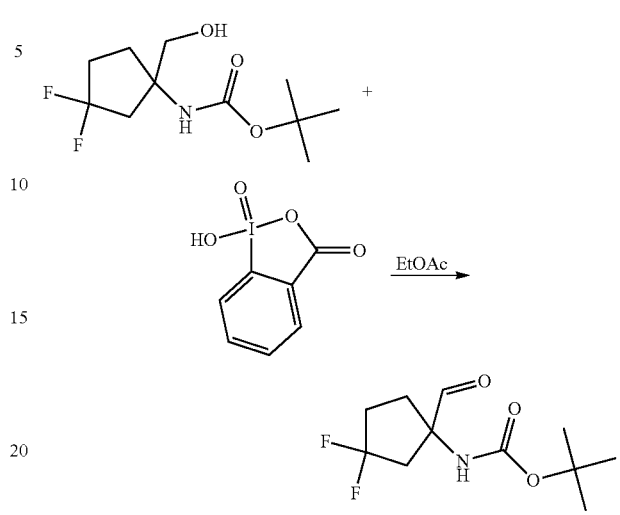

2-Iodoxybenzoic acid (1.05 g, 3.75 mmol) was added to a solution of tert-butyl (3,3-difluoro-1-(hydroxymethyl)cyclopentyl)carbamate (0.75 g, 3 mmol) in EtOAc (10 mL) and heated overnight at 80° C. The reaction mixture was cooled with an ice bath, filtered and the filtrate was evaporated to dryness. The residue was used as such in the next step.

Step 3

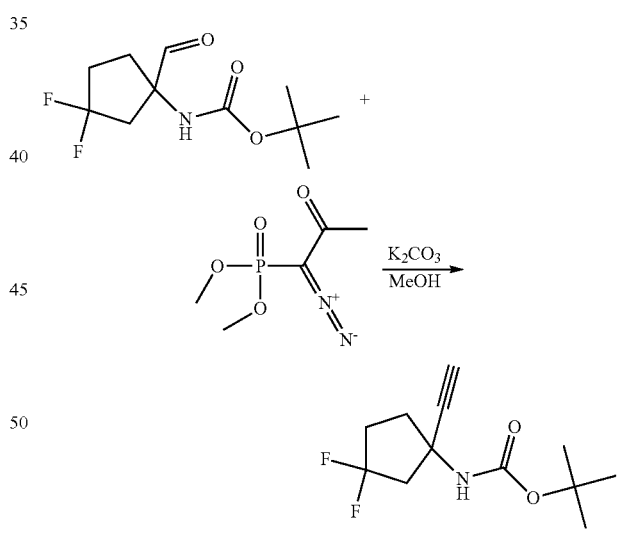

Dimethyl (1-diazo-2-oxopropyl)phosphonate (0.45 mL, 3 mmol) was added to a suspension of tert-butyl (3,3-difluoro-1-formylcyclopentyl)carbamate (748 mg, 3 mmol) and K$_2$CO$_3$ (829 mg, 6 mmol) in MeOH at 0° C. After 30 minutes the reaction mixture was allowed to reach room temperature and stirring was continued overnight. The reaction mixture was evaporated to dryness. The residue was partitioned between diethyl ether (5 mL) and water (5 mL). The organic layer was dried over Na$_2$SO$_4$, filtered and evaporated to dryness. The residue was used as such in the next step.

Step 4

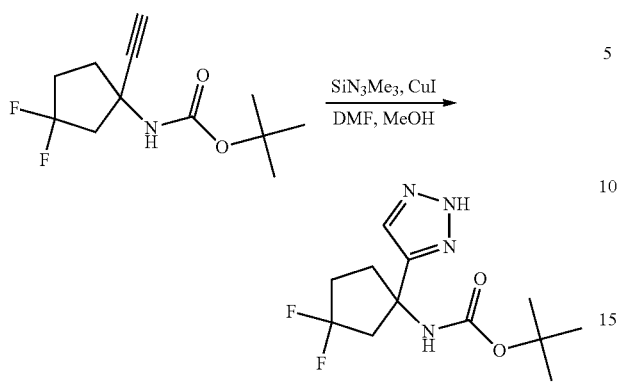

tert-Butyl (1-ethynyl-3,3-difluorocyclopentyl)carbamate (0.5 g, 2.04 mmol), azidotrimethylsilane (0.8 mL, 5.71 mmol) and copper iodide (19.4 mg, 0.1 mmol) were dispensed in DMF (5 mL) and MeOH (0.5 mL) and heated 5 hours at 100° C. The volatiles were removed under reduced pressure and the residue was purified on silica column chromatography using a heptane to EtOAc gradient to afford tert-butyl (3,3-difluoro-1-(2H-1,2,3-triazol-4-yl)cyclopentyl)carbamate (330 mg, 56% yield) as a white powder.

Step 5

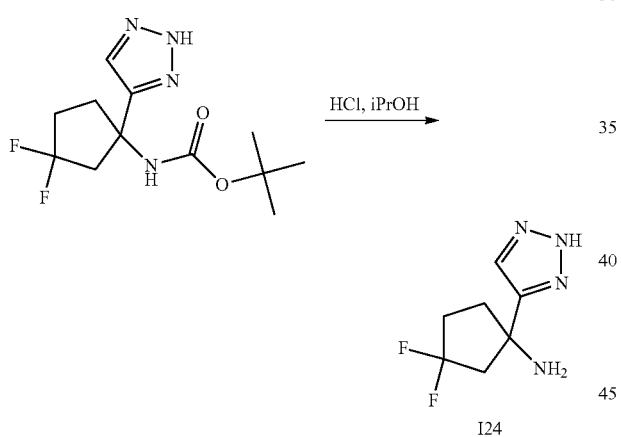

Tert-butyl (3,3-difluoro-1-(2H-1,2,3-triazol-4-yl)cyclopentyl)carbamate (330 mg, 1.09 mmol) was dissolved in HCl (1.81 mL, 6 M in iPrOH, 10.87 mmol) and stirred 18 hours at room temperature. The volatiles were removed under reduced pressure and the residue was triturated in DIPE, filtered and dried in the oven overnight yielding intermediate 24 (200 mg, 66% yield).

Synthesis of Intermediate I25

Step 1

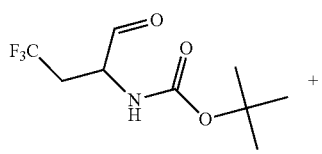

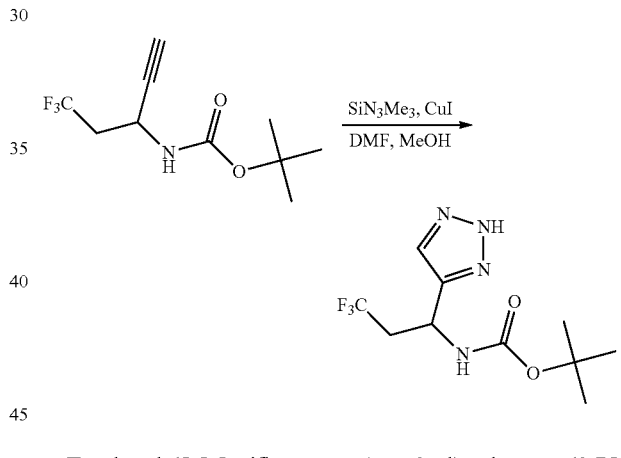

Dimethyl (1-diazo-2-oxopropyl)phosphonate (0.62 mL, 4.15 mmol) was added to a suspension of tert-butyl (4,4,4-trifluoro-1-oxobutan-2-yl)carbamate (1 g, 4.15 mmol) and K₂CO₃ (145 mg, 8.29 mmol) in MeOH at 0° C. After 30 minutes the reaction mixture was allowed to reach room temperature and stirring was continued overnight. The reaction mixture was evaporated to dryness. The residue was partitioned between diethyl ether (5 mL) and water (5 mL). The organic layer was dried over Na₂SO₄, filtered and evaporated to dryness. The residue was used as such in the next step.

Step 2

Tert-butyl (5,5,5-trifluoropent-1-yn-3-yl)carbamate (0.75 g, 3.16 mmol), azidotrimethylsilane (1.23 mL, 8.85 mmol) and copper iodide (30.11 mg, 0.16 mmol) were dispensed in DMF (5 mL) and MeOH (0.5 mL) and heated 5 hours at 100° C. The volatiles were removed under reduced pressure and the residue was purified on silica using a heptane to EtOAc gradient yielding to tert-butyl (3,3,3-trifluoro-1-(2H-1,2,3-triazol-4-yl)propyl)carbamate (490 mg, 55% yield) as a white powder.

Step 3

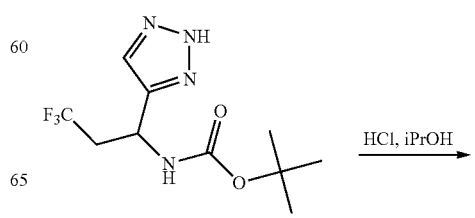

-continued

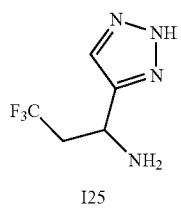

I25

Tert-butyl (3,3,3-trifluoro-1-(2H-1,2,3-triazol-4-yl)propyl)carbamate (500 mg, 1.78 mmol) was dissolved in HCl (2.97 mL, 6 M in iPrOH, 17.84 mmol) and stirred 18 hours at rt. The volatiles were removed under reduced pressure and the residue was triturated in DIPE, filtered and dried in the oven overnight yielding intermediate I25 (230 mg, 62% yield) as yellow powder.

Synthesis of Intermediate I26

Step 1

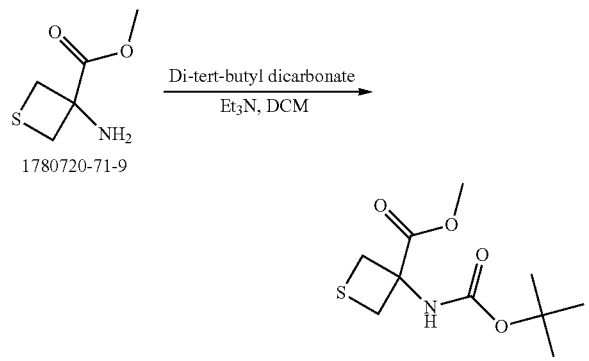

1780720-71-9

To a solution of methyl 3-aminothietan-3-carboxylate (200 mg, 1.36 mmol) in dichloromethane (5 mL) was added triethylamine (412 mg, 4.08 mmol) and di-tert-butyl dicarbonate (593 mg, 2.72 mmol) under ice-cooling. The solution was stirred for 5 h at RT. The mixture was extracted with dichloromethane. The organic layer was dried over sodium sulphate and filtered. The filtrate was concentrated in vacuo and the crude was used as such in the next step Step 2

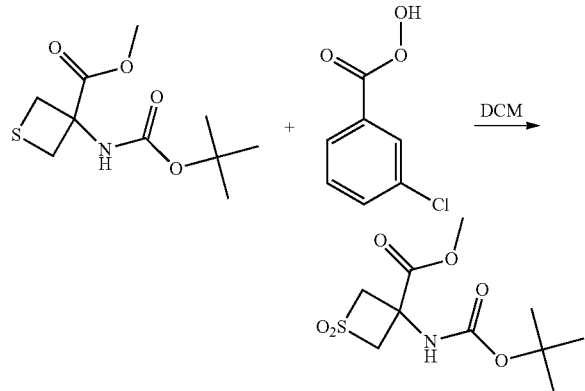

To a solution of methyl 3-((tert-butoxycarbonyl)amino) thietane-3-carboxylate (1.5 g, 6.06 mmol) in dichloromethane (20 ml) was added m-chloroperoxybenzoic acid (2.62 g, 15.16 mmol) at 0° C. The solution was stirred for 8 h at room temperature. The solvent was removed under reduced pressure and the residue was purified by recrystallization (EtOAc/Hexane) to afford the desired methyl 3-((tert-butoxycarbonyl)amino)thietane-3-carboxylate 1,1-dioxide (1.36 g, 80% yield) as a white solid.

Step 3

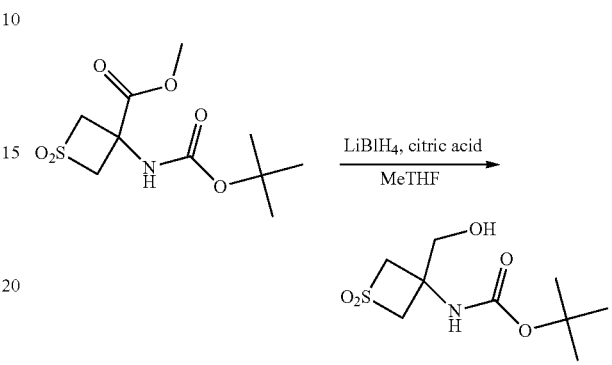

Lithium borohydride (4.87 mL, 19.48 mmol) was added slowly to an ice cooled solution of methyl 3-((tert-butoxycarbonyl)amino)thietane-3-carboxylate 1,1-dioxide (1.3 g, 4.87 mmol) in dry 2-MeTHF (25 mL). The reaction mixture was allowed to reach room temperature over 15 minutes and further stirred for 1 hour. TLC showed complete conversion of the starting material. Citric acid (9.74 mL, 1 M, 9.74 mmol) was slowly added keeping the temperature below 20° C. (foaming). After addition the reaction mixture was diluted with water (75 mL) and DCM (100 mL). The layers were separated and the aqueous layer was extracted with DCM (2×50 mL). The combined organic layers were dried over MgSO4, filtered and evaporated to dryness yielding tert-butyl (3-(hydroxymethyl)-1,1-dioxidothietan-3-yl)carbamate as a white powder which was used as such in the next step.

Step 4

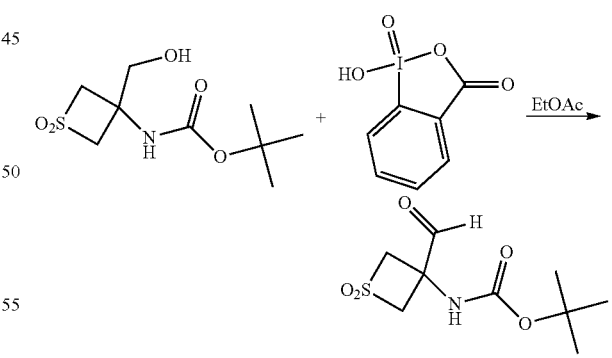

2-iodoxybenzoic acid (1.7 g, 6.07 mmol) was added to a solution of tert-butyl (3-(hydroxymethyl)-1,1-dioxidothietan-3-yl)carbamate (1.22 g, 4.85 mmol) in EtOAc (75 mL) and heated overnight at 80° C. The reaction mixture was cooled with an ice bath, filtered and the filtrate was evaporated to dryness. The residue was purified on silica column chromatography using a heptane to EtOAc gradient yielding tert-butyl (3-formyl-1,1-dioxidothietan-3-yl)carbamate as a white powder.

In analogous manner to intermediate I24 or intermediate I25
Intermediate I26

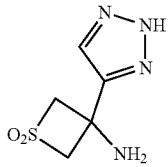

was obtained in 3 steps starting from tert-butyl (3-formyl-1,1-dioxidothietan-3-yl)carbamate.
Intermediate I27

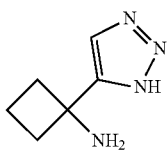

was synthetized in 5 steps starting from methyl 3-((tert-butoxycarbonyl)amino)oxetane-3-carboxylate
Intermediate

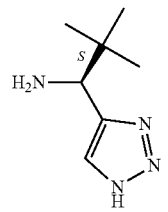

was synthetized in 4 steps starting from N-Boc-(S)-(+)-tert-leucinol.
Intermediate I29

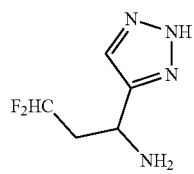

was produced starting from commercial tert-butyl N-(4,4-difluoro-1-oxobutan-2-yl)carbamate.

Synthesis of Intermediate I30

Step 1

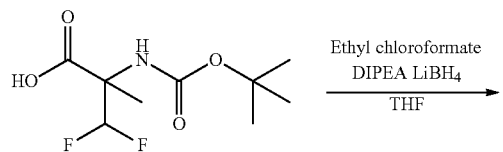

-continued

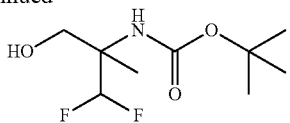

To a solution of 2-{[(tert-butoxy)carbonyl]amino}-3,3-difluoro-2-methylpropanoic acid (800 mg, 3.34 mmol) in THF (8 mL) at 0° C. were added DIPEA (699 µL, 4.01 mmol) and dropwise ethyl chloroformate (352 µL, 3.68 mmol). The reaction was stirred 2 hours at 0° C. The formed precipitate was filtered and washed with anhydrous tetrahydrofuran (5 mL). The filtrate was cooled to 0° C. followed by the addition dropwise of a solution of lithium borohydride (1.67 mL, 4N in THF, 6.69 mmol). The reaction was stirred 4 hours at room temperature. The reaction mixture was diluted with water (100 mL) and extracted with EtOAc (3×100 mL). Combined organic layers were washed with brine, dried over Na₂SO₄, filtered and concentrated under reduced pressure. The crude was purified by silica gel column chromatography (cyclohexane/EtOAc from 100/0 to 7/3) to afford tert-butyl (1,1-difluoro-3-hydroxy-2-methyl-propan-2-yl)carbamate (473 mg, 63% yield) as a white solid.

Step 2

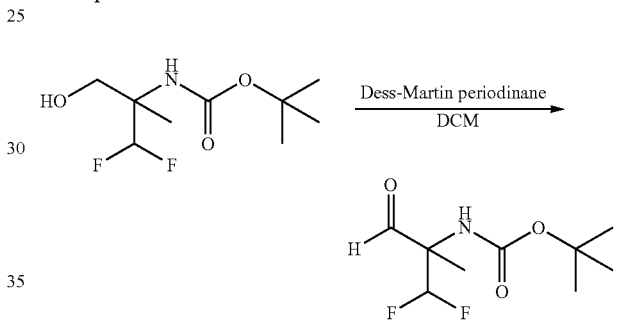

To a solution of tert-butyl (1,1-difluoro-2-methyl-3-oxo-propan-2-yl)carbamate (473 mg, 2.10 mmol) in DCM (16.8 mL) at 0° C. was added Dess-Martin periodinane (1.25 g, 2.94 mmol). The reaction was stirred 6 hours allowing the ice bath coming back to room temperature. The reaction mixture was quenched with a 1 M solution of Na₂S₂O₃ (150 mL). The aqueous layer was extracted with EtAOc (3×100 mL). The combined organic layers were washed with an aqueous saturated solution of NaHCO₃ (2×100 mL) brine, dried over Na₂SO₄ and concentrated under reduced pressure. The crude was purified by silica column chromatography (cyclohexane/EtOAc from 100/0 to 8/2) to afford tert-butyl (1,1-difluoro-2-methyl-3-oxopropan-2-yl)carbamate (451 mg, 96%) as a white solid.

Step 3

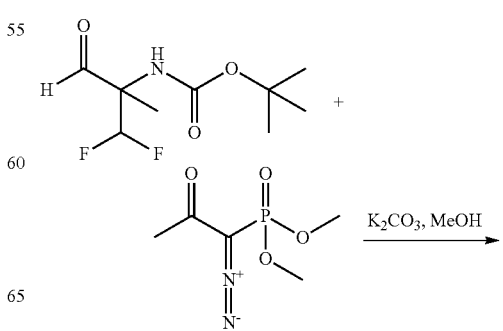

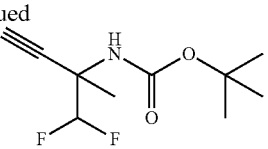

To a solution of tert-butyl (1,1-difluoro-2-methyl-3-oxo-propan-2-yl)carbamate (450 mg, 2.02 mmol) in methanol (7.9 mL) at 0° C. were added potassium carbonate (557 mg, 4.03 mmol) and dimethyl(1-diazo-2-oxopropyl)phosphonate (318 µL, 2.12 mmol). The reaction was stirred 18 hours allowing the ice bath coming back to room temperature. The reaction mixture was concentrated under reduced pressure. The obtained residue was diluted in H₂O (100 mL) and extracted with Et₂O (3×100 mL). Combined organic layers were dried over Na₂SO₄, filtered and concentrated to dryness. The obtained residue was solubilised in DCM (10 mL), dried over Na₂SO₄, filtered and concentrated to afford tert-butyl (1,1-difluoro-2-methylbut-3-yn-2-yl)carbamate (326 mg, 74%).

Step 4

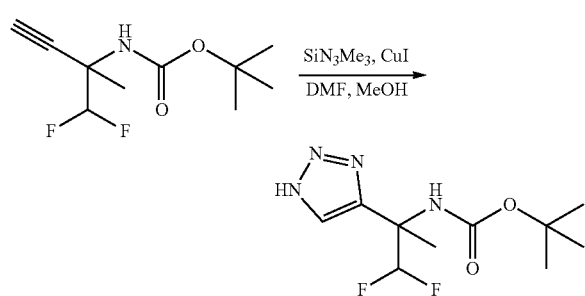

To a solution of tert-butyl (1,1-difluoro-2-methylbut-3-yn-2-yl)carbamate (415 mg, 1.89 mmol) in a mixture of DMF (3 mL) and Methanol (0.3 mL) in a MW vial were added copper iodide (18.0 mg, 0.095 mmol) and azidotrimethylsilane (702 µL, 5.30 mmol). The reaction vessel was sealed and then stirred 5 hours at 100° C. The reaction mixture was diluted with EtOAc (100 mL), washed with brine (3×100 mL), dried over Na₂SO₄, filtered and concentrated. The crude was purified on silica gel column chromatography (DCM/MeOH from 100/0 to 95/5) to afford tert-butyl (1,1-difluoro-2-(1H-1,2,3-triazol-4-yl)propan-2-yl)carbamate (629 mg, 86%) as a light yellow oil which was used as such in the next step.

Step 5:

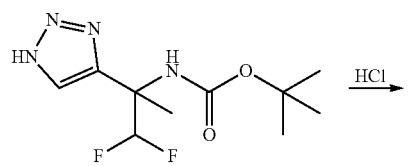

I30

A solution of tert-butyl (1,1-difluoro-2-(1H-1,2,3-triazol-4-yl)propan-2-yl)carbamate (625 mg, 1.63 mmol) in HCl (4.33 mL, 6N in iPrOH, 26.0 mmol) was stirred for 2 hours at room temperature. The reaction mixture was concentrated to dryness, co-evaporated with DCM (5×10 mL), vacuum dried overnight at 50° C. to afford intermediate I30 (312 mg, 97% yield) a light green solid which was used as such in the next step.

In an analogous manner intermediate I31

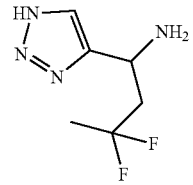

was synthesized in 4 steps from tert-butyl N-(3,3-difluoro-1-hydroxybutan-2-yl)carbamate.

In an analogous manner intermediate I32

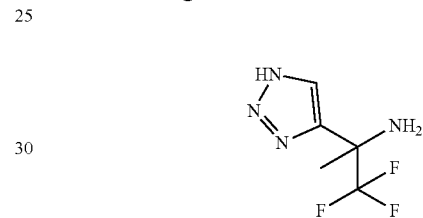

was synthesized in 5 steps from 2-[(tert-butoxycarbonyl)amino]-3,3,3-trifluoro-2-methylpropanoic acid.

In an analogous manner intermediate I33

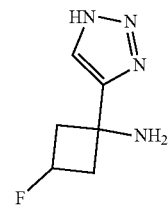 [SMILES: NC1(c2c[nH]nn2)CC(F)C1]

was synthesized in 5 steps from 1-(Boc-amino)-3-fluorocyclobutanecarboxylic acid (provided as a mixture trans/cis: 7/3 or 3/7).

Synthesis of Intermediate I34

Step 1

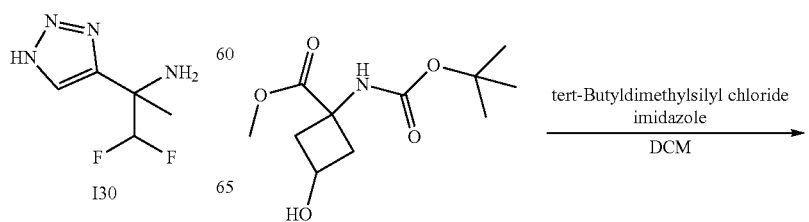

-continued

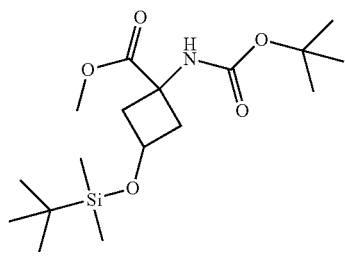

To a solution of methyl 1-{[(tert-butoxy)carbonyl]amino}-3-hydroxycyclobutane-1-carboxylate (900 mg, 3.67 mmol, mixture trans/cis 7/3 or 3/7) in DCM (36 mL) at 0° C. were added imidazole (824 mg, 12.1 mmol) and tert-butyldimethylsilyl chloride (996 mg, 6.61 mmol). The reaction was stirred 16 hours allowing the ice bath coming back to room temperature. The reaction mixture was diluted with DCM (50 mL), washed with an aqueous HCl 1N solution (2×150 mL), an aqueous saturated NaHCO₃ solution (150 mL), brine, dried over Na₂SO₄, filtered and concentrated to afford methyl 1-((tert-butoxycarbonyl)amino)-3-((tert-butyldimethylsilyl)oxy)cyclobutane-1-carboxylate which was used as such in the next step.

Step 2

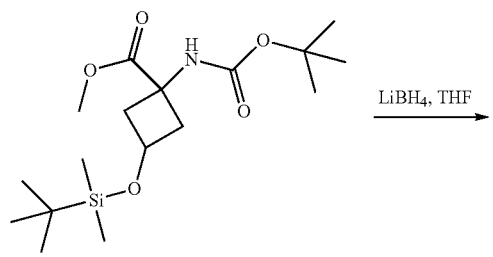

To a solution of methyl 1-((tert-butoxycarbonyl)amino)-3-((tert-butyldimethylsilyl)oxy)cyclobutane-1-carboxylate (1.63 g, 3.67 mmol) in THF (36 mL) at 0° C. was added dropwise lithium borohydride (2.75 mL, 4N in THF, 11.0 mmol). The reaction was stirred 3 hours allowing the ice bath coming back to room temperature. The reaction mixture was diluted with water (100 mL) and extracted with EtOAc (3×100 mL). The combined organic layers were washed with brine, dried over Na₂SO₄, filtered and concentrated under reduced pressure.

The crude was purified by silica gel column chromatography (cyclohexane/EtOAc from 100/0 to 8/2) to afford tert-butyl (3-((tert-butyldimethylsilyl)oxy)-1-(hydroxymethyl)cyclobutyl)carbamate (1.15 g, 94% yield) as a white solid.

Step 3

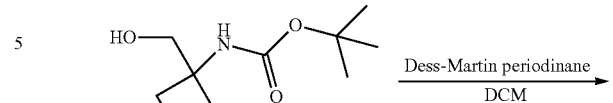

To a solution of tert-butyl (3-((tert-butyldimethylsilyl)oxy)-1-(hydroxymethyl)cyclobutyl)carbamate (1.15 g, 3.45 mmol) in DCM (28 mL) at 0° C. was added Dess-Martin periodinane (2.05 g, 4.84 mmol). The reaction was stirred 6 hours allowing the ice bath coming back to room temperature. The reaction mixture was quenched with a 1 M solution of Na₂S₂O₃ (150 mL). The aqueous layer was extracted with DCM (3×100 mL). Combined organic layers were washed with an aqueous saturated solution of NaHCO₃ (2×100 mL) brine, dried over Na₂SO₄ and concentrated. The crude was purified by silica gel column chromatography (cyclohexane/EtOAc from: 100/0 to 8/2) to afford tert-butyl (3-((tert-butyldimethylsilyl)oxy)-1-formylcyclobutyl)carbamate (1.07 g, 94%) as a white solid.

Step 4

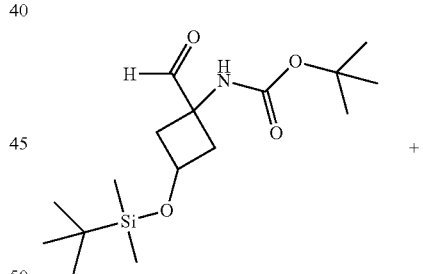

+

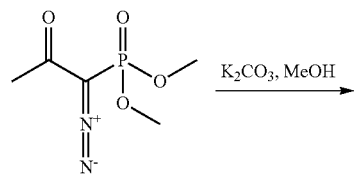

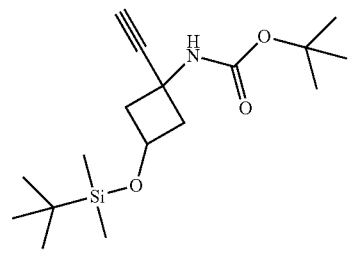

To a solution of tert-butyl (3-((tert-butyldimethylsilyl)oxy)-1-formylcyclobutyl)carbamate (1.07 g, 3.25 mmol) in methanol (12.7 mL) at 0° C. were added potassium carbonate (899 mg, 6.51 mmol) and dimethyl(1-diazo-2-oxopropyl)phosphonate (513 µL, 3.42 mmol). The reaction was stirred 18 hours allowing the ice bath coming back to room temperature. The reaction was concentrated. The obtained residue was diluted in water (100 mL) and extracted with Et₂O (3×150 mL). Combined organic layers were dried over Na₂SO₄, filtered and concentrated to dryness to afford tert-butyl (3-((tert-butyldimethylsilyl)oxy)-1-ethynylcyclobutyl)carbamate (950 mg, 82% yield) as a white solid.

Step 5

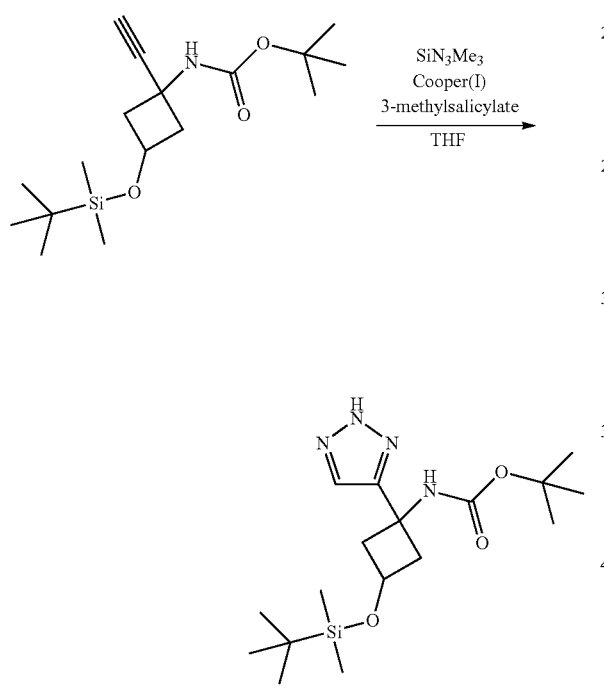

To a solution of tert-butyl (3-((tert-butyldimethylsilyl)oxy)-1-ethynylcyclobutyl)carbamate (900 mg, 2.52 mmol) in THF (5.8 mL) were added copper(I) 3-methylsalicylate (595 mg, 2.77 mmol) and azidotrimethylsilane (401 µL, 3.02 mmol). The reaction mixture was stirred 4 hours at room temperature. The reaction mixture was diluted with EtOAc (30 mL) and MeOH (30 mL) and SiliaMetS®TAAcONa L=0.41 mmol/g (2.5 eq., 15 g) was added. The suspension was stirred 1 hour and filtered. The solid phase was washed with MeOH and the filtrate was concentrated. The obtained residue was dissolved in EtOAc (100 mL) washed with an aqueous saturated NaHCO₃ solution (3×150 mL), brine (50 mL), dried over Na₂SO₄, filtered and concentrated. The crude was purified on silica column chromatography (DCM/MeOH from 100/0 to 95/5) to afford tert-butyl (3-((tert-butyldimethylsilyl)oxy)-1-(2H-1,2,3-triazol-4-yl)cyclobutyl)carbamate (898 mg, 90% yield) as a white solid.

Step 6

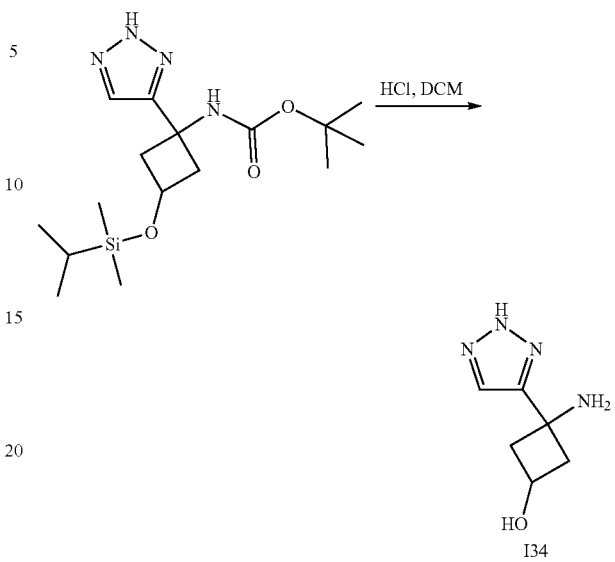

A solution of tert-butyl (3-((tert-butyldimethylsilyl)oxy)-1-(2H-1,2,3-triazol-4-yl)cyclobutyl)carbamate (890 mg, 2.39 mmol) in a mixture of DCM (9.5 mL) and HCl (9.55 mL, 4N in dioxane, 38.2 mmol) was stirred 2 hours at room temperature. The reaction mixture was concentrated to dryness, co-evaporated with DCM (5×10 mL) to afford 556 mg of intermediate I34 as a white solid (yield considered quantitative) which was used as such in the next step.

Synthesis of Intermediate I35

Step 1

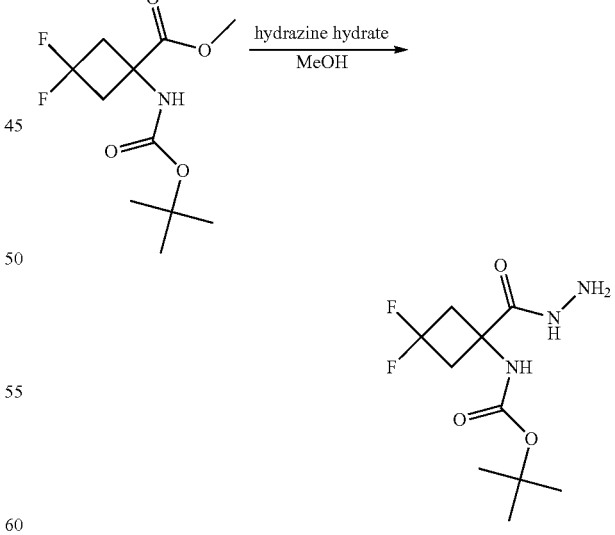

Methyl 1-([[(tert-butoxy)carbonyl]amino)-3,3-difluorocyclobutane-1-carboxylate (5 g, 18.85 mmol) and hydrazine hydrate were dissolved in MeOH (20 mL) and heated overnight at 60° C. The precipitate was filtered off and dried yielding tert-butyl (3,3-difluoro-1-(hydrazinecarbonyl)cyclobutyl)carbamate (4.02 g, yield 80%) as a white powder.

Step 2

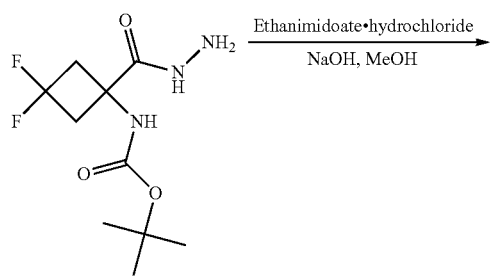

Tert-butyl (3,3-difluoro-1-(hydrazinecarbonyl)cyclobutyl)carbamate (1 g, 3.77 mmol), ethyl ethanimidoate.hydrochloride (489 mg, 3.96 mmol) and NaOH (165.8 mg, 4.15 mmol) were dispensed in MeOH (10 mL) and stirred 2 hours at 70° C. LCMS showed product formation. Stirring was continued overnight at 85° C. The volatiles were removed under reduced pressure and the residue was triturated in DCM and filtered yielding tert-butyl (3,3-difluoro-1-(5-methyl-4H-1,2,4-triazol-3-yl)cyclobutyl)carbamate powder (848 mg, 78% yield) as a white.

Step 3

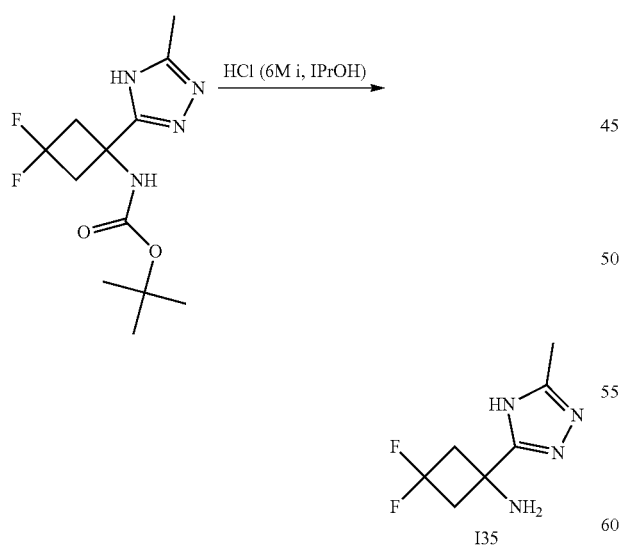

Tert-butyl (3,3-difluoro-1-(5-methyl-4H-1,2,4-triazol-3-yl)cyclobutyl)carbamate (848 mg, 2.94 mmol) was dispensed in HCl (40 mL, 6 M in iPrOH, 240 mmol) and stirred overnight at room temperature. The volatiles were removed under reduced pressure and the residue was redissolved in MeOH and evaporated to dryness yielding intermediate I35 as a white powder (754 mg, 98% yield).

Synthesis of Intermediate I36

Step 1

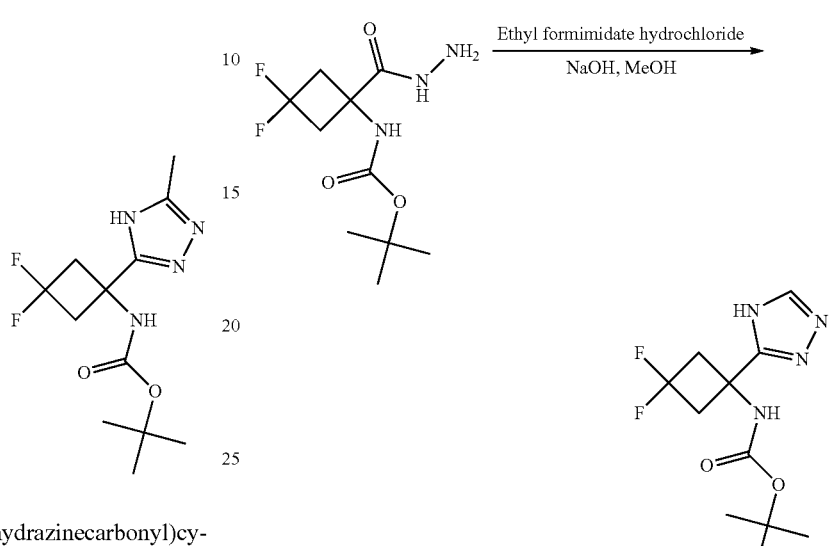

Tert-butyl (3,3-difluoro-1-(5-methyl-4H-1,2,4-triazol-3-yl)cyclobutyl)carbamate (1 g, 3.77 mmol), ethyl formimidate hydrochloride (474 mg, 4.34 mmol) and NaOH (165 mg, 4.15 mmol) were suspended in MeOH (10 mL) and stirred overnight at 70° C. The volatiles were removed and the residue was dispensed in EtOH (10 mL) and heated 1 hour in the microwave at 140° C. The reaction mixture was cooled down and the precipitate was filtered off yielding tert-butyl (3,3-difluoro-1-(4H-1,2,4-triazol-3-yl)cyclobutyl) carbamate as a white powder which used as such.

Step 2

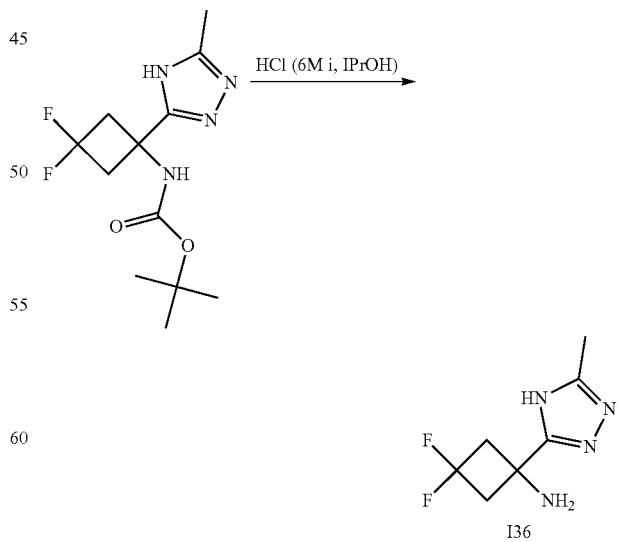

HCl (6.28 mL, 6 M in iPrOH, 37.7 mmol) was added to a solution of tert-butyl (3,3-difluoro-1-(4H-1,2,4-triazol-3- yl)cyclobutyl) (1.03 mg, 3.77 mmol) in iPrOH (10 mL). The reaction mixture was stirred overnight at room temperature. The volatiles were removed under reduced pressure yielding intermediate I36 (508 mg, 54% yield) as a white powder.

Synthesis of Intermediate I37

Step 1

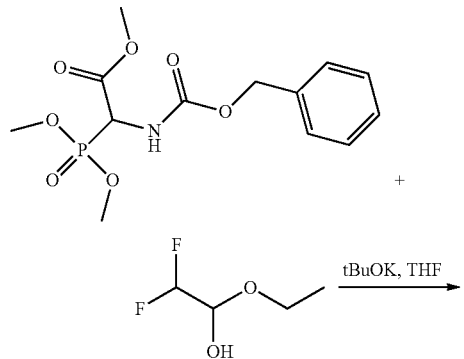

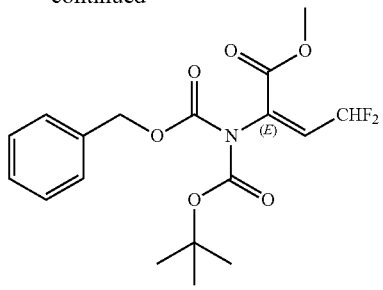

To a solution of methyl (E)-2-(((benzyloxy)carbonyl)amino)-4,4-difluorobut-2-enoate (6 g, 21.03 mmol, 1 eq) in tetrahydrofuran (50 mL) with 4-dimethylaminopyridine (0.26 g, 2.10 mmol, 0.1 eq), di-tert-butyl dicarbonate (6.89 g, 31.55 mmol, 1.5 eq) was added at 0° C. The resulting mixture was stirred at room temperature overnight. The reaction mixture was concentrated under reduced pressure. The residue was purified on silica column chromatography (EA/PE 1/3) to afford (E)-methyl 2-((benzyloxycarbonyl)(tert-butoxycarbonyl)amino)-4,4-difluorobut-2-enoate (7 g, 86% yield) as a light oil.

Step 3

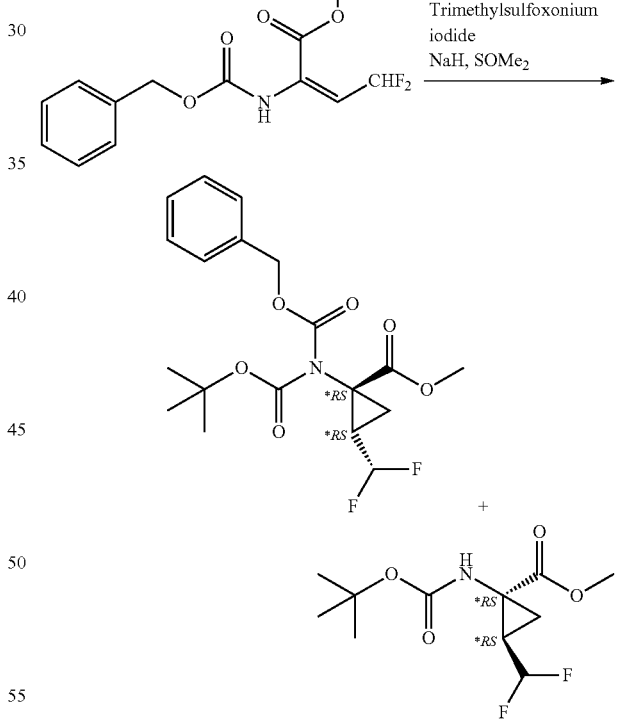

To a suspension of potassium tert-butoxide (2.98 g, 26.56 mmol) in tetrahydrofuran (40 mL) was added N-Cbz-2-phosphonoglycine trimethyl ester (8 g, 24.15 mmol) at −78° C. under N$_2$. It was stirred for 30 min at this temperature and then difluoroacetaldehyde ethyl hemiacetal (6.09 g, 48.30 mmol) was added slowly. The resulting mixture was warmed up to room temperature and stirred for 18 h. The reaction mixture was then quenched with water, adjusted to pH=5 by adding few drops of 1 N HCl. The mixture was extracted with EtOAc. The organic layer was dried over MgSO4, filtered and concentrated. The crude was purified on silica column chromatography (EtOAc/PE 70/30) to afford methyl (E)-2-(((benzyloxy)carbonyl)amino)-4,4-difluorobut-2-enoate (6 g, 87% yield) as a light oil.

Step 2

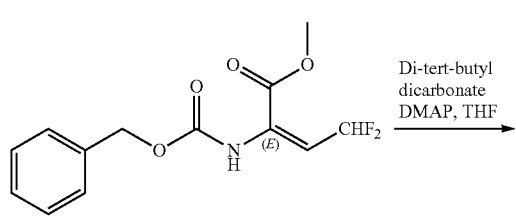

To a mixture of sodium hydride (0.61 g, 25.30 mmol) in DMSO (60 ml) was added trimethylsulfoxonium iodide (5.78 mg, 26.27 mmol) and the mixture was stirred at room temperature for 1 h. Then (E)-methyl 2-((benzyloxycarbonyl)(tert-butoxycarbonyl)amino)-4,4-difluorobut-2-enoate (7.5 g, 19.46 mmol, 1 eq) was added and the mixture was heated at 80° C. for 2 h. The reaction was then cooled to RT and stirred for 18 h. Water (5 mL) was added followed by 1N HCl to adjust the pH to 5. This mixture was extracted with Ethyl acetate and dried over MgSO4, filtered, concentrated uder reduced pressure. The crude was purified on solica column chromatography EtOAc/PE (85/15) to afford methyl 1-((benzyloxycarbonyl)(tert-butoxycarbonyl)amino)-2-(difluoromethyl)cyclopropanecarboxylate (2 g, 25% yield) and methyl 1-(tert-butoxycarbonylamino)-2-(difluoromethyl) cyclopropanecarboxylate (1.5 g, 29% yield) as oils.

Step 4

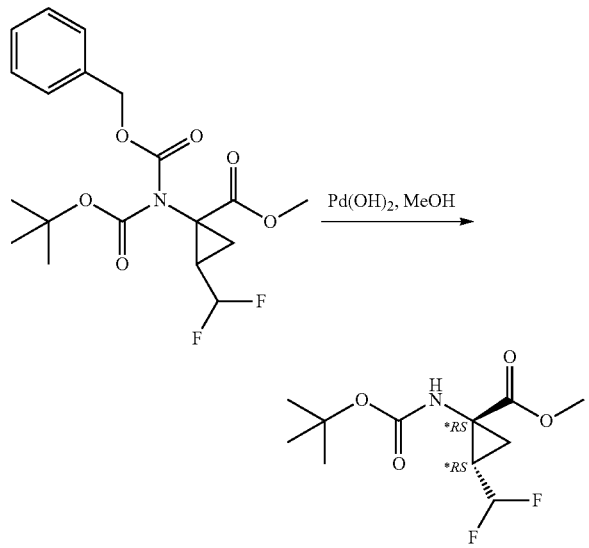

To a solution of methyl 1-(((benzyloxy)carbonyl)(tert-butoxycarbonyl)amino)-2-(difluoromethyl)cyclopropane-1-carboxylate (3 g, 7.5 mmol) in methanol (20 ml) was added palladium hydroxide (105.5 mg, 0.751 mmol). The solution was stirred for 1 h at RT. The reaction mixture was concentrated. The crude was purified by reverse C18 column (0-60% H$_2$O (0.5% TFA)/ACN) to afford 1-(tert-butoxycarbonylamino)-2-(difluoromethyl)cyclopropanecarboxylic acid (1.27 g, 61% yield) as a white solid.

Step 5

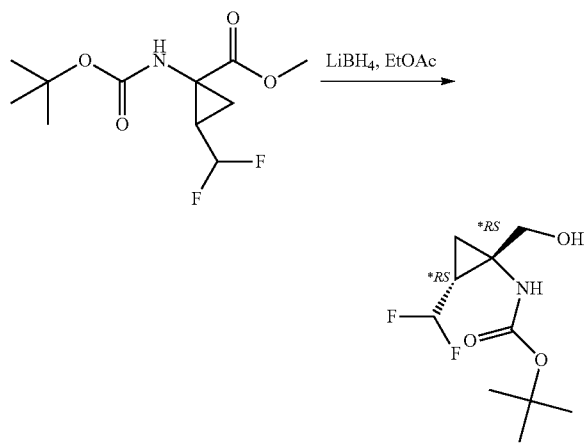

Lithium borohydride (7.5 mL, 4 M in THF, 30 mmol) was added slowly to an ice cooled solution of 1-(tert-butoxycarbonylamino)-2-(difluoromethyl)cyclopropanecarboxylic acid (1.9 g, 7.17 mmol) in dry Me-THF (50 mL). The reaction mixture was allowed to reach room temperature over 15 minutes and further stirred for 1 hour. TLC showed complete conversion of the starting material. EtOAc (11.7 mL, 120 mmol) was added and the reaction mixture was stirred for 1 hour. The reaction mixture was diluted with water (100 mL) and DCM (100 mL). The layers were separated and the aqueous layer was extracted with DCM (2×50 mL). The combined organic layers were dried over MgSO4, filtered and evaporated to dryness yielding tert-butyl (2-(difluoromethyl)-1-(hydroxymethyl)cyclopropyl) carbamate as a white powder which was used as such in the next step.

Step 6-9: Intermediate I37

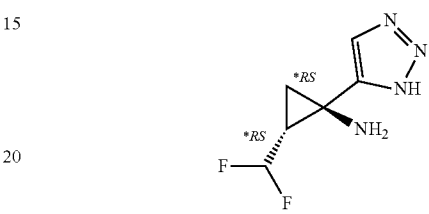

was obtained in 3 steps in a similar way intermediate I24 was obtained.

Synthesis of Intermediate I38

Step 1

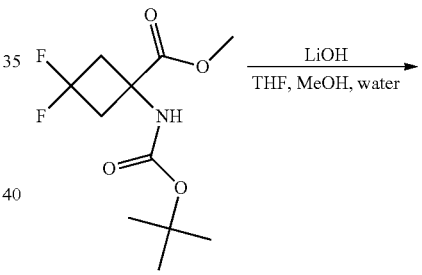

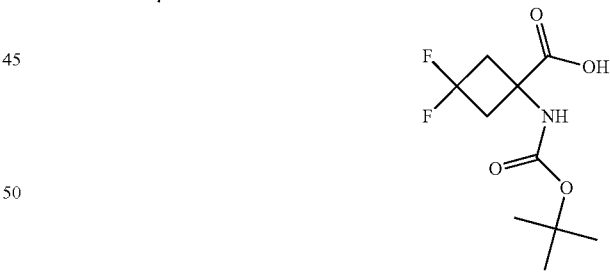

To a mixture of methyl 1-{[(tert-butoxy)carbonyl] amino}-3,3-difluorocyclobutane-1-carboxylate (10 g, 37.70 mmol) and lithium hydroxide (1.81 g, 75.40 mmol,) was added mixture of THF/MeOH/H$_2$O (v/v/v=3/1/1) (70 ml). The mixture was maintained under nitrogen and stirred at RT for 2 h. After reaction, organic solvents were removed under reduced pressure. The remained water phase was acidified by 1N HCl until white solid appeared (pH=2). The solid was collected through filtration and dried under reduced pressure to afford 1-((tert-butoxycarbonyl)amino)-3,3-difluorocyclobutane-1-carboxylic acid (8.8 g, 92% yield) as a white solid.

Step 2

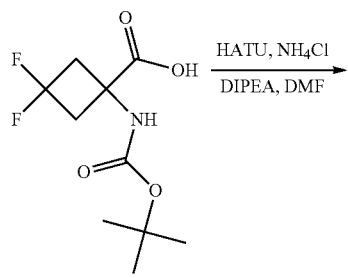

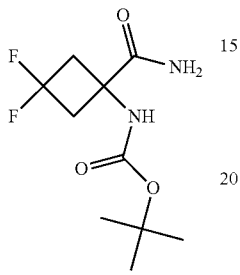

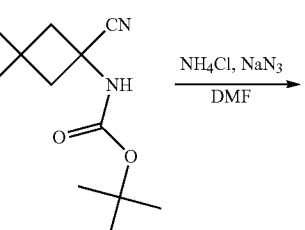

To a solution of 1-((tert-butoxycarbonyl)amino)-3,3-difluorocyclobutane-1-carboxylic acid (8.8 g, 35.03 mmol) in DMF (50 ml) was added ammonium chloride (9.37 g, 175 mmol) and HATU (19.98 g, 52.54 mmol) successively. Then, to the resulting mixture was dropwise added DIPEA (22.64 g, 175.14 mmol) at 0° C. the reaction mixture was maintained under nitrogen and stirred at RT overnight. The volatiles were removed under pressure and the residue was purified through recrystallization by using EtOAc/Hexane to afford tert-butyl (1-carbamoyl-3,3-difluorocyclobutyl)carbamate (8.7 g, 99% yield).

Step 3

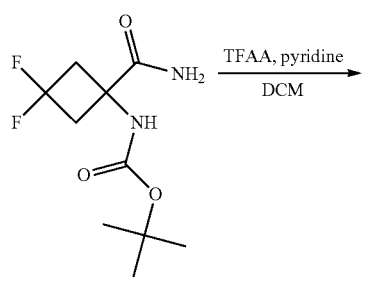

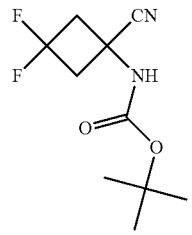

To a solution of tert-butyl (1-carbamoyl-3,3-difluorocyclobutyl)carbamate (8.7 g, 34.77 mmol) in DCM (50 ml) was added pyridine (11 g, 139.06 mmol) at 0° C. Then, trifluoroacetic anhydride (14.60 g, 39.53 mmol) was added dropwise to reaction mixture at the same temperature. The resulting mixture was warmed to RT and stirred for 2 h. The volatiles were removed under reduced pressure and the residue was purified through recrystallization by using EA/Hexane affording tert-butyl (1-cyano-3,3-difluorocyclobutyl)carbamate (6.52 g, 81% yield).

Step 4

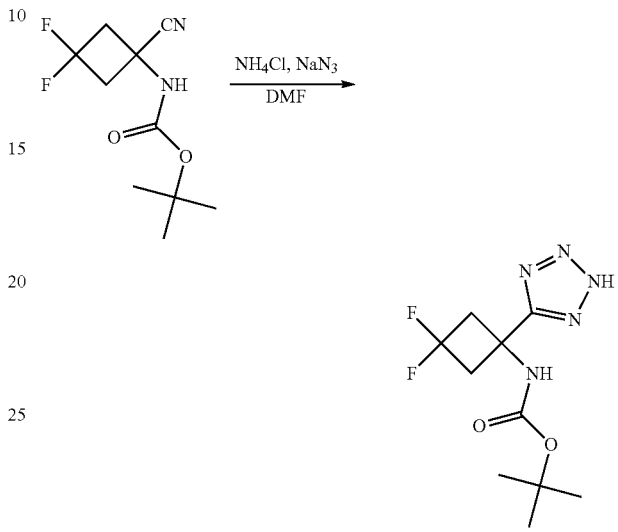

To a solution of tert-butyl (1-cyano-3,3-difluorocyclobutyl)carbamate (500 mg, 2.15 mmol) in DMF (10 mL) was added ammonium (575 mg, 10.77 mmol) and sodium azide (699 mg, 10.77 mmol) and the reaction mixture was heated at 100° C. for 3 h. The reaction mixture was cooled to room temperature and filtered over decalite®, washed with DMF (2 mL) and concentrated to dryness. The residue was purified using silica gel column chromatography (ethyl acetate in heptane from 0 to 100%) to afford tert-butyl (3,3-difluoro-1-(2H-tetrazol-5-yl)cyclobutyl)carbamate (400 mg, yield 67%) as white powder Step 5

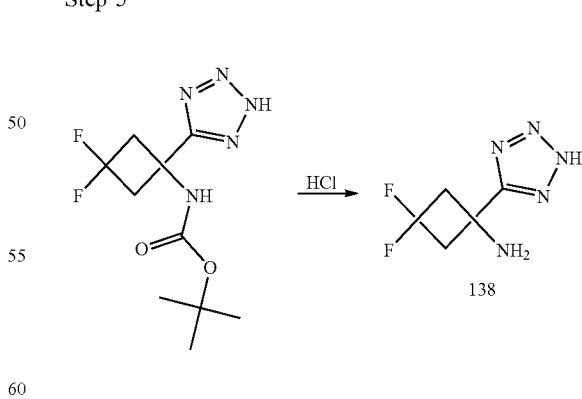

138

Tert-butyl (3,3-difluoro-1-(2H-tetrazol-5-yl)cyclobutyl) carbamate was dissolved in DCM/ethyl acetate (10 mL/5 mL) and HCl (1.82 mL, 4 M in dioxane, 7.27 mmol) was added. The reaction mixture was stirred at room temperature for 3 days. The resulting suspension was filtered and the solid was washed with DCM to afford intermediate I38 (132 mg, 85%) as white solid.

Synthesis of Intermediate I40c

Step 1

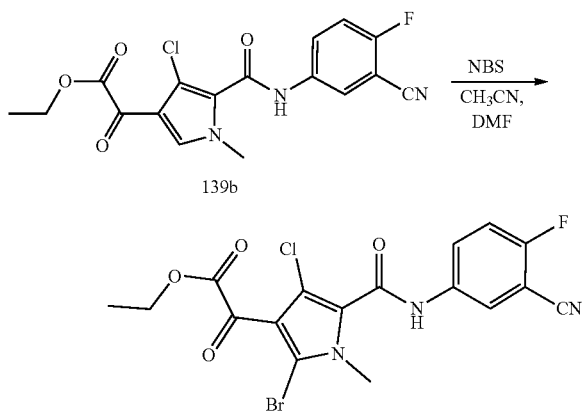

Intermediate I39b (1.8 g, 4.765 mmol) was suspended in acetonitrile (32 mL) and DMF (16 mL). NBS (1.3 g, 7.15 mmol) was added and the mixture was stirred at RT for 2 h. The acetonitrile was distilled off. The residue was added dropwise to ice water. The precipitate was filtered off and washed with water. The product was dried under vacuum afford ethyl 2-(2-bromo-4-chloro-5-((3-cyano-4-fluorophenyl)carbamoyl)-1-methyl-1H-pyrrol-3-yl)-2-oxoacetate (1.8 g, yield 83%) as a pale yellow solid which was used as such in the step.

Step 2

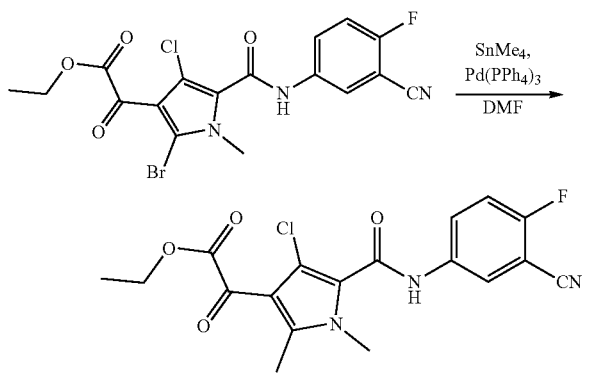

A solution of ethyl 2-(2-bromo-4-chloro-5-((3-cyano-4-fluorophenyl)carbamoyl)-1-methyl-1H-pyrrol-3-yl)-2-oxoacetate (250 mg, 0.55 mmol), tetramethyltin (159 µL, 1.09 mmol) DMF (2.5 mL) was purged with nitrogen during 5 minutes. Tetrakis(triphenylphosphine)palladium (63 mg, 0.055 mmol) was added and the reaction mixture was irradiated at 140° C. during 30 min in a microwave. The rm was concentrated. The residue was purified by silica column chromatography (EtOAc/heptane 0/100 to 100/0). The product fractions were concentrated, and the resulting product triturated in DIPE, filtered off and dried under vacuum to afford ethyl 2-(4-chloro-5-((3-cyano-4-fluorophenyl)carbamoyl)-1,2-dimethyl-1H-pyrrol-3-yl)-2-oxoacetate (156 mg, yield 72%) as an off white solid.

Step 3

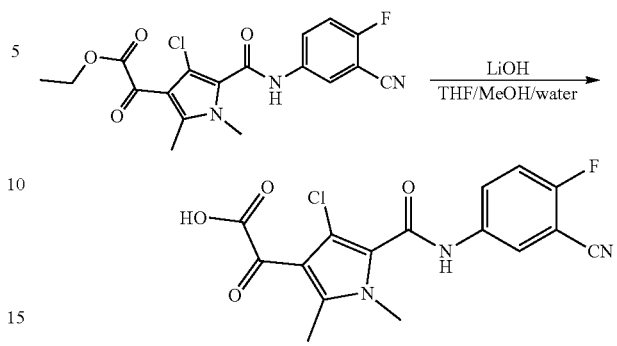

Ethyl 2-(4-chloro-5-((3-cyano-4-fluorophenyl)carbamoyl)-1,2-dimethyl-1H-pyrrol-3-yl)-2-oxoacetate (156 mg, 0.4 mmol) in THF (10 mL), MeOH (10 mL) and water(10 mL) was treated with LiOH (1.19 mL, 1 M in water, 1.19 mmol) and the reaction mixture was stirred at RT for 24 hours. HCl (1.19 mL, 1 M in H₂O, 1.19 mmol) was added and the resulting mixture was evaporated until only water remained. The aqueous layer was extracted using EtOAc (3×50 mL). The combined organics were dried on Na₂SO₄, filtered and concentrated under reduced pressure yielding intermediate I40c which was used as such in the next step.

Synthesis of Final Compounds

Synthesis of Compound 1

N-(4-Fluoro-3-methylphenyl)-1-methyl-4-(oxo{[1-(2H-1,2,3-triazol-4-yl)ethyl]amino}acetyl)-1H-pyrrole-2-carboxamide

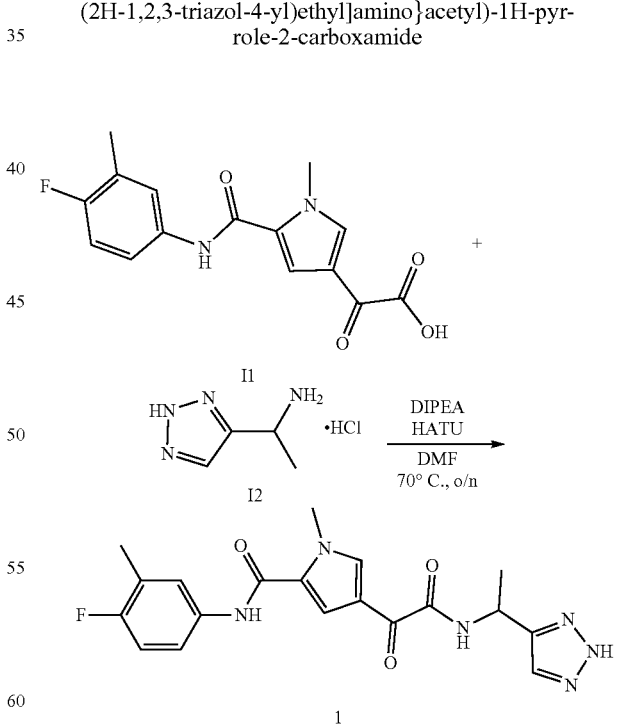

Intermediate I1 (150 mg, 0.47 mmol, 96% purity), intermediate I2 (186 mg, 1.66 mmol), DIPEA (0.41 mL, 2.37 mmol) and HATU (234 mg, 0.62 mmol) were dissolved in DMF (5 mL). The reaction mixture was stirred at 70° C. overnight. The reaction mixture was loaded on a silica cartridge and the product was eluted with a gradient from heptane to (EtOAc:EtOH) (3:1). The obtained residue was purified by silica column chromatography (heptane/EtOAc). A third purification was performed via preparative HPLC (Stationary phase: RP XBridge Prep C18 OBD-10 μm, 50×150 mm, mobile phase: $NH_4HCO_3$ (0.25% in $H_2O$)/ $CH_3CN$) to afford Compound 1 (49.9 mg, 26%).

$^1$H NMR (400 MHz, DMSO-$d_6$) δ ppm 14.51-15.11 (m, 1H), 10.05 (s, 1H), 8.99-9.12 (m, 1H), 8.15 (br d, J=1.3 Hz, 1H), 7.62-7.80 (m, 3H), 7.48-7.57 (m, 1H), 7.09 (t, J=9.2 Hz, 1H), 5.17-5.29 (m, 1H), 3.95 (s, 3H), 2.23 (d, J=1.8 Hz, 3H), 1.52 (d, J=7.0 Hz, 3H); LCMS (method A): Rt=0.85 min; mass calcd. for $C_{19}H_{19}FN_6O_3$ 398.2, m/z found 399.2 $[M+H]^+$ Synthesis of Compound 2

4-[{[3,3-Difluoro-1-(2H-1,2,3-triazol-4-yl)cyclobutyl]amino}(oxo)acetyl]-N-(4-fluoro-3-methylphenyl)-1-methyl-1H-pyrrole-2-carboxamide

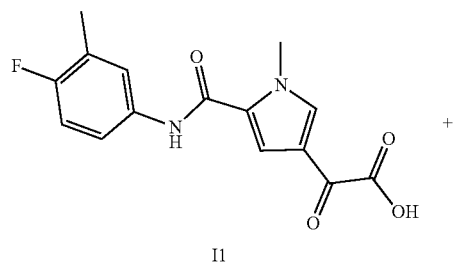

I1

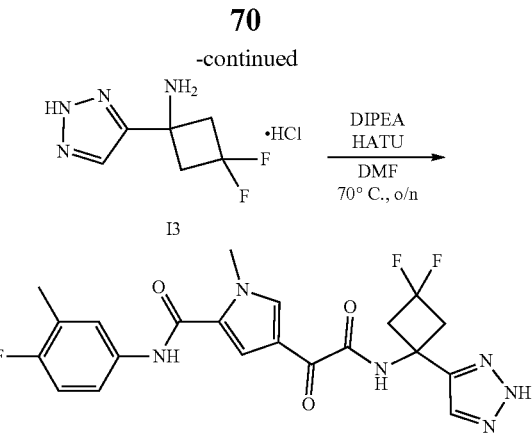

Compound 2 (143 mg, 65%) was synthesized according to the procedure reported for the synthesis of Compound 1.

$^1$H NMR (400 MHz, DMSO-$d_6$) δ ppm 14.43-15.42 (m, 1H), 10.05 (s, 1H), 9.74 (s, 1H), 8.13 (d, J=1.3 Hz, 1H), 7.72-7.92 (m, 1H), 7.62-7.70 (m, 2H), 7.50-7.57 (m, 1H), 7.09 (t, J=9.2 Hz, 1H), 3.94 (s, 3H), 3.33-3.44 (m, 2H), 3.19-3.29 (m, 2H), 2.23 (d, J=1.8 Hz, 3H); LCMS (method A): Rt=0.94 min; mass calcd. for $C_{21}H_{19}F_3N_6O_3$ 460.2, m/z found 461.2 $[M+H]^+$ Unless otherwise indicated, the compounds in the table below were synthetized according to the procedure reported for compound 1.

| Cmpd no. | Structure | Coupling partner 1 | Coupling partner 2 | Isolated yield (%) |
|---|---|---|---|---|
| 9 | 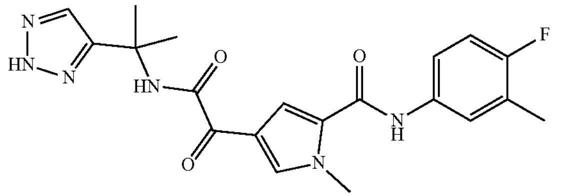 [SMILES: Cc1cc(NC(=O)c2cc(C(=O)C(=O)NC(C)(C)c3cn[nH]n3)cn2C)ccc1F] | I1 | [1088886-66-1] | 13 |
| 8 | 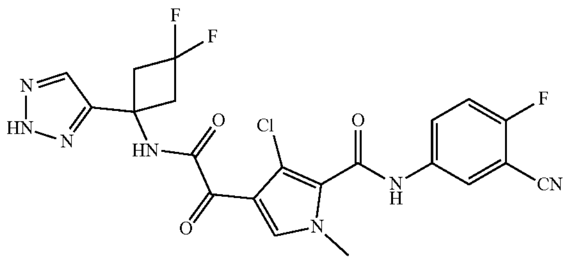 [SMILES: Cn1cc(C(=O)C(=O)NC2(c3cn[nH]n3)CC(F)(F)C2)c(Cl)c1C(=O)Nc1ccc(F)c(C#N)c1] | I39c | I3 | 54 |
| 7 | 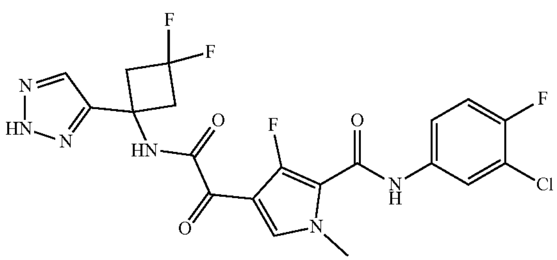 | I4c | I3 | 21 |
| 3 | 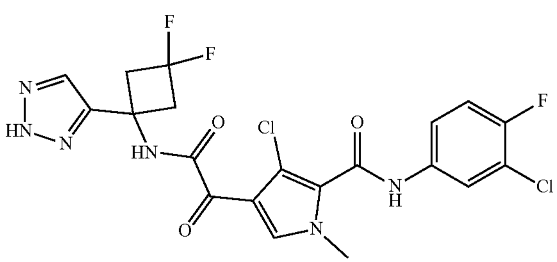 | I5c | I3 | 33 |

| Cmpd no. | Structure | Coupling partner 1 | Coupling partner 2 | Isolated yield (%) |
|---|---|---|---|---|
| 5 | 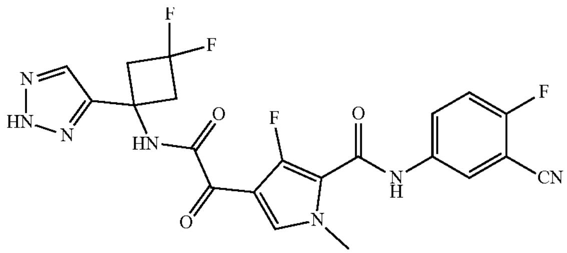 [SMILES: Cn1cc(C(=O)C(=O)NC2(c3cn[nH]n3)CC(F)(F)C2)c(F)c1C(=O)Nc1ccc(F)c(C#N)c1] | I6c | I3 | 49 |
| 4 | 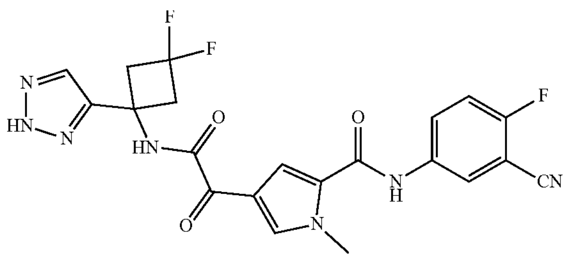 [SMILES: Cn1cc(C(=O)C(=O)NC2(c3cn[nH]n3)CC(F)(F)C2)cc1C(=O)Nc1ccc(F)c(C#N)c1] | I7c | I3 | 40 |
| 6 | 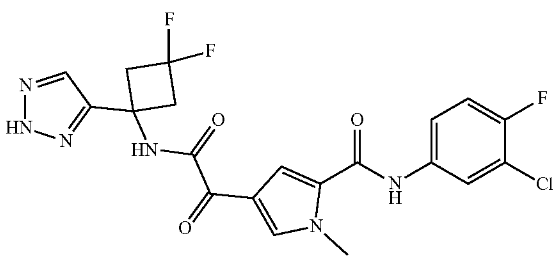 [SMILES: Cn1cc(C(=O)C(=O)NC2(c3cn[nH]n3)CC(F)(F)C2)cc1C(=O)Nc1ccc(F)c(Cl)c1] | I9c | I3 | 33 |
| 12 | 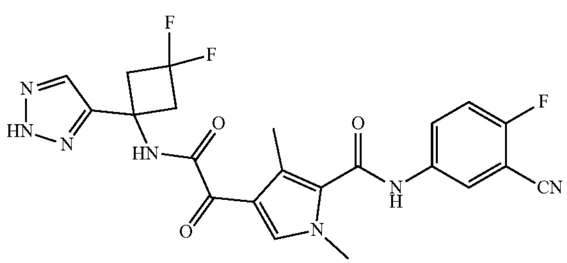 [SMILES: Cc1c(C(=O)C(=O)NC2(c3cn[nH]n3)CC(F)(F)C2)cn(C)c1C(=O)Nc1ccc(F)c(C#N)c1] | I9c | I3 | 6 |

| Cmpd no. | Structure | Coupling partner 1 | Coupling partner 2 | Isolated yield (%) |
|---|---|---|---|---|
| 13 | 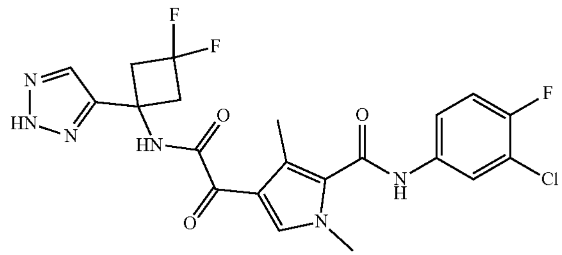 | I10c | I3 | 15 |
| 10 | 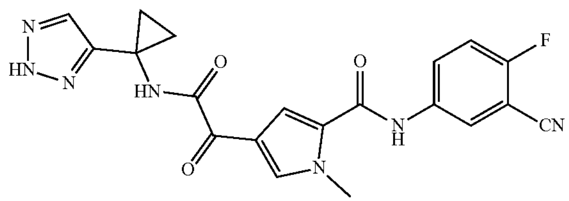 [SMILES: Cn1cc(C(=O)C(=O)NC2(c3cn[nH]n3)CC2)cc1C(=O)Nc1ccc(F)c(C#N)c1] | I7c | [2193057-59-4] | 36 |
| 11 | 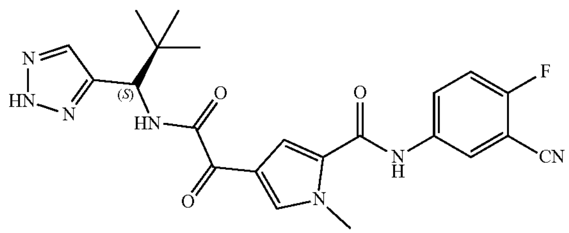 | I7c | I28 | 48 |
| 17 | 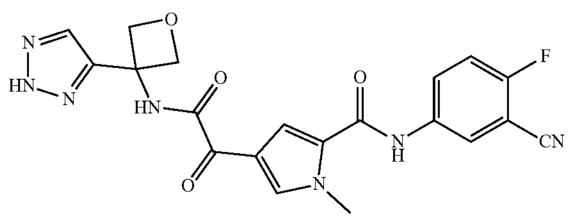 [SMILES: Cn1cc(C(=O)C(=O)NC2(c3cn[nH]n3)COC2)cc1C(=O)Nc1ccc(F)c(C#N)c1] | I7c | I27 | 15 |

-continued

| Cmpd no. | Structure | Coupling partner 1 | Coupling partner 2 | Isolated yield (%) |
|---|---|---|---|---|
| 18RS | 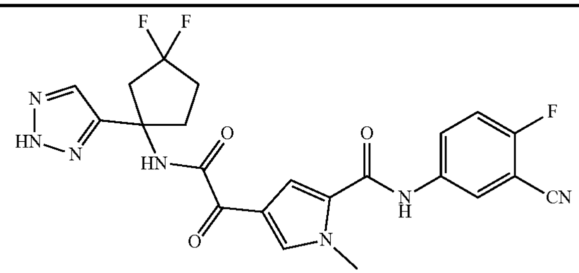 | I7c | I24 | 92 |
| 20RS | 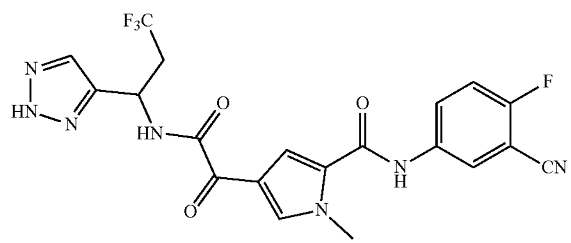 [SMILES: Cn1cc(C(=O)C(=O)NC(CC(F)(F)F)c2cn[nH]n2)cc1C(=O)Nc1ccc(F)c(C#N)c1] | I7c | I25 | 31 |
| 21 | 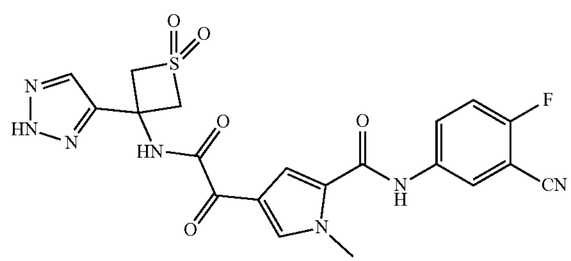 [SMILES: Cn1cc(C(=O)C(=O)NC2(c3cn[nH]n3)CS(=O)(=O)C2)cc1C(=O)Nc1ccc(F)c(C#N)c1] | I7c | I26 | 36 |
| 22 | 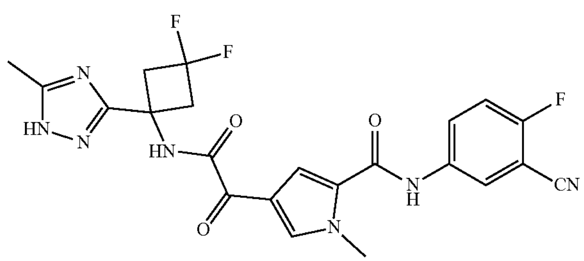 [SMILES: Cc1nc(C2(NC(=O)C(=O)c3cc(C(=O)Nc4ccc(F)c(C#N)c4)n(C)c3)CC(F)(F)C2)n[nH]1] | I7c | I35 | 39 |

-continued

| Cmpd no. | Structure | Coupling partner 1 | Coupling partner 2 | Isolated yield (%) |
|---|---|---|---|---|
| 23 | 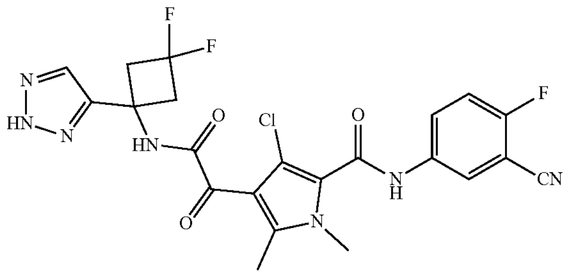 [SMILES: Cc1c(C(=O)C(=O)NC2(c3cn[nH]n3)CC(F)(F)C2)c(Cl)c(C(=O)Nc2ccc(F)c(C#N)c2)n1C] | I40c | I3 | 36 |
| 24RS | 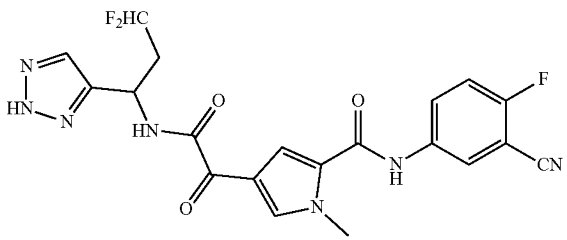 [SMILES: Cn1cc(C(=O)C(=O)NC(CC(F)F)c2cn[nH]n2)cc1C(=O)Nc1ccc(F)c(C#N)c1] | I7c | I29 | 44 |
| 25RS | 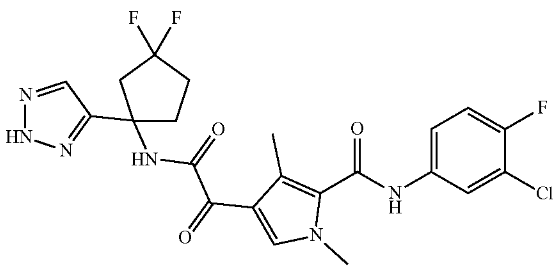 [SMILES: Cc1c(C(=O)C(=O)NC2(c3cn[nH]n3)CCC(F)(F)C2)cn(C)c1C(=O)Nc1ccc(F)c(Cl)c1] | I10c | I24 | 36 |
| 26RS | 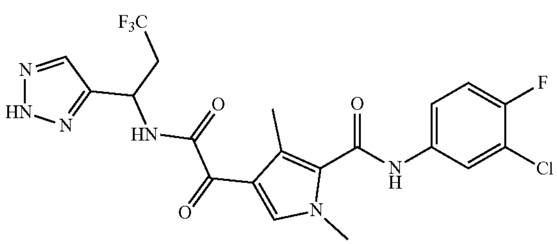 [SMILES: Cc1c(C(=O)C(=O)NC(CC(F)(F)F)c2cn[nH]n2)cn(C)c1C(=O)Nc1ccc(F)c(Cl)c1] | I10c | I25 | 86 |

| Cmpd no. | Structure | Coupling partner 1 | Coupling partner 2 | Isolated yield (%) |
|---|---|---|---|---|
| 27*RS*RS | 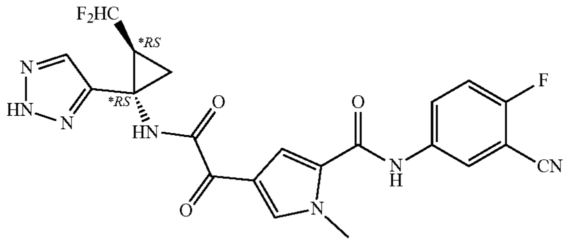 [SMILES: Cn1cc(C(=O)C(=O)N[C@@]2(c3cn[nH]n3)C[C@@H]2C(F)F)cc1C(=O)Nc1ccc(F)c(C#N)c1] | I7c | I37 | 50 |
| 28 | 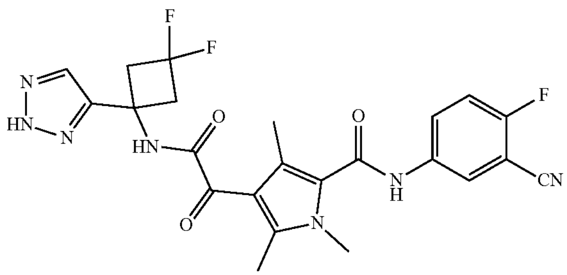 [SMILES: Cc1c(C(=O)C(=O)NC2(c3cn[nH]n3)CC(F)(F)C2)c(C)n(C)c1C(=O)Nc1ccc(F)c(C#N)c1] | I14c | I3 | 55 |
| 29 | 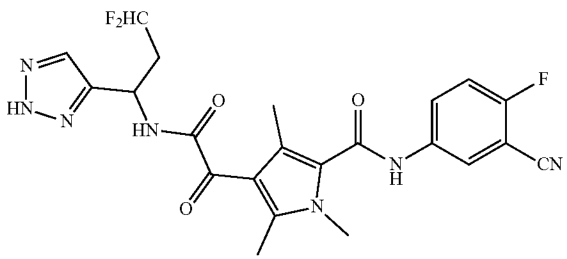 [SMILES: Cc1c(C(=O)C(=O)NC(CC(F)F)c2cn[nH]n2)c(C)n(C)c1C(=O)Nc1ccc(F)c(C#N)c1] | I14c | I29 | 34 |
| 30 | 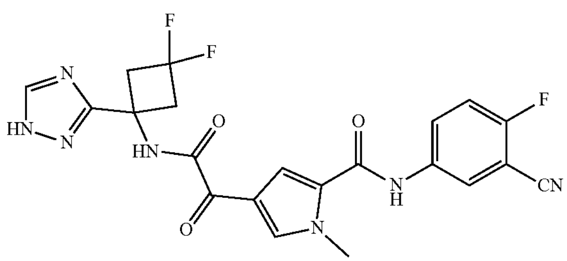 [SMILES: Cn1cc(C(=O)C(=O)NC2(c3nc[nH]n3)CC(F)(F)C2)cc1C(=O)Nc1ccc(F)c(C#N)c1] | I7c | I36 | 47 |

-continued

| Cmpd no. | Structure | Coupling partner 1 | Coupling partner 2 | Isolated yield (%) |
|---|---|---|---|---|
| 31 | 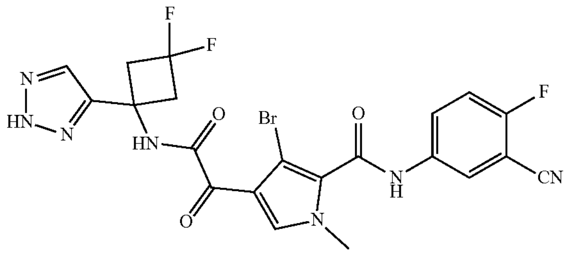 [SMILES: Cn1cc(C(=O)C(=O)NC2(c3cn[nH]n3)CC(F)(F)C2)c(Br)c1C(=O)Nc1ccc(F)c(C#N)c1] | I11c | I3 | 76 |
| 32 | 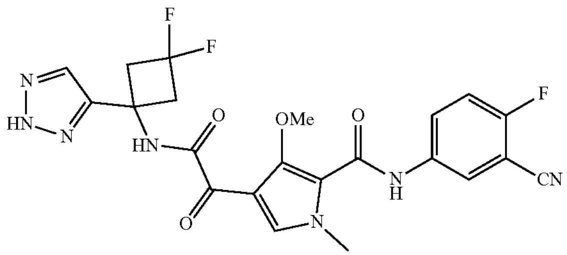 [SMILES: COc1c(C(=O)C(=O)NC2(c3cn[nH]n3)CC(F)(F)C2)cn(C)c1C(=O)Nc1ccc(F)c(C#N)c1] | I12c | I3 | 70 |
| 34 | 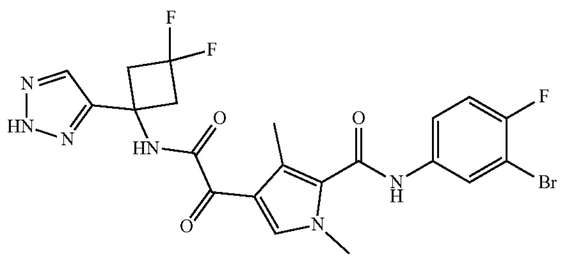 | I13c | I3 | 33 |
| 36 | 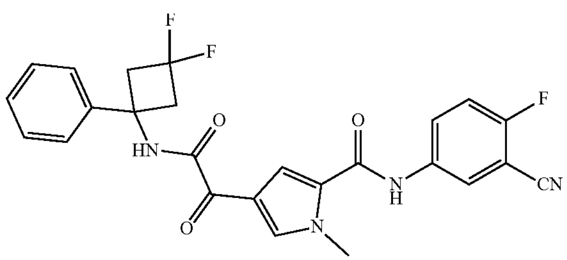 [SMILES: Cn1cc(C(=O)C(=O)NC2(c3ccccc3)CC(F)(F)C2)cc1C(=O)Nc1ccc(F)c(C#N)c1] | I7c | [1803589-73-2] | 62 |

-continued

| Cmpd no. | Structure | Coupling partner 1 | Coupling partner 2 | Isolated yield (%) |
|---|---|---|---|---|
| 38 | 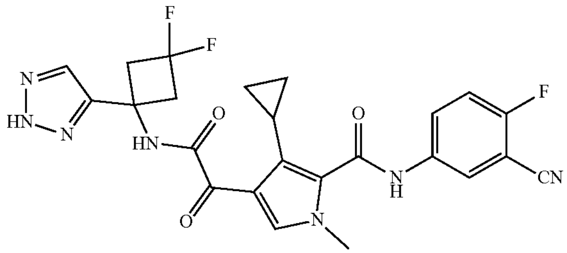 [SMILES: Cn1cc(C(=O)C(=O)NC2(c3cn[nH]n3)CC(F)(F)C2)c(C2CC2)c1C(=O)Nc1ccc(F)c(C#N)c1] | I16c | I3 | 44 |
| 39 | 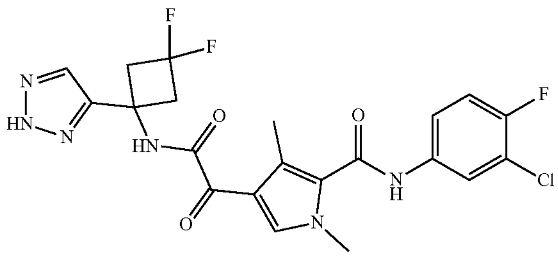 [SMILES: Cc1c(C(=O)C(=O)NC2(c3cn[nH]n3)CC(F)(F)C2)cn(C)c1C(=O)Nc1ccc(F)c(Cl)c1] | I10c | I3 | 59 |
| 40 | 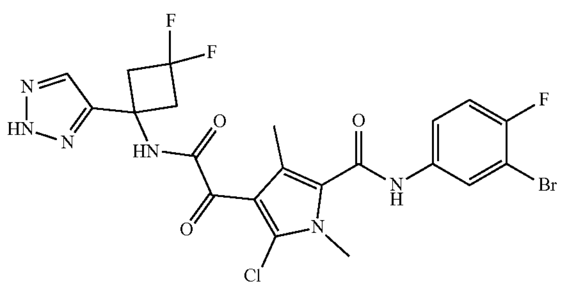 [SMILES: Cc1c(C(=O)C(=O)NC2(c3cn[nH]n3)CC(F)(F)C2)c(Cl)n(C)c1C(=O)Nc1ccc(F)c(Br)c1] | I23c | I3 | 11 |

| Cmpd no. | Structure | Coupling partner 1 | Coupling partner 2 | Isolated yield (%) |
|---|---|---|---|---|
| 41 | 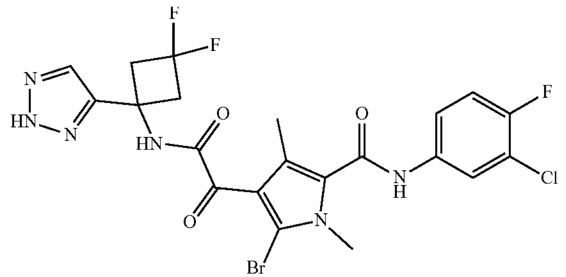 | I17c | I3 | 2 |
| 42* | | I21c | I3 | 67 |
| 43 | 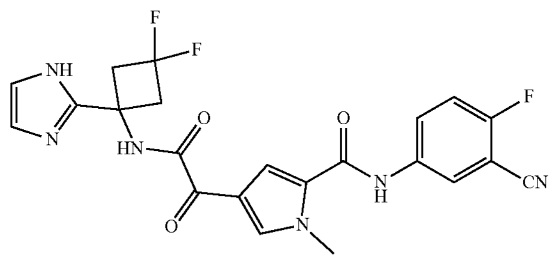 [SMILES: Cn1cc(C(=O)C(=O)NC2(c3ncc[nH]3)CC(F)(F)C2)cc1C(=O)Nc1ccc(F)c(C#N)c1] | I7c | [2228133-69-3] | 25 |

-continued

| Cmpd no. | Structure | Coupling partner 1 | Coupling partner 2 | Isolated yield (%) |
|---|---|---|---|---|
| 44RS | 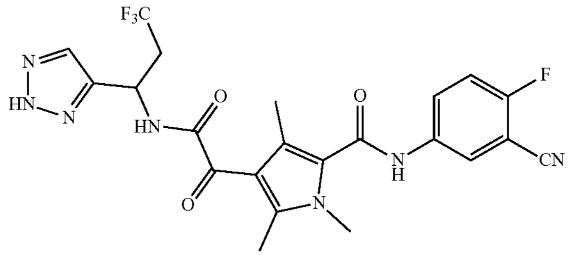 [SMILES: Cc1c(C(=O)C(=O)NC(CC(F)(F)F)c2cn[nH]n2)c(C)n(C)c1C(=O)Nc1ccc(F)c(C#N)c1] | I14c | I25 | 38 |
| 45 | 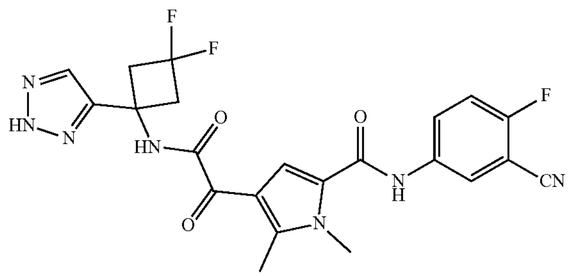 [SMILES: Cc1c(C(=O)C(=O)NC2(c3cn[nH]n3)CC(F)(F)C2)cc(C(=O)Nc2ccc(F)c(C#N)c2)n1C] | I25c | I3 | 62 |
| 47RS# | | I9c | I25 | Directly engaged in SFC separation |
| 48RS# | | I9c | I30 | Directly engaged in SFC separation |

-continued
| Cmpd no. | Structure | Coupling partner 1 | Coupling partner 2 | Isolated yield (%) |
|---|---|---|---|---|
| 49RS# | 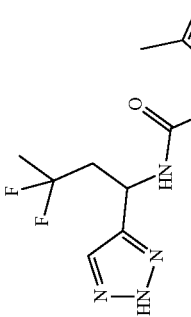 | 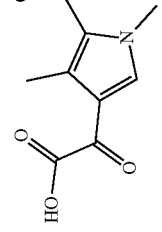 I9c | 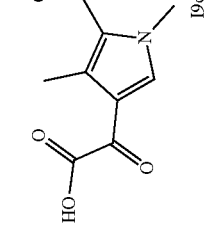 I31 | Directly engaged in SFC separation |
| 58# | 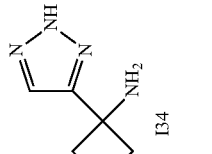 | 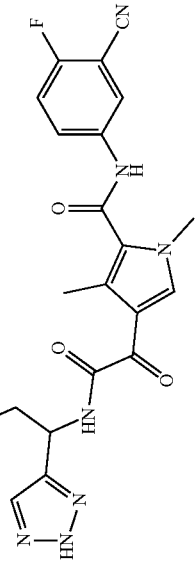 I9c | 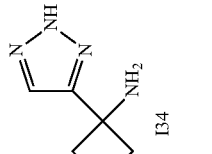 I34 | 73 |
| 50 | 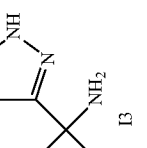 | 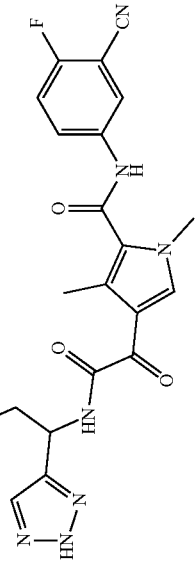 I19c | 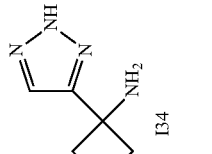 I3 | 15 |

-continued

| Cmpd no. | Structure | Coupling partner 1 | Coupling partner 2 | Isolated yield (%) |
|---|---|---|---|---|
| 51* | | I9c | I32 | 17 |
| 52* | | I20c | I3 | 36 |
| 54 | | I22c | I3 | 17 |

-continued

| Cmpd no. | Structure | Coupling partner 1 | Coupling partner 2 | Isolated yield (%) |
|---|---|---|---|---|
| 57 | 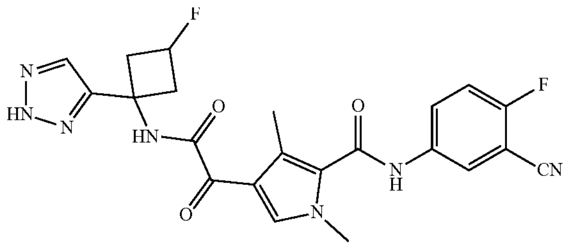 [SMILES: Cc1c(C(=O)C(=O)NC2(c3cn[nH]n3)CC(F)C2)cn(C)c1C(=O)Nc1ccc(F)c(C#N)c1] | I9c | I33 | Directly engaged in SFC separation |
| 56 | 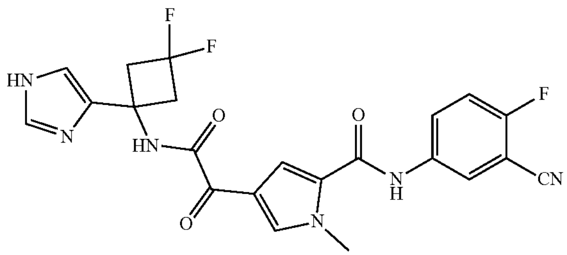 [SMILES: Cn1cc(C(=O)C(=O)NC2(c3c[nH]cn3)CC(F)(F)C2)cc1C(=O)Nc1ccc(F)c(C#N)c1] | I7c | [2229306-83-4] | 5 |
| Ref. 59 | 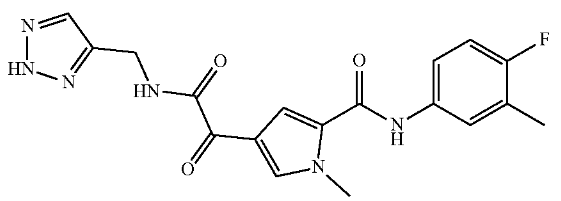 [SMILES: Cc1cc(NC(=O)c2cc(C(=O)C(=O)NCc3cn[nH]n3)cn2C)ccc1F] | | [1009101-70-5] HCl | 20 |

Synthesis of Compounds 14-16

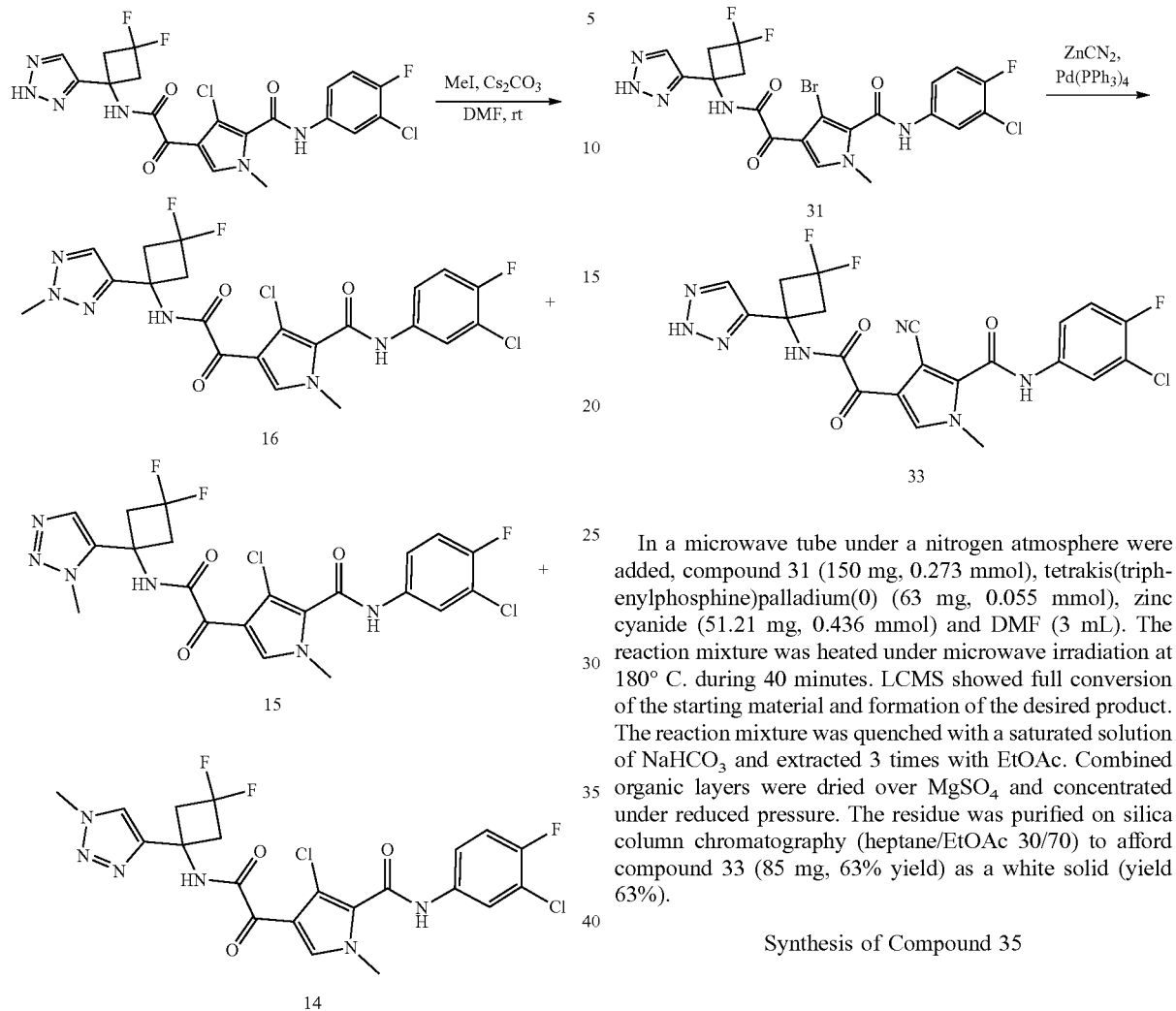

To a solution of compound 3 (120 mg, 0.23 mmol) in DMF (1 mL) was added Cs$_2$CO$_3$ (56.91 mg, 0.17 mmol) and MeI (14.5 μL, 0.23 mmol) in DMF (100 μl). The reaction mixture was stirred at room temperature for 1 hour. The reaction mixture was poured into water (10 mL). The white solid was filtered and washed with water (2×1 mL). The solid was dried and purified using silica gel column chromatography (ethyl acetate/heptane from 0/100 to 100/0) to afford

- A first compound which was suspended in methanol, concentrated to dryness to afford compound 16 as white powder (81 mg, yield 65%)
- A second compound 14 (37 mg, yield 30%).
- A third residue which was further purified by preparative SFC (Stationary phase: Chiralcel Diacel OJ 20×250 mm, Mobile phase: CO$_2$, EtOH+0.4 iPrNH$_2$) yielding compound 15 (7 mg, yield 7%)

Synthesis of Compound 33

In a microwave tube under a nitrogen atmosphere were added, compound 31 (150 mg, 0.273 mmol), tetrakis(triphenylphosphine)palladium(0) (63 mg, 0.055 mmol), zinc cyanide (51.21 mg, 0.436 mmol) and DMF (3 mL). The reaction mixture was heated under microwave irradiation at 180° C. during 40 minutes. LCMS showed full conversion of the starting material and formation of the desired product. The reaction mixture was quenched with a saturated solution of NaHCO$_3$ and extracted 3 times with EtOAc. Combined organic layers were dried over MgSO$_4$ and concentrated under reduced pressure. The residue was purified on silica column chromatography (heptane/EtOAc 30/70) to afford compound 33 (85 mg, 63% yield) as a white solid (yield 63%).

Synthesis of Compound 35

Compound 13 (30 mg, 0.059 mmol) was dissolved in acetonitrile (0.4 mL) and DMF (0.2 mL). Trifluoromethanesulfonic acid (8 μL, 0.0882 mmol) was added. N-chlorosuccinimide (7.8 mg, 0.059 mmol) was added at 0° C. The reaction mixture was stirred at 0° C. for 30 min and then 2 hours at RT. Additional N-chlorosuccinimide (4 mg) was added and the reaction mixture was stirred for 1 additional hour. LCMS showed completion of the reaction. The mixture was quenched with water and extracted with DCM (3×), and washed with brine, dried (Na$_2$SO$_4$), filtered and concentrated in vacuo. The residue was purified by preparative SFC (Stationary phase: Chiralpak Diacel AD 20×250 mm, Mobile phase: CO$_2$, iPrOH+0.4 iPrNH$_2$) to afford compound 35 (9 mg, 28%) as a white solid.

Synthesis of compound 37

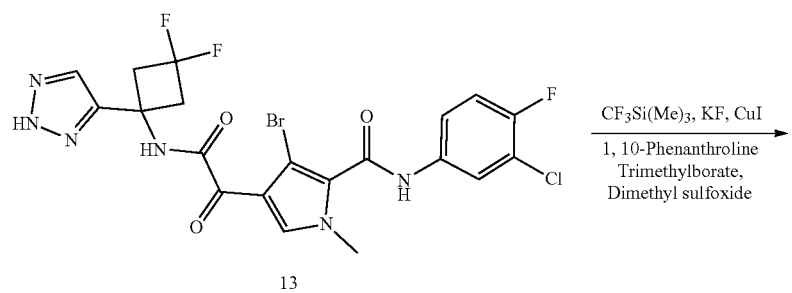

13

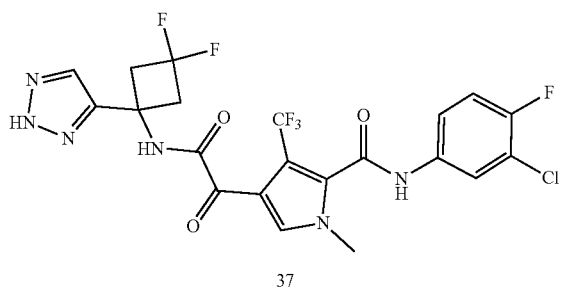

37

An oven-dried test tube with a septum cap and a stir bar was charged with compound 31 (100 mg, 0.182 mmol), potassium fluoride (31.67 mg, 0.545 mmol), copper iodide (6.92 mg, 0.036 mmol) and 1,10-phenanthroline (6.55 mg, 0.036 mmol), The reaction vessel was closed, then evacuated and refilled with nitrogen (bubbling). DMSO (1.0 mL), trimethyl borate (60.8 μL, 0.545 mmol) and (trifluoromethyl)trimethylsilane (80.5 μL, 0.545 mmol) were added via a syringe. The resulting suspension was stirred for 18 h at 60° C. The reaction mixture was quenched with a 1:1 mixture of NH$_3$ (25%)/NH$_4$Cl aq. sat. and extracted with EtOAc. The organic layer was then washed with water and the combined organic layers were dried over MgSO$_4$ and concentrated under reduced pressure. The crude residue was then purified by preparative HPLC (Stationary phase: RP XBridge Prep C18 OBD-5 μm,50×250 mm, Mobile phase: 0.25% NH$_4$CO$_3$ solution in water, CH$_3$CN) to afford compound 37 (9 mg, 9% yield).

Synthesis of Compound 46 and Compound 53
Step 1

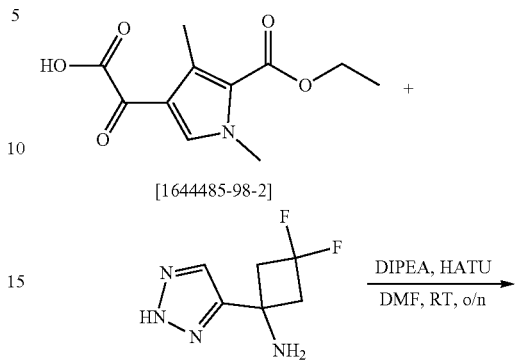

-continued

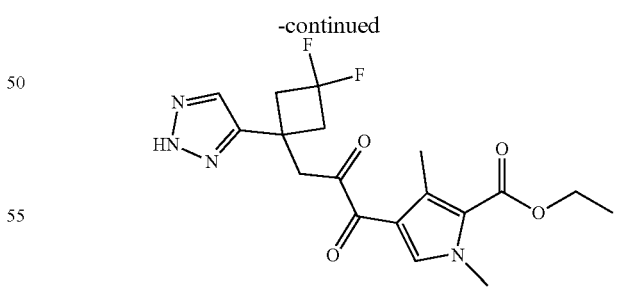

2-(5-(Ethoxycarbonyl)-1,4-dimethyl-1H-pyrrol-3-yl)-2-oxoacetic acid (3.0 g, 12.54 mmol), 3,3-difluoro-1-(2H-1,2,3-triazol-4-yl)cyclobutan-1-amine (2.77 g, 13.17 mmol) and HATU (5.72 g, 15.05 mmol) were dissolved in DMF (30 mL). DI PEA (8.64 mL, 16 mmol) was added dropwise and the resulting mixture was stirred for 16 hours at room temperature. The crude was poured on a silica plug and purified by silica column chromatography (heptane to EtOAc from 100/0 to 0/100). The desired fractions were concentrated in vacuo and dried in a vacuum oven at 55° C. for 24 hours yielding ethyl 4-(2-((3,3-difluoro-1-(2H-1,2,3-triazol-4-yl)cyclobutyl)amino)-2-oxoacetyl)-1,3-dimethyl-1H-pyrrole-2-carboxylate (4.5 g, yield 91%) which was used as such.

Step 2

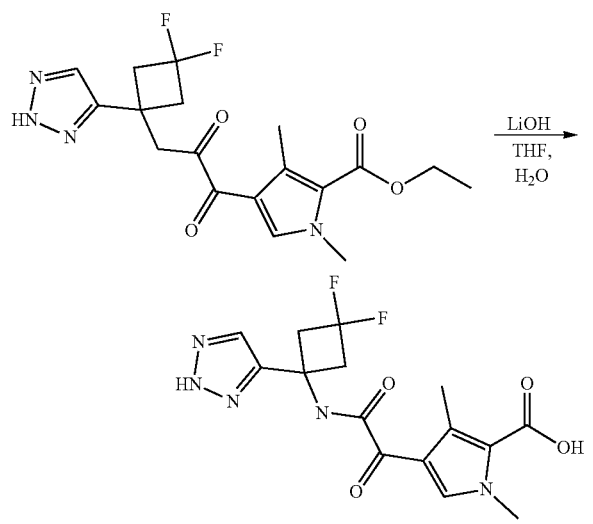

A aqueous solution of LiOH (62 mL, 1 M, 61.72 mmol) was added to a solution of ethyl 4-(2-((3,3-difluoro-1-(2H-1,2,3-triazol-4-yl)cyclobutyl)amino)-2-oxoacetyl)-1,3-dimethyl-1H-pyrrole-2-carboxylate (2.44 g, 6.17 mmol) in THF (20 mL, 246.86 mmol). This reaction mixture was stirred at RT for 16 hours. The solvents were evaporated until only water remained and the resulting aqueous residue was cooled to 0° C. and treated with HCl (1 M in $H_2O$) until pH~3. The aqueous layer was extracted with Me-THF (3×25 mL). The combined extracts were dried on $Na_2SO_4$, filtered and evaporated under reduced pressure to afford 4-(2-((3,3-difluoro-1-(2H-1,2,3-triazol-4-yl)cyclobutyl)amino)-2-oxoacetyl)-1,3-dimethyl-1H-pyrrole-2-carboxylic acid (1.65 g, yield 73%) as a white powder which was used as such.

Step 3

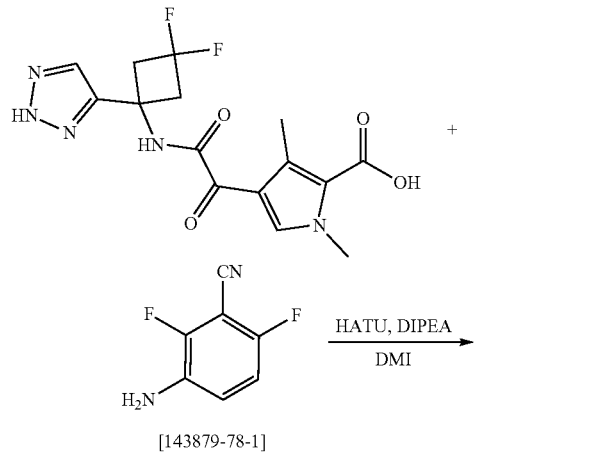

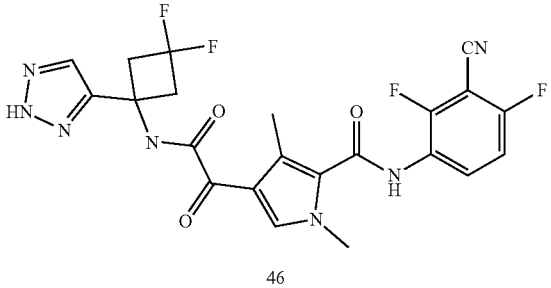

46

4-(2-((3,3-Difluoro-1-(2H-1,2,3-triazol-4-yl)cyclobutyl)amino)-2-oxoacetyl)-1,3-dimethyl-1H-pyrrole-2-carboxylic acid (100 mg, 0.27 mmol) was dissolved in 1,3-dimethyl-2-imidazolidinone (DMI) (2 mL). 3-Amino-2,6-difluorobenzonitrile (83.92 mg, 0.54 mmol), DIPEA (238 μL, 1.36 mmol) and HATU (155 mg, 0.41 mmol) were added. The mixture was stirred at 50° C. for 114 hours. LCMS showed 60% formation of desired product. The reaction mixture was heated at 90° C. for 3 hours. (full conversion observed) and poured into HCl (1 M in $H_2O$) (15 mL, 15 mmol). The resulting solid was filtered and purified using silica column chromatography (ethyl acetate in heptane from 0/100 to 100/0) yielding a first fraction as off-white powder. The filtrate was extracted with 2-MeTHF (3×10 mL) and the combine organic layers were washed with brine, concentrated under reduced pressure to afford a second fraction. Both fractions were further purified by preparative HPLC (Stationary phase: RP XBridge Prep C18 OBD-10 μm, 30×150 mm, Mobile phase: 0.25% $NH_4HCO_3$ solution in water, MeOH) to afford compound 46 (13 mg, yield 9%) as white solid.

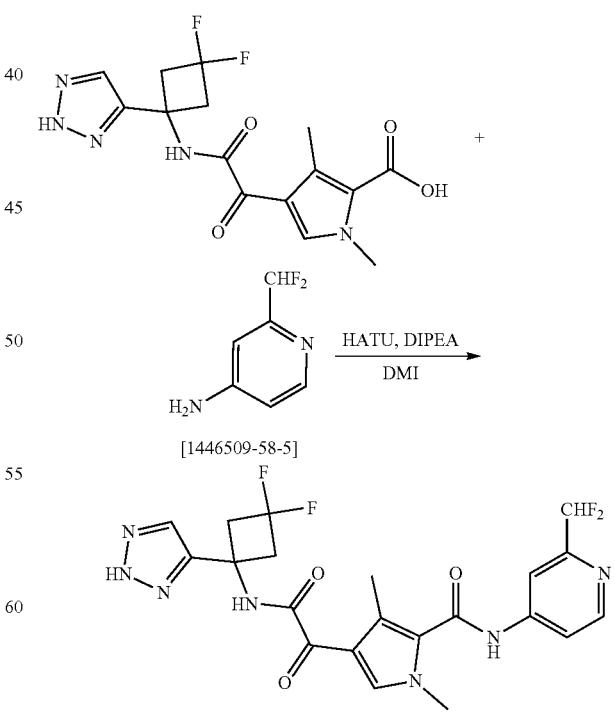

53

Compound 53 was synthesized in a similar manner as compound 46 using 2-(difluoromethyl)pyridin-4-amine (5.3 mg, yield 2%).

Synthesis of Compound 55

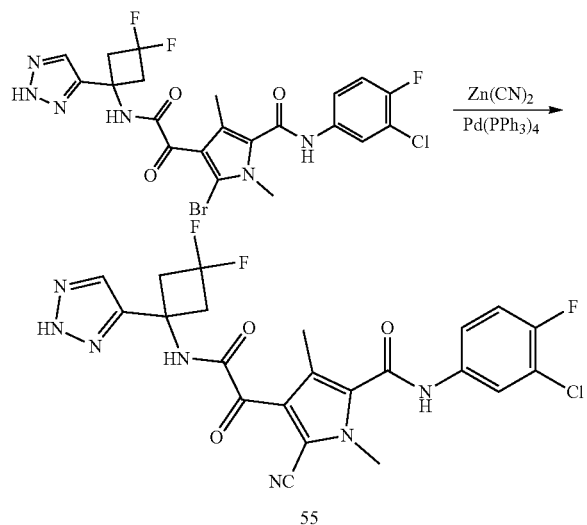

To a solution of compound 41 (110 mg, 0.192 mmol) in dry DMF (1 mL) was added zinc cyanide (45 mg, 0.38 mmol). The resulting solution was degassed for 5 min with nitrogen and tetrakis(triphenylphosphine)palladium(0) (18 mg, 0.015 mmol) was added. The reaction mixture was sealed and heated in a microwave at 120° C. for 60 min. LCMS indicated a ratio 1:1 starting material:desired compound. Once cooled to room temperature, the reaction was concentrated under reduced pressure. The resulting residue was dissolved in DCM and sat. aq. $NH_4Cl$ was added. The two layers were separated and the aqueous layer was extracted with DCM. The combined organic layers were washed with brine, dried over $MgSO_4$, filtered and concentrated under reduced pressure. The crude was purified by preparative SFC (Stationary phase: Chiralpak Diacel ID 20×250 mm, Mobile phase: $CO_2$, EtOH+0.4 $iPrNH_2$) followed by preparative HPLC (Stationary phase: RP XBridge Prep C18 OBD-5 μm,50×250 mm, Mobile phase: 0.25% $NH_4HCO_3$ solution in water, $CH_3CN$) yielding compound 55 (4.5 mg, 5%) as a yellow fluffy solid.

Chiral compounds below were obtained by SPC separation of the corresponding mixture.

Prep SFC (Stationary phase: Chiralpak Daicel IG 20×250 mm, Mobile phase: $CO_2$, MeOH-iPrOH or iPrOH or MeOH (50-50)+0.4% iPrNH2)

| Final compound | | Origin |
|---|---|---|
| 18*R | 18*S | 18RS |
| 24*R | 24*S | 24RS |
| 25*R | 25*S | 25RS |

-continued
| Final compound | | Origin |
|---|---|---|
| 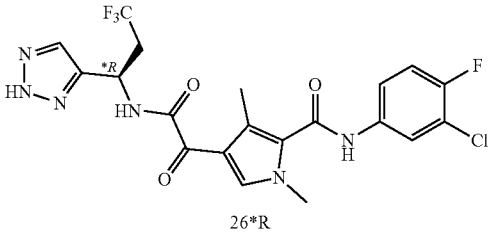 [SMILES: Cc1c(C(=O)C(=O)N[C@H](CC(F)(F)F)c2cn[nH]n2)cn(C)c1C(=O)Nc1ccc(F)c(Cl)c1]<br>26*R | 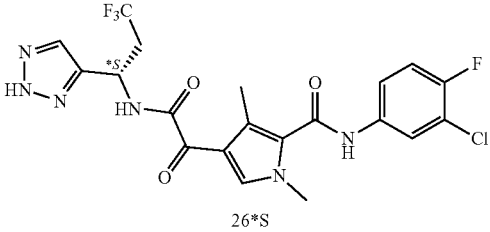 [SMILES: Cc1c(C(=O)C(=O)N[C@@H](CC(F)(F)F)c2cn[nH]n2)cn(C)c1C(=O)Nc1ccc(F)c(Cl)c1]<br>26*S | 26RS |
| 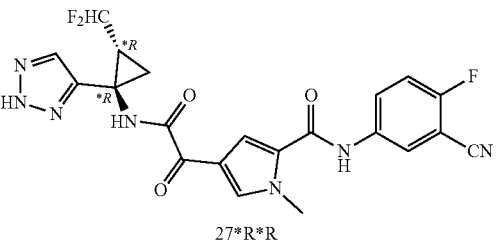 [SMILES: Cn1cc(C(=O)C(=O)N[C@]2(c3cn[nH]n3)C[C@H]2C(F)F)cc1C(=O)Nc1ccc(F)c(C#N)c1]<br>27*R*R | 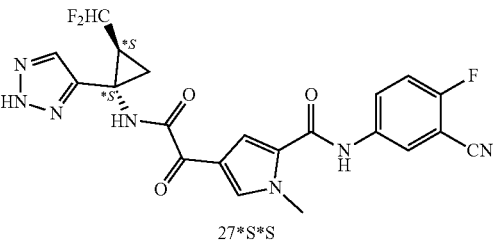 [SMILES: Cn1cc(C(=O)C(=O)N[C@@]2(c3cn[nH]n3)C[C@@H]2C(F)F)cc1C(=O)Nc1ccc(F)c(C#N)c1]<br>27*S*S | 27*RS*RS |
| 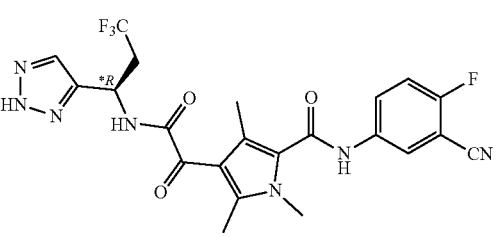<br>44*R | 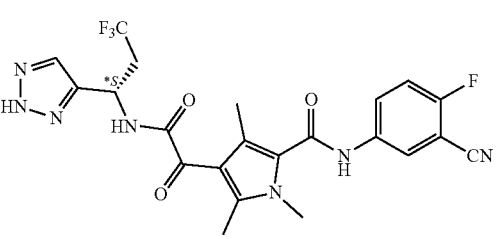<br>44*S | 44RS |
| 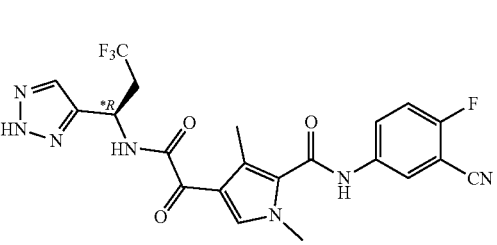<br>47*R | 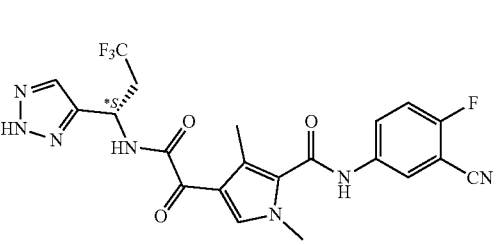<br>47*S | 47RS |
| 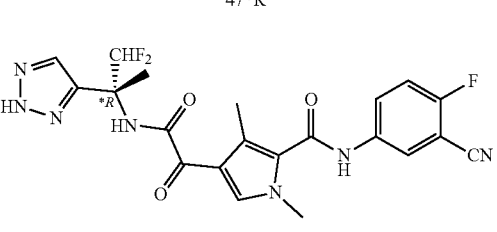<br>48*R | 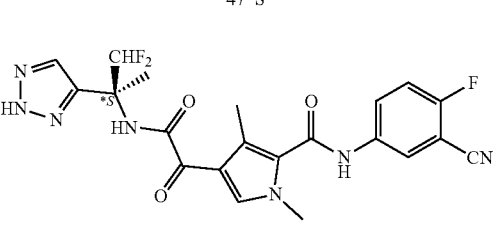<br>48*S | 48RS |
| 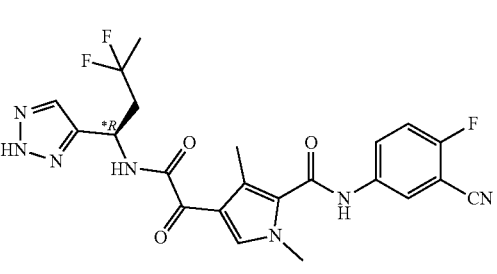<br>49*R | 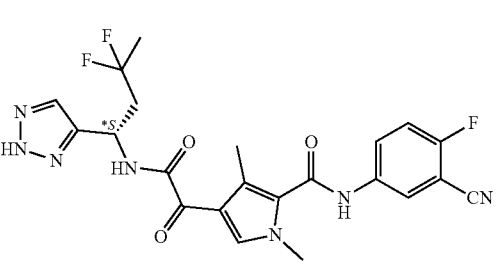<br>49*S | 49RS |

-continued

| Final compound | Origin |
|---|---|
| 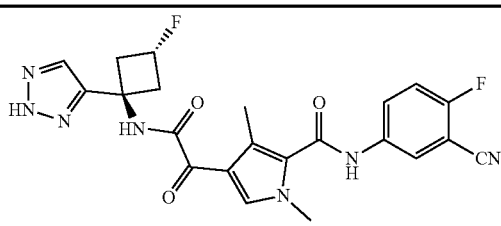 57tran     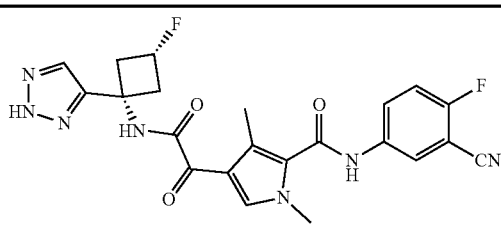 57cis | 57 |
| 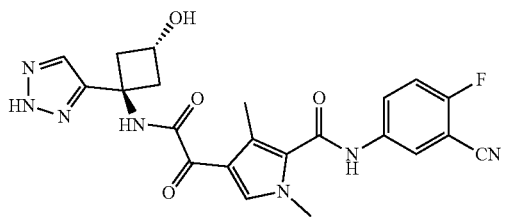 58tran     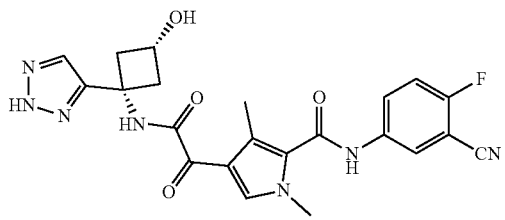 58cis | 58 |

TABLE 1

LCMS data

| Cmpd no | Rt (min) | [M + H]+ | [M − H]− | LCMS method |
|---|---|---|---|---|
| 9 | 1.76 | 413 | 411 | B |
| 8 | 0.94 | 506 | 504 | A |
| 7 | 1.03 | 499 | 497 | A |
| 3 | 1.05 | 515 | 513 | A |
| 5 | 0.92 | 490 | 488 | A |
| 4 | 0.88 | 472 | 470 | A |
| 6 | 1.02 | 481 | 479 | A |
| 14 | 2.00 | 529 | 527 | B |
| 16 | 1.15 | 529 | 527 | A |
| 15 | 1.95 | 529 | 527 | C |
| 12 | 1.77 | 486 | 484 | C |
| 13 | 1.83 | 495 | 493 | D |
| 10 | 0.81 | 422 | 420 | A |
| 11 | 0.97 | 452 | 450 | A |
| 17 | 0.76 | 438 | 436 | A |
| 18*R | 0.91 | 486 | 484 | A |
| 18*S | 0.91 | 486 | 484 | A |
| 20RS | 1.77 | 478 | 476 | B |
| 21 | 1.51 | / | 484 | B |
| 22 | 1.70 | 486 | 484 | B |
| 23 | 2.00 | 520 | 518 | E |
| 24RS | 2.00 | 460 | 458 | E |
| 25*R | 1.93 | 509 | 507 | B |
| 25*S | 1.93 | 509 | 507 | B |
| 26*R | 1.90 | 501 | 499 | C |
| 26*S | 1.90 | 501 | 499 | C |
| 27*S*S | 0.87 | 472 | 470 | A |
| 27*R*R | 0.87 | 472 | 470 | A |
| 24*R | 1.67 | 460 | 458 | C |
| 24*S | 1.67 | 460 | 458 | C |
| 28 | 0.87 | 500 | 498 | A |
| 29 | 0.84 | 488 | 486 | A |
| 30 | 0.87 | 472 | 470 | A |
| 31 | 1.79 | / | 548 | B |
| 32 | 9.90 | 502 | / | F |
| 33 | 1.70 | 497 | 495 | B |
| 34 | 2.01 | 539 | 537 | C |
| 35 | 0.99 | 529 | 527 | A |
| 36 | 2.14 | | 479 | B |
| 37 | 0.92 | 540 | 538 | A |
| 38 | 1.85 | 512 | 510 | B |
| 39 | 1.54 | 496 | 494 | B |
| 40 | 1.00 | / | 571 | A |
| 41 | 1.00 | 573 | / | A |
| 42 | 9.3 | 504 | / | F |
| 43 | 0.90 | 471 | 469 | A |
| 44RS | 0.89 | 506 | 504 | A |
| 45 | 1.79 | 486 | 484 | B |
| 46 | 1.74 | 504 | 502 | B |
| 47*R | 0.93 | 492 | 490 | A |
| 47*S | 0.93 | 492 | 490 | A |
| 48*R | 1.77 | 474 | 472 | B |
| 48*S | 1.77 | 474 | 472 | B |
| 49*R | 0.92 | 488 | 486 | A |
| 49*S | 0.93 | 488 | 486 | A |
| 44*R | 1.68 | 506 | 504 | B |
| 44*S | 1.66 | 506 | 504 | B |
| 50 | 9.6 | 515 | / | F |
| 51 | 10.0 | 492 | / | F |
| 52 | 9.7 | 530 | / | F |
| 53 | 1.63 | 494 | 492 | C |
| 54 | 1.88 | 535 | 533 | B |
| 55 | 1.96 | 520 | 518 | C |
| 56 | 1.67 | 471 | 469 | C |
| 57trans | 1.66 | 468 | 466 | C |
| 57cis | 1.65 | 468 | 466 | C |
| 58trans | 1.45 | 466 | 464 | C |
| 58cis | 1.43 | 466 | 464 | C |
| 57 | 0.81 | 385 | 383 | A |

TABLE 2

SFC data for compounds

| Cmpd no | Rt (min) | [M + H]+ | [M − H]− | SFC method |
|---|---|---|---|---|
| 15 | 6.00 | 529 | 527 | SFC_C |
| 13 | 6.71 | 495 | 493 | SFC_D |
| 18*R | 6.00 | 486 | 484 | SFC_E |
| 18*S | 6.33 | 486 | 484 | SFC_E |
| 25*R | 6.15 | 509 | 507 | SFC_D |
| 25*S | 5.90 | 509 | 507 | SFC_D |
| 26*R | 5.15 | 501 | 499 | SFC_B |
| 26*S | 6.70 | 501 | 499 | SFC_B |
| 27*S*S | 5.28 | 472 | 470 | SFC_F |
| 27*R*R | 6.58 | 472 | 470 | SFC_F |

TABLE 2-continued

SFC data for compounds

| Cmpd no | Rt (min) | [M + H]+ | [M − H]− | SFC method |
|---|---|---|---|---|
| 24*R | 4.48 | 460 | 458 | SFC_G |
| 24*S | 4.78 | 460 | 458 | SFC_G |
| 34 | 6.31 | 539 | 537 | SFC_D |
| 47*R | 4.69 | 492 | 490 | SFC_A |
| 47*S | 5.42 | 492 | 490 | SFC_A |
| 48*R | 4.29 | 474 | 472 | SFC_D |
| 48*S | 4.59 | 474 | 472 | SFC_D |
| 49*R | 5.00 | 488 | 486 | SFC_A |
| 49*S | 5.67 | 488 | 486 | SFC_A |
| 44*R | 3.79 | 506 | 504 | SFC_H |
| 44*S | 3.29 | 506 | 504 | SFC_H |
| 57trans | 4.17 | 468 | 466 | SFC_H |
| 57cis | 4.43 | 468 | 466 | SFC_H |
| 58trans | 4.31 | 466 | 464 | SFC_C |
| 58cis | 4.48 | 466 | 464 | SFC_C |

TABLE 3

$^1$H NMR results

| Cmpd no | $^1$H NMR results |
|---|---|
| 9 | $^1$H NMR (400 MHz, DMSO-$d_6$, 27° C.) δ ppm 1.70 (s, 6 H), 2.19-2.26 (m, 3 H), 3.94 (s, 3 H), 7.09 (t, J = 9.2 Hz, 1 H), 7.49-7.59 (m, 1 H), 7.62-7.68 (m, 3 H), 8.14 (d, J = 1.3 Hz, 1 H), 8.60 (s, 1 H), 10.07 (s, 1 H) |
| 8 | $^1$H NMR (400 MHz, DMSO-$d_6$, 27° C.) δ ppm 3.30 (s, 4 H) 3.80 (s, 3 H) 7.56 (t, J = 9.13 Hz, 1 H) 7.68-7.89 (m, 1 H) 7.98 (ddd, J = 9.13, 4.84, 2.75 Hz, 1 H) 8.18-8.23 (m, 2 H) 9.79 (s, 1 H) 10.56-10.91 (m, 1 H) 14.43-15.23 (m, 1 H) |
| 7 | $^1$H NMR (400 MHz, DMSO-$d_6$, 27° C.) δ ppm 3.16-3.48 (m, 4 H) 3.83 (s, 3 H) 7.41 (t, J = 9.13 Hz, 1 H) 7.61 (ddd, J = 9.08, 4.24, 2.75 Hz, 1 H) 7.71-7.89 (m, 1 H) 7.98 (dd, J = 6.93, 2.53 Hz, 1 H) 8.05 (d, J = 3.96 Hz, 1 H) 9.79 (s, 1 H) 10.21 (s, 1 H) 14.61-15.14 (m, 1 H) |
| 3 | $^1$H NMR (400 MHz, DMSO-$d_6$, 27° C.) δ ppm 3.30 (s, 4 H) 3.80 (s, 3 H) 7.43 (t, J = 9.13 Hz, 1 H) 7.55-7.68 (m, 1 H) 7.79 (br s, 1 H) 8.00 (dd, J = 6.71, 2.53 Hz, 1 H) 8.11-8.27 (m, 2 H) 9.78 (s, 1 H) 10.57 (s, 1 H) 14.46-15.23 (m, 1 H) |
| 5 | $^1$H NMR (400 MHz, DMSO-$d_6$, 27° C.) δ ppm 3.18-3.45 (m, 4 H) 3.84 (s, 3 H) 7.54 (t, J = 9.13 Hz, 1 H) 7.69-7.86 (m, 1 H) 7.97 (ddd, J = 9.24, 4.84, 2.64 Hz, 1 H) 8.07 (d, J = 4.18 Hz, 1 H) 8.18 (dd, J = 5.83, 2.75 Hz, 1 H) 9.80 (s, 1 H) 10.34 (brs, 1 H) 14.46-15.23 (m, 1 H) |
| 4 | $^1$H NMR (400 MHz, DMSO-$d_6$, 27° C.) δ ppm 3.16-3.50 (m, 4 H) 3.95 (s, 3 H) 7.52 (t, J = 9.13 Hz, 1 H) 7.71 (d, J = 1.76 Hz, 1 H) 7.79 (s, 1 H) 8.03 (ddd, J = 9.24, 4.84, 2.64 Hz, 1 H) 8.17 (d, J = 1.32 Hz, 1 H) 8.23 (dd, J = 5.83, 2.75 Hz, 1 H) 9.76 (s, 1 H) 10.39 (s, 1 H) 14.06-15.80 (m, 1 H) |
| 6 | $^1$H NMR (400 MHz, DMSO-$d_6$, 27° C.) δ ppm 2.07 (s, 0 H) 3.11-3.49 (m, 4 H) 3.94 (s, 3 H) 7.40 (t, J = 9.1 Hz, 1 H) 7.64-7.72 (m, 2 H) 7.73-7.87 (m, 1 H) 8.04 (dd, J = 7.04, 2.64 Hz, 1 H) 8.16 (d, J = 1.54 Hz, 1 H) 9.76 (s, 1 H) 10.25 (s, 1 H) 14.66-15.07 (m, 1 H) |
| 14 | $^1$H NMR (600 MHz, DMSO-$d_6$, 27° C.) δ ppm 3.34 (s, 4 H) 3.80 (s, 3 H) 4.02 (s, 3 H) 7.44 (t, J = 9.08 Hz, 1 H) 7.63 (ddd, J = 9.04, 4.31, 2.58 Hz, 1 H) 7.99 (s, 1 H) 8.00 (dd, J = 6.77, 2.48 Hz, 1 H) 8.20 (s, 1 H) 9.81 (s, 1 H) 10.60 (s, 1 H) |
| 16 | $^1$H NMR (400 MHz, DMSO-$d_6$, 27° C.) δ ppm 3.12-3.41 (m, 4 H) 3.80 (s, 3 H) 4.13 (s, 3 H) 7.43 (t, J = 9.02 Hz, 1 H) 7.60-7.65 (m, 1 H) 7.66 (s, 1 H) 8.00 (dd, J = 6.82, 2.64 Hz, 1 H) 8.17 (s, 1 H) 9.81 (s, 1 H) 10.58 (s, 1 H) |
| 15 | $^1$H NMR (400 MHz, DMSO-$d_6$) δ ppm 3.34-3.52 (m, 4 H), 3.78 (s, 3 H), 3.96 (s, 3 H), 7.42 (t, J = 9.1 Hz, 1 H), 7.62 (ddd, J = 9.1, 4.2, 2.5 Hz, 1 H), 7.88 (s, 1 H), 7.99 (dd, J = 6.8, 2.6 Hz, 1 H), 8.14 (s, 1 H), 10.06 (s, 1 H), 10.57 (s, 1 H) |
| 12 | $^1$H NMR (400 MHz, DMSO-$d_6$) δ ppm 2.41 (s, 3 H), 3.15-3.54 (m, 4 H), 3.76 (s, 3 H), 7.55 (t, J = 9.1 Hz, 1 H), 7.74 (s, 1 H), 7.97 (ddd, J = 9.2, 4.9, 2.7 Hz, 1 H), 8.07 (s, 1 H), 8.20 (dd, J = 5.8, 2.7 Hz, 1 H), 9.65 (s, 1 H), 10.52 (brs, 1 H) |
| 13 | $^1$H NMR (400 MHz, DMSO-$d_6$) δ ppm 2.40 (s, 3 H), 3.16-3.46 (m, 4 H), 3.75 (s, 3 H), 7.42 (t, J = 9.1 Hz, 1 H), 7.61 (ddd, J = 9.0, 4.3, 2.6 Hz, 1 H), 7.76 (s, 1 H), 8.00 (dd, J = 6.8, 2.6 Hz, 1 H), 8.05 (s, 1 H), 9.67 (s, 1 H), 10.38 (s, 1 H), 14.38 (brs, 1 H) |
| 10 | $^1$H NMR (400 MHz, DMSO-$d_6$, 27° C.) δ ppm 1.27 (brs, 4 H), 3.96 (s, 3 H), 7.40-7.63 (m, 2 H), 7.70 (d, J = 1.5 Hz, 1 H), 8.03 (ddd, J = 9.1, 4.9, 2.8 Hz, 1 H), 8.17 (s, 1 H), 8.23 (dd, J = 5.7, 2.6 Hz, 1 H), 9.47 (s, 1 H), 10.39 (s, 1 H), 14.26-15.17 (m, 1 H) |
| 11 | $^1$H NMR (400 MHz, DMSO-$d_6$, 27° C.) δ ppm 0.91 (s, 9 H), 3.95 (s, 3 H), 5.10 (d, J = 10.1 Hz, 1 H), 7.53 (t, J = 9.1 Hz, 1 H), 7.66 (d, J = 1.8 Hz, 1 H), 7.90 (brs, 1 H), 8.03 (ddd, J = 9.3, 4.9, 2.8 Hz, 1 H), 8.08 (d, J = 1.3 Hz, 1 H), 8.22 (dd, J = 5.8, 2.8 Hz, 1 H), 8.76 (br d, J = 8.6 Hz, 1 H), 10.40 (s, 1 H), 14.88 (brs, 1 H) |

TABLE 3-continued

1H NMR results

| Cmpd no | 1H NMR results |
|---|---|
| 17 | 1H NMR (400 MHz, DMSO-d6, 27° C.) δ ppm 3.92-3.97 (m, 3 H), 4.87 (br d, J = 6.5 Hz, 2 H), 4.98 (d, J = 6.7 Hz, 2 H), 7.49-7.58 (m, 1 H), 7.73 (d, J = 1.7 Hz, 1 H), 7.86 (br s, 1 H), 7.93-8.08 (m, 1 H), 8.15-8.27 (m, 2 H), 9.95 (s, 1 H), 10.35-10.44 (m, 1 H), 14.93 (br s, 1 H) |
| 18*R | 1H NMR (400 MHz, DMSO-d6) δ ppm 2.19-2.44 (m, 3 H), 2.59-2.69 (m, 1 H), 2.92 (q, J = 15.3 Hz, 1 H), 3.17 (td, J = 14.9, 7.9 Hz, 1 H), 3.94 (s, 3 H), 7.53 (t, J = 9.1 Hz, 1 H), 7.68 (d, J = 1.8 Hz, 1 H), 7.77 (br s, 1 H), 8.03 (ddd, J = 9.3, 4.9, 2.8 Hz, 1 H), 8.09 (d, J = 1.4 Hz, 1 H), 8.23 (dd, J = 5.7, 2.7 Hz, 1 H), 9.20 (s, 1 H), 10.40 (s, 1 H), 14.39-15.51 (m, 1 H) |
| 18*S | 1H NMR (400 MHz, DMSO-d6) δ ppm 2.20-2.48 (m, 3 H), 2.60-2.71 (m, 1 H), 2.85-2.99 (m, 1 H), 3.10-3.24 (m, 1 H), 3.94 (s, 3 H), 7.53 (t, J = 9.1 Hz, 1 H), 7.68 (d, J = 1.8 Hz, 1 H), 7.77 (s, 1 H), 8.03 (ddd, J = 9.2, 4.9, 2.8 Hz, 1 H), 8.09 (d, J = 1.4 Hz, 1 H), 8.23 (dd, J = 5.9, 2.7 Hz, 1 H), 9.20 (s, 1 H), 10.40 (s, 1 H), 14.28-15.47 (m, 1 H) |
| 20RS | 1H NMR (400 MHz, DMSO-d6) δ ppm 2.97-3.14 (m, 2 H), 3.97 (s, 3 H), 5.52 (td, J = 9.1, 4.6 Hz, 1 H), 7.53 (t, J = 9.2 Hz, 1 H), 7.72 (d, J = 1.8 Hz, 1 H), 7.85 (s, 1 H), 8.03 (ddd, J = 9.2, 5.0, 2.8 Hz, 1 H), 8.20-8.27 (m, 2 H), 9.40 (d, J = 8.8 Hz, 1 H), 10.40 (s, 1 H) |
| 21 | 1H NMR (400 MHz, DMSO-d6, 27° C.) δ ppm 3.95 (s, 3 H), 4.85 (d, J = 15.0 Hz, 2 H), 4.95 (br d, J = 15.0 Hz, 2 H), 7.53 (t, J = 9.1 Hz, 1 H), 7.72 (d, J = 1.8 Hz, 1 H), 7.94 (s, 1 H), 8.04 (ddd, J = 9.3, 4.9, 2.8 Hz, 1 H), 8.18 (d, J = 1.3 Hz, 1 H), 8.23 (d, J = 5.6 Hz, 1 H), 10.10 (br s, 1 H), 10.41 (s, 1 H) |
| 22 | 1H NMR (400 MHz, DMSO-d6, 27° C.) δ ppm 2.32 (s, 3 H), 3.17-3.29 (m, 4 H), 3.95 (s, 3 H), 7.53 (t, J = 9.1 Hz, 1 H), 7.72 (d, J = 1.7 Hz, 1 H), 8.04 (ddd, J = 9.2, 4.9, 2.8 Hz, 1 H), 8.20 (s, 1 H), 8.24 (d, J = 5.8 Hz, 1 H), 9.62 (brs, 1 H), 10.41 (brs, 1 H), 13.36 (brs, 1 H) |
| 23 | 1H NMR (400 MHz, DMSO-d6, 27° C.) δ ppm 2.42 (s, 3 H) 3.31 (br s, 4 H) 3.64 (s, 3 H) 7.55 (t, J = 9.13 Hz, 1 H) 7.77 (s, 1 H) 7.98 (ddd, J = 9.19, 4.79, 2.75 Hz, 1 H) 8.21 (dd, J = 5.72, 2.64 Hz, 1 H) 9.75 (s, 1 H) 10.73 (brs, 1 H) 14.04-15.87 (m, 1 H) |
| 24RS | 1H NMR (400 MHz, DMSO-d6, 27° C.) δ ppm 2.53-2.73 (m, 2 H) 3.97 (s, 3 H) 5.37 (td, J = 9.08, 5.39 Hz, 1 H) 5.83-6.37 (m, 1 H) 7.53 (t, J = 9.13 Hz, 1 H) 7.72 (d, J = 1.76 Hz, 1 H) 7.81 (s, 1 H) 8.04 (ddd, J = 9.24, 4.84, 2.86 Hz, 1 H) 8.19-8.28 (m, 2 H) 9.30 (d, J = 8.80 Hz, 1 H) 10.40 (s, 1 H) 13.77-15.82 (m, 1 H) |
| 24*R | 1H NMR (400 MHz, DMSO-d6, 27° C.) δ ppm 2.15-2.44 (m, 6 H) 2.56-2.69 (m, 1 H) 2.90 (q, J = 15.8 Hz, 1 H) 3.08-3.23 (m, 1 H) 3.69-3.80 (m, 3 H) 7.41 (t, J = 9.1 Hz, 1 H) 7.61 (ddd, J = 9.0, 4.3, 2.6 Hz, 1 H) 7.75 (br s, 1 H) 7.93 (s, 1 H) 7.99 (dd, J = 6.9, 2.6 Hz, 1 H) 9.14 (s, 1 H) 10.36 (s, 1 H) 14.34-15.44 (m, 1 H) |
| 25*S | 1H NMR (400 MHz, DMSO-d6, 27° C.) δ ppm 2.10-2.44 (m, 6 H) 2.56-2.67 (m, 1 H) 2.81-2.99 (m, 1 H) 3.07-3.23 (m, 1 H) 3.74 (s, 3 H) 7.41 (t, J = 9.1 Hz, 1 H) 7.61 (ddd, J = 9.0, 4.3, 2.6 Hz, 1 H) 7.64-7.86 (m, 1 H) 7.93 (s, 1 H) 7.99 (dd, J = 6.8, 2.6 Hz, 1 H) 9.14 (s, 1 H) 10.36 (s, 1 H) 14.06-15.66 (m, 1 H) |
| 26*R | 1H NMR (400 MHz, DMSO-d6, 27° C.) δ ppm 2.40 (s, 3 H) 2.91-3.13 (m, 2 H) 3.77 (s, 3 H) 5.51 (td, J = 8.91, 4.84 Hz, 1 H) 7.41 (t, J = 9.02 Hz, 1 H) 7.55-7.68 (m, 1 H) 7.83 (s, 1 H) 8.00 (dd, J = 6.82, 2.64 Hz, 1 H) 8.15 (s, 1 H) 9.30 (d, J = 9.02 Hz, 1 H) 10.38 (brs, 1 H) |
| 26*S | 1H NMR (400 MHz, DMSO-d6, 27° C.) δ ppm 2.40 (s, 3 H), 2.92-3.13 (m, 2 H), 3.77 (s, 3 H), 5.50 (td, J = 8.9, 4.8 Hz, 1 H), 7.41 (t, J = 9.0 Hz, 1 H), 7.62 (ddd, J = 9.0, 4.4, 2.6 Hz, 1 H), 7.76 (s, 1 H), 8.00 (dd, J = 6.8, 2.6 Hz, 1 H), 8.16 (s, 1 H), 9.25 (d, J = 9.0 Hz, 1 H), 10.39 (brs, 1 H) |
| 27*S*S | 1H NMR (400 MHz, DMSO-d6, 40° C.) δ ppm 1.62 (ddd, J = 9.7, 6.3, 3.2 Hz, 1 H), 1.84 (br t, J = 6.4 Hz, 1 H), 2.08-2.19 (m, 1 H), 3.96 (s, 3 H), 5.34-5.80 (m, 1 H), 7.51 (t, J = 9.1 Hz, 1 H), 7.69 (d, J = 1.8 Hz, 1 H), 7.78 (brs, 1 H), 8.03 (ddd, J = 9.2, 4.9, 2.9 Hz, 1 H), 8.17 (d, J = 1.3 Hz, 1 H), 8.22 (dd, J = 5.8, 2.8 Hz, 1 H), 9.62 (s, 1 H), 10.35 (s, 1 H), 14.89 (br s, 1 H) |
| 27*R*R | 1H NMR (400 MHz, DMSO-d6, 27° C.) δ ppm 1.61 (ddd, J = 9.6, 6.2, 3.1 Hz, 1 H), 1.84 (br t, J = 5.9 Hz, 1 H), 2.08-2.20 (m, 1 H), 3.96 (s, 3 H), 5.39-5.76 (m, 1 H), 7.53 (t, J = 9.2 Hz, 1 H), 7.70 (d, J = 1.8 Hz, 1 H), 7.79 (brs, 1 H), 8.03 (ddd, J = 9.2, 4.8, 2.9 Hz, 1 H), 8.19 (d, J = 1.3 Hz, 1 H), 8.23 (dd, J = 5.9, 2.6 Hz, 1 H), 9.69 (s, 1 H), 10.39 (s, 1 H), 14.91 (br s, 1 H) |
| 24*R | 1H NMR (400 MHz, DMSO-d6, 27° C.) δ ppm 2.47-2.73 (m, 2 H) 3.97 (s, 3 H) 5.37 (td, J = 8.91, 5.28 Hz, 1 H) 6.12 (tt, J = 56.29, 4.57 Hz, 1 H) 7.53 (t, J = 9.13 Hz, 1 H) 7.72 (d, J = 1.76 Hz, 1 H) 7.82 (s, 1 H) 8.03 (ddd, J = 9.24, 4.95, 2.75 Hz, 1 H) 8.16-8.29 (m, 2 H) 9.30 (d, J = 9.02 Hz, 1 H) 10.40 (s, 1 H) 14.87 (br s, 1 H) |
| 24*S | 1H NMR (400 MHz, DMSO-d6, 27° C.) δ ppm 2.52-2.74 (m, 2 H) 3.97 (s, 3 H) 5.37 (td, J = 9.02, 5.50 Hz, 1 H) 6.12 (tt, J = 56.04, 4.59 Hz, 1 H) |

TABLE 3-continued

¹H NMR results

| Cmpd no | ¹H NMR results |
|---|---|
| | 7.53 (t, J = 9.13 Hz, 1 H) 7.72 (d, J = 1.76 Hz, 1 H) 7.82 (s, 1 H) 8.04 (ddd, J = 9.24, 4.95, 2.75 Hz, 1 H) 8.18-8.31 (m, 2 H) 9.30 (d, J = 8.80 Hz, 1 H) 10.39 (s, 1 H) 14.47-15.08 (m, 1 H) |
| 28 | ¹H NMR (400 MHz, DMSO-d₆, 27° C.) δ ppm 2.19 (s, 3 H) 2.35 (s, 3 H) 3.15-3.42 (m, 4 H) 3.59 (s, 3 H) 7.54 (t, J = 9.14 Hz, 1 H) 7.73-7.87 (m, 1 H) 7.92-8.03 (m, 1 H) 8.20 (dd, J = 5.80, 2.67 Hz, 1 H) 9.70 (s, 1 H) 10.50 (s, 1 H) 14.63-15.21 (m, 1 H) |
| 29 | ¹H NMR (400 MHz, DMSO-d₆, 27° C.) δ ppm 2.19 (s, 3 H) 2.35 (s, 3 H) 2.51 (dt, J = 3.69, 1.79 Hz, 1 H) 3.59 (s, 3 H) 5.36 (br d, J = 7.70 Hz, 1 H) 5.82-6.42 (m, 1 H) 7.54 (t, J = 9.13 Hz, 1 H) 7.73 (s, 1 H) 7.97 (ddd, J = 9.24, 4.84, 2.64 Hz, 1 H) 8.02 (s, 1 H) 8.21 (dd, J = 5.72, 2.64 Hz, 1 H) 9.13-9.49 (m, 1 H) 10.50 (s, 1 H) 14.85 (br s, 1 H) |
| 30 | ¹H NMR (400 MHz, DMSO-d₆, 27° C.) δ ppm 3.23-3.29 (m, 1 H), 3.33-3.43 (m, 3 H), 3.96 (s, 3 H), 7.54 (t, J = 9.1 Hz, 1 H), 7.73 (br s, 1 H), 8.04 (ddd, J = 9.2, 5.0, 2.8 Hz, 1 H), 8.20 (s, 1 H), 8.24 (dd, J = 5.8, 2.8 Hz, 1 H), 8.50 (br s, 1 H), 9.66 (br s, 1 H), 10.40 (s, 1 H), 13.86 (br s, 1 H) |
| 31 | ¹H NMR (400 MHz, DMSO-d₆, 80° C.) δ ppm 3.20-3.33 (m, 2 H) 3.34-3.47 (m, 2 H) 3.81 (s, 3 H) 7.47-7.56 (m, 1 H) 7.72-7.78 (m, 1 H) 7.96-8.03 (m, 1 H) 8.13-8.20 (m, 2 H) 9.49-9.58 (m, 1 H) 10.22-10.80 (m, 1 H) 13.89-15.43 (m, 1 H) |
| 32 | ¹H NMR (400 MHz, DMSO-d₆, 80° C.) δ ppm 14.75 (br.s, 1H), 9.66 (s, 1H), 9.50 (s, 1H), 8.20-8.17 (m, 1H), 8.06-8.00 (m, 1H), 7.99 (s, 1H), 7.76 (br.s, 1H), 7.49 (t, J = 9.2 Hz, 1H), 3.98 (s, 3H), 3.89 (s, 3H), 3.44-3.22 (m, 4H). |
| 33 | ¹H NMR (400 MHz, DMSO-d₆) δ ppm 3.20-3.47 (m, 4 H) 3.88 (s, 3 H) 7.56-7.64 (m, 1 H) 7.77-7.88 (m, 1 H) 7.92-7.99 (m, 1 H) 8.18-8.23 (m, 1 H) 8.34 (s, 1 H) 9.93 (s, 1 H) 10.38-11.94 (m, 1 H) 14.11-15.47 (m, 1 H) |
| 34 | ¹H NMR (400 MHz, DMSO-d₆, 27° C.) δ ppm 2.40 (s, 3 H) 3.20-3.45 (m, 4 H) 3.75 (s, 3 H) 7.38 (t, J = 8.80 Hz, 1 H) 7.66 (ddd, J = 9.02, 4.40, 2.64 Hz, 1 H) 7.77 (s, 1 H) 8.05 (s, 1 H) 8.12 (dd, J = 6.38, 2.42 Hz, 1 H) 9.67 (s, 1 H) 10.35 (s, 1 H) 14.83 (br s, 1 H) |
| 35 | ¹H NMR (400 MHz, acetone, 27° C.) δ ppm 2.27-2.37 (m, 3 H) 3.32-3.50 (m, 4 H) 3.71-3.82 (m, 3 H) 7.32 (t, J = 9.02 Hz, 1 H) 7.69 (dtd, J = 10.32, 2.76, 2.76, 1.32 Hz, 1 H) 7.84 (s, 1 H) 8.09 (d, J = 6.49 Hz, 1 H) 8.74 (s, 1 H) 9.54 (s, 1 H) |
| 36 | ¹H NMR (400 MHz, DMSO-d₆, 27° C.) δ ppm 3.17-3.30 (m, 2 H), 3.34-3.48 (m, 2 H), 3.94 (s, 3 H), 7.24-7.32 (m, 1 H), 7.34-7.42 (m, 2 H), 7.46-7.57 (m, 3 H), 7.69 (d, J = 1.8 Hz, 1 H), 8.03 (ddd, J = 9.3, 4.9, 2.8 Hz, 1 H), 8.13 (d, J = 1.3 Hz, 1 H), 8.22 (dd, J = 5.8, 2.8 Hz, 1 H), 9.78 (s, 1 H), 10.38 (s, 1 H) |
| 37 | ¹H NMR (400 MHz, DMSO-d₆, 27° C.) δ ppm 3.17-3.51 (m, 4 H) 3.66 (s, 3 H) 7.06-7.87 (m, 6 H) 7.99-8.10 (m, 1 H) 10.90-11.72 (m, 1 H) |
| 38 | ¹H NMR (400 MHz, DMSO-d₆, 27° C.) δ ppm 0.26-0.36 (m, 2 H) 0.72-0.82 (m, 2 H) 2.00-2.12 (m, 1 H) 3.14-3.49 (m, 4 H) 3.71 (s, 3 H) 7.50-7.59 (m, 1 H) 7.72-7.80 (m, 1 H) 7.98 (s, 2 H) 8.18-8.25 (m, 1 H) 9.62-9.71 (m, 1 H) 10.52-10.62 (m, 1 H) 14.05-15.39 (m, 1 H) |
| 39 | ¹H NMR (400 MHz, DMSO-d₆, 27° C.) δ ppm 2.42 (s, 3 H), 3.32-3.52 (m, 4 H), 3.74 (s, 3 H), 7.42 (t, J = 9.1 Hz, 1 H), 7.58-7.65 (m, 1 H), 8.00 (dd, J = 6.8, 2.6 Hz, 1 H), 8.09 (s, 1 H), 9.98 (s, 1 H), 10.37 (s, 1 H), 16.50 (brs, 1 H) |
| 40 | ¹H NMR (400 MHz, DMSO-d₆, 82° C.) δ ppm 10.26 (br d, J = 7.0 Hz, 1H), 9.49 (s, 1H), 8.07 (dd, J = 2.6, 6.4 Hz, 1H), 7.74 (s, 1H), 7.64 (ddd, J = 2.6, 4.4, 9.0 Hz, 1H), 7.33 (t, J = 8.9 Hz, 1H), 3.66 (s, 3H), 3.36-3.26 (m, 4H), 2.25 (s, 3H) |
| 41 | ¹H NMR (400 MHz, DMSO-d₆, 82° C.) δ ppm 10.28 (br d, J = 3.5 Hz, 1H), 9.48 (s, 1H), 7.94 (dd, J = 2.6, 6.8 Hz, 1H), 7.74 (s, 1H), 7.60 (ddd, J = 2.6, 4.2, 9.0 Hz, 1H), 7.35 (t, J = 9.0 Hz, 1H), 3.78-3.61 (m, 3H), 3.42-3.23 (m, 5H), 2.21 (s, 3H) |
| 42 | ¹H NMR (400 MHz, DMSO-d₆) δ ppm 14.93 (br.s, 1H), 10.42 (s, 1H), 9.76 (s, 1H), 8.16 (dd, J = 5.6, 2.8 Hz, 1H), 7.95 (ddd, J = 9.2, 4.8, 2.8 Hz, 1H), 7.75 (br.s, 1H), 7.53 (t, J = 9.2 Hz, 1H), 3.71 (s, 3H), 3.34-3.20 (m, 4H), 2.48 (s, 3H). |
| 43 | ¹H NMR (400 MHz, DMSO-d₆, 27° C.) δ ppm 3.17 (d, J = 5.06 Hz, 2 H) 3.36 (s, 2 H) 3.96 (s, 3 H) 6.86 (s, 1 H) 7.00 (s, 1 H) 7.53 (t, J = 9.24 Hz, 1 H) 7.76 (d, J = 1.76 Hz, 1 H) 8.04 (ddd, J = 9.24, 4.95, 2.75 Hz, 1 H) 8.22 (d, J = 1.32 Hz, 1 H) 8.24 (dd, J = 5.94, 2.64 Hz, 1 H) 9.60 (s, 1 H) 10.39 (s, 1 H) 11.79 (brs, 1 H) |
| 45 | ¹H NMR (400 MHz, DMSO-d₆, 27° C.) δ ppm 2.57 (s, 3 H) 3.22-3.40 (m, 4 H) 3.84 (s, 3 H) 7.51 (t, J = 9.14 Hz, 1 H) 7.74 (s, 1 H) 7.78 (s, 1 H) 8.01 (ddd, J = 9.22, 4.89, 2.72 Hz, 1 H) 8.18-8.24 (m, 1 H) 9.72 (s, 1 H) 10.44 (s, 1 H) 14.32-15.46 (m, 1 H) |
| 46 | ¹H NMR (400 MHz, DMSO-d₆, 27° C.) δ ppm 2.47 (s, 3 H), 3.18-3.47 (m, 4 H), 3.77 (s, 3 H), 7.47 (td, J = 8.9, 1.5 Hz, 1 H), 7.76 (s, 1 H), 8.03-8.12 (m, 2H), 9.66 (s, 1 H), 10.18 (brs, 1 H) |

TABLE 3-continued

¹H NMR results

| Cmpd no | ¹H NMR results |
|---|---|
| 47*R | ¹H NMR (400 MHz, DMSO-d₆, 27° C.) δ ppm 2.41 (s, 3 H) 2.90-3.17 (m, 2 H) 3.77 (s, 3 H) 5.51 (td, J = 9.0, 4.9 Hz, 1 H) 7.55 (t, J = 9.1 Hz, 1 H) 7.86 (br s, 1 H) 7.92-8.02 (m, 1 H) 8.17 (s, 1 H) 8.20 (dd, J = 5.8, 2.7 Hz, 1 H) 9.33 (d, J = 8.9 Hz, 1 H) 10.53 (s, 1 H) 14.95 (br s, 1 H) |
| 47*S | ¹H NMR (400 MHz, DMSO-d₆, 27° C.) δ ppm 2.41 (s, 3 H) 2.97-3.13 (m, 2 H) 3.78 (s, 3 H) 5.51 (td, J = 9.0, 4.9 Hz, 1 H) 7.55 (t, J = 9.1 Hz, 1 H) 7.86 (brs, 1 H) 7.97 (ddd, J = 9.2, 4.9, 2.7 Hz, 1 H) 8.17 (s, 1 H) 8.20 (dd, J = 5.8, 2.7 Hz, 1 H) 9.33 (d, J = 8.9 Hz, 1 H) 10.52 (s, 1 H) 14.94 (br s, 1 H) |
| 48*R | ¹H NMR (400 MHz, DMSO-d₆, 27° C.) δ ppm 1.79 (s, 3 H) 2.40 (s, 3 H) 3.76 (s, 3 H) 6.72 (t, J = 56.4 Hz, 1 H) 7.55 (t, J = 9.1 Hz, 1 H) 7.68-7.93 (m, 1 H) 7.97 (ddd, J = 9.2, 4.8, 2.7 Hz, 1 H) 8.01 (s, 1 H) 8.19 (dd, J = 5.8, 2.7 Hz, 1 H) 9.01 (s, 1 H) 10.52 (s, 1 H) 14.75-15.27 (m, 1 H) |
| 48*S | ¹H NMR (400 MHz, DMSO-d₆, 27° C.) δ ppm 1.79 (s, 3 H) 2.40 (s, 3 H) 3.76 (s, 3 H) 6.72 (t, J = 56.4 Hz, 1 H) 7.55 (t, J = 9.1 Hz, 1 H) 7.72-7.89 (m, 1 H) 7.97 (ddd, J = 9.3, 4.9, 2.8 Hz, 1 H) 8.00 (br s, 1 H) 8.19 (dd, J = 5.8, 2.7 Hz, 1 H) 9.01 (s, 1 H) 10.52 (s, 1 H) 14.85-15.53 (m, 1 H) |
| 49*R | ¹H NMR (400 MHz, DMSO-d₆, 27° C.) δ ppm 1.65 (t, J = 19.2 Hz, 3 H) 2.40 (s, 3 H) 2.54-2.78 (m, 2 H) 3.77 (s, 3 H) 5.43 (td, J = 9.0, 4.5 Hz, 1 H) 7.55 (t, J = 9.1 Hz, 1 H) 7.79 (s, 1 H) 7.97 (ddd, J = 9.2, 4.8, 2.9 Hz, 1 H) 8.14 (s, 1 H) 8.20 (dd, J = 5.8, 2.7 Hz, 1 H) 9.21 (d, J = 8.9 Hz, 1 H) 10.51 (s, 1 H) 14.12-15.47 (m, 1 H) |
| 49*S | ¹H NMR (400 MHz, DMSO-d₆, 27° C.) δ ppm 1.64 (t, J = 19.1 Hz, 3 H) 2.40 (s, 3 H) 2.54-2.77 (m, 2 H) 3.77 (s, 3 H) 5.43 (td, J = 9.0, 4.5 Hz, 1 H) 7.55 (t, J = 9.1 Hz, 1 H) 7.79 (br s, 1 H) 7.97 (ddd, J = 9.2, 4.9, 2.6 Hz, 1 H) 8.14 (s, 1 H) 8.19 (dd, J = 5.8, 2.7 Hz, 1 H) 9.20 (d, J = 9.0 Hz, 1 H) 10.51 (s, 1 H) 14.32-15.49 (m, 1 H) |
| 44*R | ¹H NMR (400 MHz, DMSO-d₆) δ ppm 2.17 (s, 3 H), 2.33 (s, 3 H), 2.91-3.08 (m, 2 H), 3.58 (s, 3 H), 5.49 (td, J = 8.7, 5.3 Hz, 1 H), 7.53 (t, J = 9.1 Hz, 1 H), 7.84 (s, 1 H), 7.96 (ddd, J = 9.2, 4.9, 2.6 Hz, 1 H), 8.20 (dd, J = 5.9, 2.6 Hz, 1 H), 9.37 (d, J = 8.6 Hz, 1 H), 10.49 (s, 1 H), 13.75-15.29 (m, 1 H) |
| 44*S | ¹H NMR (400 MHz, DMSO-d₆) δ ppm 2.17 (s, 3 H), 2.33 (s, 3 H), 2.91-3.08 (m, 2 H), 3.58 (s, 3 H), 5.49 (td, J = 8.6, 5.2 Hz, 1 H), 7.53 (t, J = 9.1 Hz, 1 H), 7.85 (s, 1 H), 7.96 (ddd, J = 9.2, 4.9, 2.6 Hz, 1 H), 8.20 (dd, J = 5.7, 2.6 Hz, 1 H), 9.38 (d, J = 8.4 Hz, 1 H), 10.49 (s, 1 H), 14.08 (brs, 1 H) |
| 50 | ¹H NMR (400 MHz, DMSO-d₆) δ ppm 14.92 (br.s, 1H), 10.87 (br.s, 1H), 10.04 (s, 1H), 8.17 (dd, J = 6.0, 2.8 Hz, 1H), 7.96 (ddd, J = 9.2, 4.8, 2.8 Hz, 1H), 7.82 (br.s, 1H), 7.57 (t, J = 9.2 Hz, 1H), 3.96 (s, 3H), 3.34-3.28 (m, 4H). |
| 51 | ¹H NMR (400 MHz, DMSO-d₆) δ ppm 15.28 (br.s, 1H), 10.54 (s, 1H), 9.13 (s, 1H), 8.20 (dd, J = 5.6, 2.4 Hz, 1H), 8.11 (br.s, 1H), 8.03 (s, 1H), 7.97 (ddd, J = 9.2, 4.8, 2.4 Hz, 1H), 7.55 (t, J = 9.2 Hz, 1H), 3.77 (s, 3H), 2.41 (s, 3H), 2.06 (s, 3H). |
| 52 | ¹H NMR (400 MHz, DMSO-d₆) δ ppm 14.93 (br.s, 1H), 10.38 (s, 1H), 9.71 (s, 1H), 8.16 (dd, J = 6.0, 2.8 Hz, 1H), 7.94 (ddd, J = 9.2, 4.8, 2.8 Hz, 1H), 7.77 (br.s, 1H), 7.53 (t, J = 9.2 Hz, 1H), 3.82 (s, 3H), 3.29 (t, J = 12.4 Hz, 1H), 1.85-1.78 (m, 1H), 0.99-0.94 (m, 2H), 0.59-0.55 (m, 2H). |
| 53 | 1H NMR (400 MHz, DMSO-d₆) δ ppm 2.42 (s, 3 H), 3.18-3.44 (m, 4 H), 3.77 (s, 3 H), 6.92 (t, J = 55.1 Hz, 1 H), 7.70-7.84 (m, 2 H), 8.04 (d, J = 1.8 Hz, 1 H), 8.09 (s, 1 H), 8.57 (d, J = 5.5 Hz, 1 H), 9.69 (s, 1 H), 10.76 (brs, 1 H), 14.85 (brs, 1 H) |
| 54 | ¹H NMR (400 MHz, DMSO-d₆, 27° C.) δ ppm 0.39-0.45 (m, 2 H) 0.78-0.87 (m, 2 H) 1.70-1.78 (m, 1 H) 2.15 (s, 3 H) 3.17-3.27 (m, 1 H) 3.33-3.43 (m, 2 H) 3.68-3.75 (m, 3 H) 7.40 (t, J = 9.13 Hz, 1 H) 7.59 (ddd, J = 8.97, 4.24, 2.64 Hz, 1 H) 7.76 (s, 1 H) 7.98 (dd, J = 6.82, 2.64 Hz, 1 H) 9.56 (s, 1 H) 10.33 (s, 1 H) |
| 55 | ¹H NMR (400 MHz, DMSO-d₆, 27° C.) δ ppm 2.39 (s, 3 H) 3.31 (br s, 2 H) 3.50-3.64 (m, 2 H) 4.05 (s, 3 H) 7.44 (t, J = 9.09 Hz, 1 H) 7.64 (ddd, J = 8.83, 4.13, 2.82 Hz, 1 H) 8.04 (dd, J = 6.79, 2.40 Hz, 1 H) 8.10 (brs, 1 H) 10.74 (s, 1 H) |
| 56 | ¹H NMR (400 MHz, DMSO-d₆) δ ppm 3.11-3.23 (m, 2 H), 3.36-3.46 (m, 2 H), 3.96 (s, 3 H), 6.95 (s, 1 H), 7.53 (t, J = 9.1 Hz, 1 H), 7.60 (s, 1 H), 7.71 (d, J = 1.8 Hz, 1 H), 8.04 (ddd, J = 9.2, 5.0, 2.8 Hz, 1 H), 8.18 (d, J = 1.3 Hz, 1 H), 8.23 (dd, J = 5.8, 2.8 Hz, 1 H), 9.38 (s, 1 H), 10.40 (s, 1 H), 11.92 (brs, 1 H) |
| 57trans | ¹H NMR (400 MHz, DMSO-d₆, 27° C.) δ ppm 2.41 (s, 3 H) 2.71-2.88 (m, 2 H) 2.98-3.10 (m, 2 H) 3.76 (s, 3 H) 5.20 (dquin, J = 56.3, 6.6, 6.6, 6.6, 6.6 Hz, 1 H) 7.55 (t, J = 9.2 Hz, 1 H) 7.69 (s, 1 H) 7.97 (ddd, J = 9.2, 4.9, 2.7 Hz, 1 H) 8.08 (s, 1 H) 8.20 (dd, J = 5.8, 2.7 Hz, 1 H) 9.57 (s, 1 H) 10.52 (brs, 1 H) |
| 57cis | ¹H NMR (400 MHz, DMSO-d₆, 27° C.) δ ppm 2.42 (s, 3 H) 2.66-2.81 (m, 2 H) 3.13-3.27 (m, 2 H) 3.76 (s, 3 H) 5.11-5.37 (m, 1 H) 7.55 (t, J = 9.1 Hz, 1 H) 7.65 (brs, 1 H) 7.97 (ddd, J = 9.2, 4.9, 2.7 Hz, 1 H) 8.05 (s, 1 H) 8.20 (dd, J = 5.8, 2.7 Hz, 1 H) 9.30 (s, 1 H) 10.51 (brs, 1 H) |

TABLE 3-continued

¹H NMR results

| Cmpd no | ¹H NMR results |
|---|---|
| 58trans | ¹H NMR (400 MHz, DMSO-$d_6$, 27° C.) δ ppm 2.29-2.39 (m, 2 H) 2.42 (s, 3 H) 2.95-3.04 (m, 2 H) 3.69-3.82 (m, 3 H) 4.24 (quin, J = 7.4 Hz, 1 H) 7.50-7.62 (m, 2 H) 7.97 (ddd, J = 9.2, 4.9, 2.7 Hz, 1 H) 8.01 (s, 1 H) 8.20 (dd, J = 5.7, 2.6 Hz, 1 H) 9.11 (s, 1 H) 10.15-10.91 (m, 1 H) |
| 58cis | ¹H NMR (400 MHz, DMSO-$d_6$, 27° C.) δ ppm 2.30-2.44 (m, 5 H) 2.84-2.96 (m, 2 H) 3.76 (s, 3 H) 4.07-4.25 (m, 1 H) 5.19 (br d, J = 6.6 Hz, 1 H) 7.54 (t, J = 9.1 Hz, 1 H) 7.67 (brs, 1 H) 7.97 (ddd, J = 9.2, 4.9, 2.7 Hz, 1 H) 8.04 (s, 1 H) 8.20 (dd, J = 5.8, 2.7 Hz, 1 H) 9.35 (s, 1 H) 10.50 (s, 1 H) 14.69 (brs, 1 H) |
| 59 | 1H NMR (400 MHz, DMSO-d6, 27° C.) δ ppm 2.23 (d, J = 1.8 Hz, 3 H), 3.95 (s, 3 H), 4.47 (d, J = 5.9 Hz, 2 H), 7.09 (t, J = 9.1 Hz, 1 H), 7.50-7.59 (m, 1 H), 7.62-7.73 (m, 3 H), 8.18 (d, J = 1.3 Hz, 1 H), 9.21 (brs, 1 H), 10.05 (s, 1 H), 14.48-15.28 (m, 1 H) |

Biological Examples—Anti-HBV Activity of Compounds of Formula (I)

Procedure

The anti HBV activity was measured using the HepG2.117 cell line, a stable, inducible HBV producing cell line, which replicates HBV in the absence of doxicycline (Tet-off system). The HepG2 cell line is available from ATCC® under number HB-8065. Transfection of the HepG2 cell line can be as described in Sun and Nassal 2006 Journal of Hepatology 45 (2006) 636-645 *"Stable HepG2-and Huh7-based human hepatoma cell lines for efficient regulated expression of infectious hepatitis B virus"*.

For the antiviral assay, HBV replication was induced, followed by a treatment with serially diluted compound in 96-well plates. After 3 days of treatment, the antiviral activity was determined by quantification of intracellular HBV DNA using real-time PCR and an HBV specific primer set and probe.

Cytotoxicity of the compounds was tested using HepG2 or HepG2.117 cells, incubated for 4 days in the presence of compounds. The viability of the cells was assessed using the Perkin Elmer ATPlite Luminescence Assay System."

Results

TABLE 4

| Co. No. | HBV-AVE-HepG2.117_intra_$EC_{50}$ (μM; mean value) | $CC_{50}$ (μM, mean value) |
|---|---|---|
| 1 | 0.051 | >50 |
| 2 | 0.032 | 23.8 |
| 9 | 0.019 | >50 |
| 8 | 0.006 | >50 |
| 7 | 0.011 | 13.5 |
| 3 | 0.006 | 22.0 |
| 5 | 0.010 | 11.9 |
| 4 | 0.063 | 8.2 |
| 6 | 0.017 | 7.1 |
| 14 | 0.004 | >50 |
| 16 | 0.003 | >50 |
| 15 | 0.004 | >50 |
| 12 | 0.010 | >50 |
| 13 | 0.003 | 26.8 |
| 10 | 0.150 | >50 |
| 11 | 0.100 | 26.0 |
| 17 | 0.171 | >50 |
| 18*R | 0.015 | 14.1 |
| 18*S | 0.064 | 20.7 |
| 20RS | 0.061 | 12.0 |
| 21 | 1.267 | >50 |
| 22 | 0.124 | 29.5 |
| 23 | 0.004 | >50 |
| 24RS | 0.060 | 22.1 |
| 25*R | 0.003 | 18.6 |
| 25*S | 0.004 | 24.2 |
| 26*R | 0.007 | >50 |
| 26*S | 0.018 | >50 |
| 27*S*S | 0.092 | >50 |
| 27*R*R | 0.273 | 24.3 |
| 24*R | 0.046 | 9.4 |
| 24*S | 0.562 | 28.2 |
| 28 | 0.008 | >50 |
| 29 | 0.009 | >50 |
| 30 | 0.142 | 31.1 |
| 31 | 0.003 | >50 |
| 32 | 0.027 | 31.7 |
| 33 | 0.038 | >50 |
| 34 | 0.004 | 26.3 |
| 35 | 0.004 | 5.8 |
| 36 | 0.010 | 1.1 |
| 37 | 0.670 | >50 |
| 38 | 0.024 | >50 |
| 39 | 1.500 | >50 |
| 40 | 0.004 | 6.6 |
| 41 | 0.002 | 7.2 |
| 42 | 0.002 | >50 |
| 43 | 0.315 | 6.6 |
| 44RS | 0.004 | >50 |
| 45 | 0.009 | >50 |
| 46 | 0.011 | >50 |
| 47*R | 0.021 | >50 |
| 47*S | 0.011 | >50 |
| 48*R | 0.012 | >50 |
| 48*S | 0.004 | >50 |
| 49*R | 0.016 | >50 |
| 49*S | 0.027 | >50 |
| 44*R | 0.005 | >50 |
| 50 | 1.284 | >50 |
| 51 | 0.013 | >50 |
| 44*S | <0.012 | >50 |
| 52 | 0.009 | >40.6 |
| 53 | 0.033 | >50 |
| 54 | 0.003 | 26.3 |
| 55 | 0.809 | >50 |
| 56 | 0.044 | 20.0 |
| 57trans | 0.007 | >50 |
| 58trans | 0.088 | >50 |
| 58cis | 0.090 | >50 |
| 57cis | 0.012 | >50 |
| Ref. 59 | 0.583 | >50 |

As the anti-HBV activity data shown in table 4, compounds 1 and 2 show an improved anti-HBV activity of ~10 and 18 fold improvement, respectively, over Ref. compound 59.

Pharmacokinetics Assessment

The pharmacokinetic profile was evaluated in fed male C57BL mice (n=3/group). Mice were i.v. injected with test compound at 2.5 mg/kg, formulated as solution in PEG400/water (70/30), and blood samples were collected from the dorsal metatarsal vein at 0.05, 0.117, 0.333, 1, 2, 4, 7, and 24 hours into EDTA-containing microcentrifuge tubes. Test compound was administered p.o. at 10 mg/kg and 50 mg/kg, formulated as solution in PEG400, and blood samples were collected from the dorsal metatarsal vein at 0.5, 1, 2, 4, 7, 12 and 24 hours into EDTA-containing microcentrifuge tubes. The blood samples were immediately centrifuged at 4° C. and the plasma was stored at −80° C. Compound concentrations from the plasma samples were analyzed using LC-MS/MS (LCMS-8050 instrument). Individual plasma concentration-time profiles were subjected to a non-compartmental pharmacokinetic analysis (NCA) using Phoenix™ WinNonlin version 6.1. (Certara, N.J., USA).

HT EQ Solubility Assay

The assay was run in triplicate and was semi-automated using the Tecan Fluent for all liquid handling. 20 μL of 10 mM stock solution was dispensed in a 500 μL 96 well plate. DMSO was evaporated (Genevac). A stir bar and 400 μL of buffer/biorelevant media was added. The solution was stirred for 72 h (pH2 and pH7) or 24 h (FaSSIF and FeSSIF). The solution was filtered and the filtrate was quantified by UPLC/UV using a three-points calibration curve.

Thermodynamic Solubility Assay

To x mg of compound 500 μL of solvent was added (max. conc. y mg/mL). After 24 h/72 h shaking/stirring the solutions were filtered (0.45 μm membrane) and the pH was recorded. The filtrate was diluted to a maximum conc. of 100 μg/mL (CH$_3$CN/0.1N HCl 1/1) and the samples were quantified by LC/UV. Calibration standards were 100 μg/mL, 10 μg/mL and 1 μg/mL.

After formaldehyde fixation and Triton-X-100 permeabilization, Hepatitis B virus core protein (HBc) was immunolabeled with a primary anti-HBc antibody. ALEXA 488-conjugated secondary antibody was used for fluorescent detection of the primary HBV Core signal. CELLMASK Deep Red and HOECHST 33258 were used for the detection of cytoplasm and nucleus respectively, which allowed the segmentation of cellular compartments.

An image analysis software that allows to detect different morphological phenotypes was used to determine the level of HBV core in the cytoplasm or nucleus (high content imaging assay).

Compounds of the invention have shown speckling when tested in this assay.

The invention claimed is:

1. A compound of formula (I)

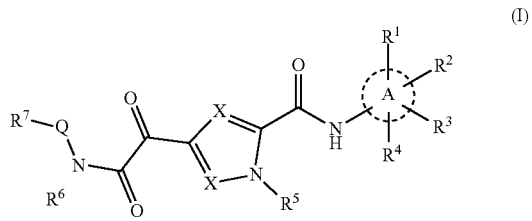

(I)

a stereoisomer or tautomeric form thereof, wherein:

represents a 6-membered aryl optionally containing one or more heteroatoms, the heteroatom or each of the heteroatoms being nitrogen;

TABLE 5

Thermodynamic solubility in PEG400 and HTeqsol (pH = 2, 7, fessif and fessif).

| | Co. No. 12 | Co. No. 13 | Co. No. 28 |
|---|---|---|---|
| PK (mouse) IV (PEG400) 2.5 mg/kg | NA | | |
| CL (mL/min/kg) | | 10.2 +/− 0.6 | 73.3 +/− 26.3 |
| PK (mouse) PO (PEG400) 10 mg/kg | | | |
| Cmax (ng/mL) | | 2485 +/− 582 | 85 +/− 69 |
| AUClast (h*ng/mL) | | 12541 +/− 3203 | 153 +/− 90 |
| F (%) | | 77.3 +/− 19.8 | 6.05 +/− 3.56 |
| PK (mouse) PO (PEG400) 50 mg/kg | NA | | |
| Cmax (ng/mL) | | 12 823 +/− 3049 | 1628 +/− 1237 |
| AUClast (h*ng/mL) | | 94 187 +/− 41573 | 1849 +/− 1522 |
| F (%) | | 121 +/− 50 | 14.6 +/− 12 |
| HtEq Sol (μM) | | | |
| pH = 2 | 1.2/<5 | 1.1 | <5 |
| pH = 7 | 0.7/<5 | <0.6 | <5 |
| fassif | 10.2/5.4 | 39.8 | 46.8 |
| Fessif | 41.2/25.1 | 150.5 | 276.7 |
| PEG400 solubility (mg/mL | NA | >36.41 | >33.9 |

Induction or Non-Induction of HBc Speckling

HepG2.117 cells were cultured in the presence of DMSO or test compound in absence of doxycycline.

R$^1$, R$^2$ and R$^3$ are each independently selected from the group consisting of H, F, Cl, Br, CHF$_2$, CH$_2$F, CF$_3$, CN, C$_1$-C$_4$alkyl and C$_3$-C$_6$cycloalkyl;

$R^4$ is selected from the group consisting of H and F;
$R^5$ is selected from the group consisting of H, $C_1$-$C_4$alkyl, and $C_3$-$C_6$cycloalkyl;
Q is selected from the group consisting of
- $C_2$-$C_5$alkyl, optionally substituted with one or more substituents each independently selected from the group consisting of halogens and $SO_2Me$,
- $C_2$-$C_3$alkenyl substituted with halogens and more particularly one or more fluoro,
- 3- to 6-membered monocyclic saturated rings, wherein the 3- to 6-membered monocyclic saturated rings optionally contain one or more heteroatoms, the heteroatoms being each independently selected from N, O and S, and are optionally substituted with one or more substituents each independently selected from the group consisting of F, oxo, OH, C(=O)NHCH$_3$ and $C_{1-4}$ alkyl optionally substituted with one or more fluoro,
- 3- to 9-membered polycyclic saturated rings, wherein the 3- to 9-membered polycyclic saturated rings optionally contain one or more heteroatoms, the heteroatoms being each independently selected from N, O and S, and are optionally substituted with one or more substituents each independently selected from the group consisting of F, oxo, OH, C(=O)NHCH$_3$ and $C_1$-$C_4$ alkyl optionally substituted with one or more fluoro;

$R^6$ is H;
$R^7$ is selected from the group consisting of phenyl, phenyl substituted with one or more substituents each independently selected from the group consisting of halo, CN, $CF_3$, $CF_2H$, $CH_2F$, $C_1$-$C_4$alkyl, $C_3$-$C_6$cycloalkyl, OH and $OC_1$-$C_4$alkyl, pyridyl, pyridyl substituted with one or more substituents each independently selected from the group consisting of halo, CN, $CF_3$, $CF_2H$, $CH_2F$, $C_1$-$C_4$alkyl, $C_3$-$C_6$cycloalkyl, OH and $OC_1$-$C_4$alkyl, pyrimidyl, pyrimidyl substituted with one or more substituents each independently selected from the group consisting of halo, CN, $CF_3$, $CF_2H$, $CH_2F$, $C_1$-$C_4$alkyl, $C_3$-$C_6$cycloalkyl, OH and $OC_1$-$C_4$alkyl, pyrazinyl, pyrazinyl substituted with one or more substituents each independently selected from the group consisting of halo, CN, $CF_3$, $CF_2H$, $CH_2F$, $C_1$-$C_4$alkyl, $C_3$-$C_6$cycloalkyl, OH and $OC_1$-$C_4$alkyl, pyridazinyl, pyridazinyl substituted with one or more substituents each independently selected from the group consisting of halo, CN, $CF_3$, $CF_2H$, $CH_2F$, $C_1$-$C_4$alkyl, $C_3$-$C_6$cycloalkyl, OH and $OC_1$-$C_4$alkyl, 5-membered unsaturated heterocycles containing one to 4 heteroatoms, the heteroatoms being each independently selected from N, O and S, 5-membered unsaturated heterocycles containing one to 4 heteroatoms, the heteroatoms being each independently selected from N, O and S, substituted with one or more substituents each independently selected from the group consisting of halogens, CN, $CF_3$, $CF_2H$, $CH_2F$, $C_1$-$C_4$alkyl, $C_3$-$C_6$cycloalkyl, OH and $OC_1$-$C_4$alkyl; and
X is $CR^8$; and
$R^8$ is selected from the group consisting of H, F, Cl, Br, CN, $OC_1$-$C_4$alkyl, $C_3$-$C_6$cycloalkyl, $C_2$-$C_3$alkenyl and $C_1$-$C_4$alkyl optionally substituted with one or more F and $OCH_3$, or a pharmaceutically acceptable salt or a solvate thereof.

2. The compound of claim 1, wherein Q is a 3-6 membered monocyclic saturated ring containing one or more heteroatoms, the heteroatoms being each independently selected from N, O and S, and wherein Q is optionally substituted with one or more substituents each independently selected from the group consisting of F, oxo, OH, C(=O)NHCH$_3$, and $C_1$-$C_4$ alkyl optionally substituted with one or more fluoro.

3. The compound of claim 1, wherein Q is a 3-6 membered monocyclic saturated ring optionally containing one or more heteroatoms, the heteroatoms being each independently selected from N, O and S, and wherein Q is substituted with one or more substituents each independently selected from the group consisting of F, oxo, OH, C(=O)NHCH$_3$, and $C_1$-$C_4$alkyl optionally substituted with one or more fluoro.

4. The compound of claim 1, wherein $R^7$ is a 5-membered unsaturated heterocycle containing one to four heteroatoms, the heteroatoms being each independently selected from N, O and S, and optionally substituted with one or more substituents each independently selected from the group consisting of halo, CN, $CF_3$, $CF_2H$, $CHF_2$, $C_1$-$C_4$alkyl, $C_{3-6}$cycloalkyl, OH and $OC_1$-$C_4$alkyl.

5. The compound of claim 1, wherein each of $R^1$ and $R^2$ is H, $R^3$ is methyl, chloro or cyano, and $R^4$ is F.

6. The compound of claim 1, wherein

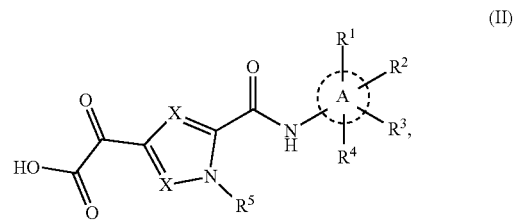

represents phenyl carrying substituents in a meta position and in the para position, whereby one substituent is fluoro and the other substituent is selected from the group consisting of fluoro, chloro, cyano, and methyl.

7. The compound of claim 1, wherein Q is cyclobutyl.

8. The compound of claim 7, wherein the cyclobutyl is substituted with one or more fluoro, more particularly 3,3-difluorocyclobutyl.

9. The compound of claim 1, wherein Q is $C_2$-$C_5$alkyl, particularly ethyl or isopropyl.

10. A pharmaceutical composition comprising at least one compound or pharmaceutically acceptable salt of claim 1.

11. The pharmaceutical composition of claim 10, further comprising at least one pharmaceutically acceptable carrier.

12. A method of treating an HBV infection or an HBV-induced disease in an individual in need thereof, comprising administering to the individual a therapeutically effective amount of the compound of claim 1.

13. A pharmaceutical composition comprising a first compound and a second compound, wherein said first compound is the compound claim 1.

14. A process for the preparation of a compound of Formula (I) of claim 1, comprising the reaction between a compound of Formula (II), wherein Formula (II) is and a compound of Formula (III), wherein Formula (III) is
(III)
in the presence of a base, and a coupling reagent to form a compound of Formula (I).
15. The process of claim 14, wherein the base is Diisopropylethylamine (DIPEA).
16. The process of claim 14, wherein the coupling reagent is Hexafluorophosphate Azabenzotriazole Tetramethyl Uronium (HATU).
* * * * *